US012409068B2

United States Patent
Teuma et al.

(10) Patent No.: US 12,409,068 B2
(45) Date of Patent: Sep. 9, 2025

(54) PATIENT INTERFACE DEVICES AND METHODS AND SYSTEMS FOR COMBINED SONIC AND LASER APPLICATIONS

(71) Applicant: Lensar, Inc., Orlando, FL (US)

(72) Inventors: E. Valaski Teuma, Orlando, FL (US); George Curatu, Orlando, FL (US); Gary P. Gray, Orlando, FL (US); John McWhirter, Winter Park, FL (US); Arthur Newton, Orlando, FL (US); Scott Anderson, Winter Garden, FL (US); Alan Connaughton, Orlando, FL (US); Dustin Morley, Rockledge, FL (US); Dale McPherson, Orlando, FL (US)

(73) Assignee: Lensar, Inc., Orlando, FL (US)

( * ) Notice: Subject to any disclaimer, the term of this patent is extended or adjusted under 35 U.S.C. 154(b) by 819 days.

(21) Appl. No.: 17/140,035

(22) Filed: Jan. 1, 2021

(65) Prior Publication Data
US 2021/0378864 A1    Dec. 9, 2021

Related U.S. Application Data

(60) Provisional application No. 62/956,731, filed on Jan. 3, 2020.

(51) Int. Cl.
*A61F 9/008* (2006.01)
*A61B 3/10* (2006.01)
(Continued)

(52) U.S. Cl.
CPC .............. *A61F 9/008* (2013.01); *A61B 3/102* (2013.01); *A61B 3/107* (2013.01); *A61B 3/14* (2013.01);
(Continued)

(58) Field of Classification Search
CPC .................. A61F 9/008; A61F 9/00745; A61F 2009/00844
(Continued)

(56) References Cited

U.S. PATENT DOCUMENTS 4,729,373 A    3/1988 Peyman
4,825,865 A    5/1989 Zelman
(Continued)

FOREIGN PATENT DOCUMENTS

CN         2315667 Y       1/2001
DE    10 2011 16 368       4/2023
(Continued)

OTHER PUBLICATIONS

Jul. 7, 2021, WIPO, 2021/0259880—Opinin and search report.
(Continued)

*Primary Examiner* — Jennifer Pitrak McDonald
*Assistant Examiner* — Michael T. Holtzclaw
(74) *Attorney, Agent, or Firm* — Glen P. Belvis; Belvis Law, LLC.

(57) ABSTRACT

A patient interface device (PID) for contacting the surface of the eye and having a meniscus inverter. A pin, clip and ridge configuration for holding a window and maintaining an open reservoir of BSS in a PID. A PID for integrated systems and methods for performing laser and phacoemulsification operations. A PID for a reconfigurable system for performing a laser procedure in a laser configuration, and then being reconfigured into a phaco configuration, to perform a phacoemulsification, and then being reconfigured back to the laser configuration.

21 Claims, 52 Drawing Sheets

(51) Int. Cl.
- *A61B 3/107* (2006.01)
- *A61B 3/14* (2006.01)
- *A61B 17/00* (2006.01)
- *A61B 18/00* (2006.01)
- *A61B 34/00* (2016.01)
- *A61F 9/007* (2006.01)

(52) U.S. Cl.
CPC .......... *A61B 34/25* (2016.02); *A61F 9/00745* (2013.01); *A61B 2017/00973* (2013.01); *A61B 2018/00994* (2013.01); *A61F 9/00825* (2013.01); *A61F 2009/00844* (2013.01); *A61F 2009/00851* (2013.01); *A61F 2009/0087* (2013.01); *A61F 2009/00887* (2013.01); *A61F 2009/00889* (2013.01)

(58) Field of Classification Search
USPC .......................................................... 606/4
See application file for complete search history.

(56) References Cited

U.S. PATENT DOCUMENTS

| | | | |
|---|---|---|---|
| 4,946,452 | A | 8/1990 | Py |
| 5,057,098 | A | 10/1991 | Zelman |
| 5,098,426 | A | 3/1992 | Sklar |
| 5,139,504 | A | 8/1992 | Zelman |
| 5,423,801 | A | 6/1995 | Marshall |
| 5,548,352 | A | 8/1996 | Dewey |
| 5,591,160 | A | 1/1997 | Reynard |
| 5,651,783 | A | 7/1997 | Reynard |
| 5,695,461 | A | 12/1997 | Schaible |
| 5,722,970 | A | 3/1998 | Colvard et al. |
| 5,741,244 | A | 4/1998 | Klaas |
| 6,045,527 | A | 4/2000 | Appelbaum |
| 6,387,107 | B1 * | 5/2002 | Hellenkamp ........... A61F 9/013 606/166 |
| 6,391,020 | B1 | 5/2002 | Kurtz |
| 6,544,254 | B1 | 4/2003 | Bath |
| 6,607,527 | B1 | 8/2003 | Ruiz |
| 6,733,491 | B2 | 5/2004 | Kadziauskas |
| 6,736,360 | B1 | 5/2004 | Buczek |
| 6,962,583 | B2 | 11/2005 | Kadziauskas |
| 7,130,835 | B2 | 10/2006 | Cox |
| 7,182,759 | B2 | 2/2007 | Kadziauskas |
| 8,986,290 | B2 | 3/2015 | Patton |
| 9,050,171 | B2 | 6/2015 | Foster |
| 9,095,415 | B2 | 8/2015 | Blumenkranz et al. |
| 9,107,732 | B2 | 8/2015 | Blumenkranz et al. |
| 9,259,354 | B2 | 2/2016 | Horvath |
| 9,492,318 | B2 | 11/2016 | Rockley et al. |
| 9,968,485 | B2 * | 5/2018 | McWhirter ............ A61F 9/009 |
| 10,709,610 | B2 | 7/2020 | Morley et al. |
| 10,898,377 | B2 * | 1/2021 | Heitel ................. A61F 9/009 |
| 11,583,446 | B2 * | 2/2023 | Teuma ................. A61F 9/009 |
| 2001/0035702 | A1 | 11/2001 | Murphy |
| 2003/0050629 | A1 | 3/2003 | Kadziauskas |
| 2003/0073984 | A1 | 4/2003 | Maeda |
| 2004/0034340 | A1 | 2/2004 | Biscup |
| 2006/0200068 | A1 | 9/2006 | Kadziauskas |
| 2007/0027470 | A1 | 2/2007 | Dodick |
| 2007/0161972 | A1 | 7/2007 | Felberg |
| 2007/0237620 | A1 | 10/2007 | Muhlhoff |
| 2008/0004608 | A1 | 1/2008 | Dacquay |
| 2008/0071254 | A1 | 3/2008 | Lummis |
| 2008/0103367 | A1 * | 5/2008 | Burba ................. A61F 9/007 600/236 |
| 2009/0049522 | A1 | 2/2009 | Claus |
| 2009/0137991 | A1 | 5/2009 | Kurtz |
| 2009/0247999 | A1 | 10/2009 | Tuan |
| 2009/0271155 | A1 | 10/2009 | Dupps |
| 2010/0042081 | A1 | 2/2010 | Rathjen |
| 2010/0191100 | A1 | 7/2010 | Anderson |
| 2010/0274228 | A1 * | 10/2010 | Mrochen ............ A61F 9/013 604/541 |
| 2011/0022035 | A1 | 1/2011 | Porter |
| 2011/0288470 | A1 | 11/2011 | Boukhny |
| 2012/0022510 | A1 | 1/2012 | Welches |
| 2013/0023864 | A1 | 1/2013 | Blumenkranz |
| 2013/0090636 | A1 | 4/2013 | Patton |
| 2014/0046308 | A1 | 2/2014 | Bischoff |
| 2014/0052113 | A1 | 2/2014 | Kuehnert |
| 2014/0104576 | A1 | 4/2014 | Bor et al. |
| 2014/0107634 | A1 * | 4/2014 | Vogler ................ A61F 9/00825 606/6 |
| 2014/0222050 | A1 * | 8/2014 | Heitel .................. A61F 9/009 606/166 |
| 2014/0276673 | A1 * | 9/2014 | Heitel .................. A61F 9/008 606/4 |
| 2014/0364870 | A1 | 12/2014 | Alvarez et al. |
| 2015/0088175 | A1 * | 3/2015 | McWhirter ............ A61F 9/009 606/166 |
| 2015/0190281 | A1 | 7/2015 | Patton |
| 2015/0255004 | A1 | 9/2015 | Manzke |
| 2016/0045367 | A1 | 2/2016 | Horvath |
| 2016/0089269 | A1 | 3/2016 | Horvath |
| 2016/0302915 | A1 | 10/2016 | Sayegh |
| 2017/0000645 | A1 | 1/2017 | Summers et al. |
| 2017/0000647 | A1 | 1/2017 | Schuele et al. |
| 2017/0056245 | A1 | 3/2017 | Rockley et al. |
| 2017/0119249 | A1 | 5/2017 | Gunn |
| 2017/0119578 | A1 | 5/2017 | Rockley et al. |
| 2017/0290703 | A1 | 10/2017 | Teuma |
| 2017/0340483 | A1 | 11/2017 | Rill et al. |
| 2018/0028355 | A1 * | 2/2018 | Raksi .................. A61B 3/13 |
| 2018/0055581 | A1 | 3/2018 | Papac |
| 2018/0085256 | A1 | 3/2018 | Gray et al. |
| 2018/0161051 | A1 | 6/2018 | Humayun |
| 2018/0168547 | A1 | 6/2018 | Kim |
| 2018/0168859 | A1 | 6/2018 | Zeiss |
| 2018/0185043 | A1 | 7/2018 | Humayun |
| 2018/0206717 | A1 | 7/2018 | Kumar |
| 2018/0250090 | A1 | 9/2018 | Patton |
| 2018/0263813 | A1 | 9/2018 | Teuma |
| 2019/0015252 | A1 | 1/2019 | Lake |
| 2019/0083304 | A1 | 3/2019 | Patton |
| 2019/0083308 | A1 | 3/2019 | Rathjen |
| 2019/0096933 | A1 | 3/2019 | Kido et al. |
| 2019/0262174 | A1 * | 8/2019 | Gooding .............. A61M 1/784 |
| 2019/0298573 | A1 | 10/2019 | Teuma |
| 2019/0365567 | A1 | 12/2019 | Zeiss |
| 2020/0258599 | A1 | 8/2020 | Clark |
| 2021/0259880 | A1 | 8/2021 | Newton et al. |
| 2021/0259881 | A1 | 8/2021 | Gray et al. |
| 2021/0298955 | A1 | 9/2021 | McWhirter et al. |
| 2021/0378864 | A1 | 12/2021 | Teuma et al. |

FOREIGN PATENT DOCUMENTS

| | | |
|---|---|---|
| EP | 2057973 | 5/2009 |
| EP | 2 459 143 | 4/2018 |
| JP | 2015 029641 | 2/2015 |
| KR | 10-2015-0128049 | 11/2015 |
| WO | WO1992017138 | 10/1992 |
| WO | WO1997022304 | 6/1997 |
| WO | WO1998012973 | 4/1998 |
| WO | WO 1999065405 | 12/1999 |
| WO | WO2006074469 | 7/2006 |
| WO | WO2009039315 | 3/2009 |
| WO | WO2009061758 | 5/2009 |
| WO | WO 2011/147570 | 12/2011 |
| WO | WO2012047492 | 4/2012 |
| WO | WO 2012/135073 | 10/2012 |
| WO | WO 2012/152496 | 11/2012 |
| WO | WO 2013057098 | 4/2013 |
| WO | WO2013126653 | 8/2013 |
| WO | WO2014201165 | 12/2014 |
| WO | WO 2016/058931 | 4/2016 |

(56) References Cited

FOREIGN PATENT DOCUMENTS

| WO | WO 2017/153442 | 9/2017 |
| WO | WO 2018/025169 | 2/2018 |

OTHER PUBLICATIONS

Apr. 6, 2021, WIPO, 2021/0259881—Opinin and search report.
May 25, 2021, WIPO, 2021/0298955—Opinin and search report.
Jun. 25, 2021, WIPO, 2021/0378864—Opinin and search report.

* cited by examiner

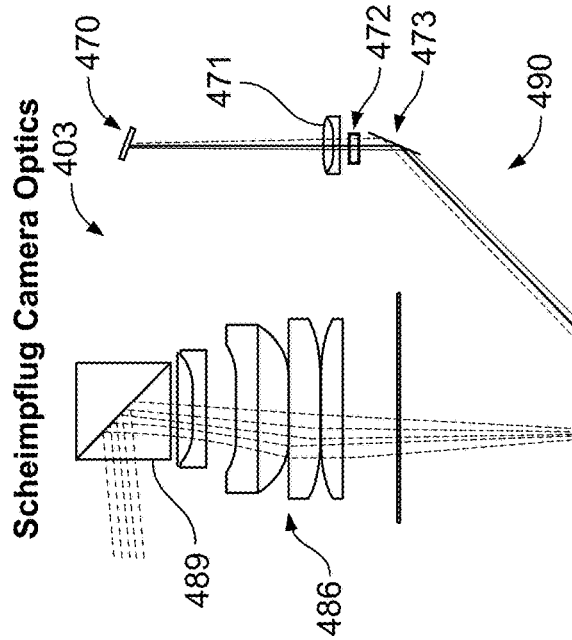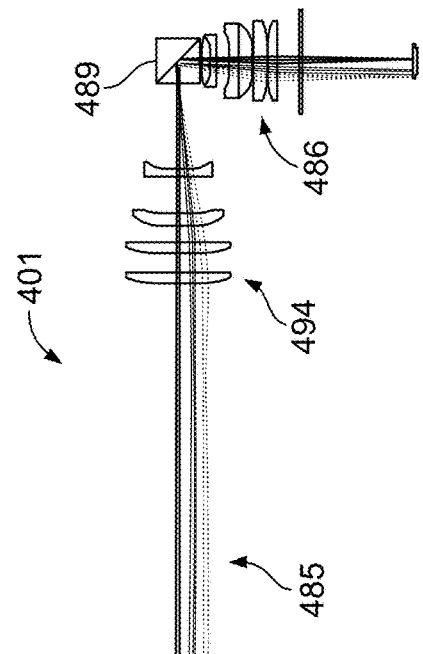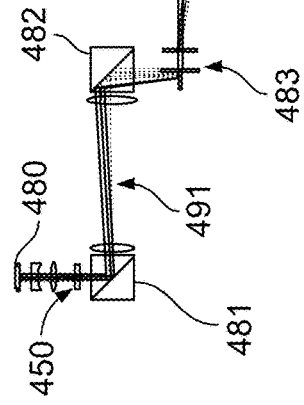

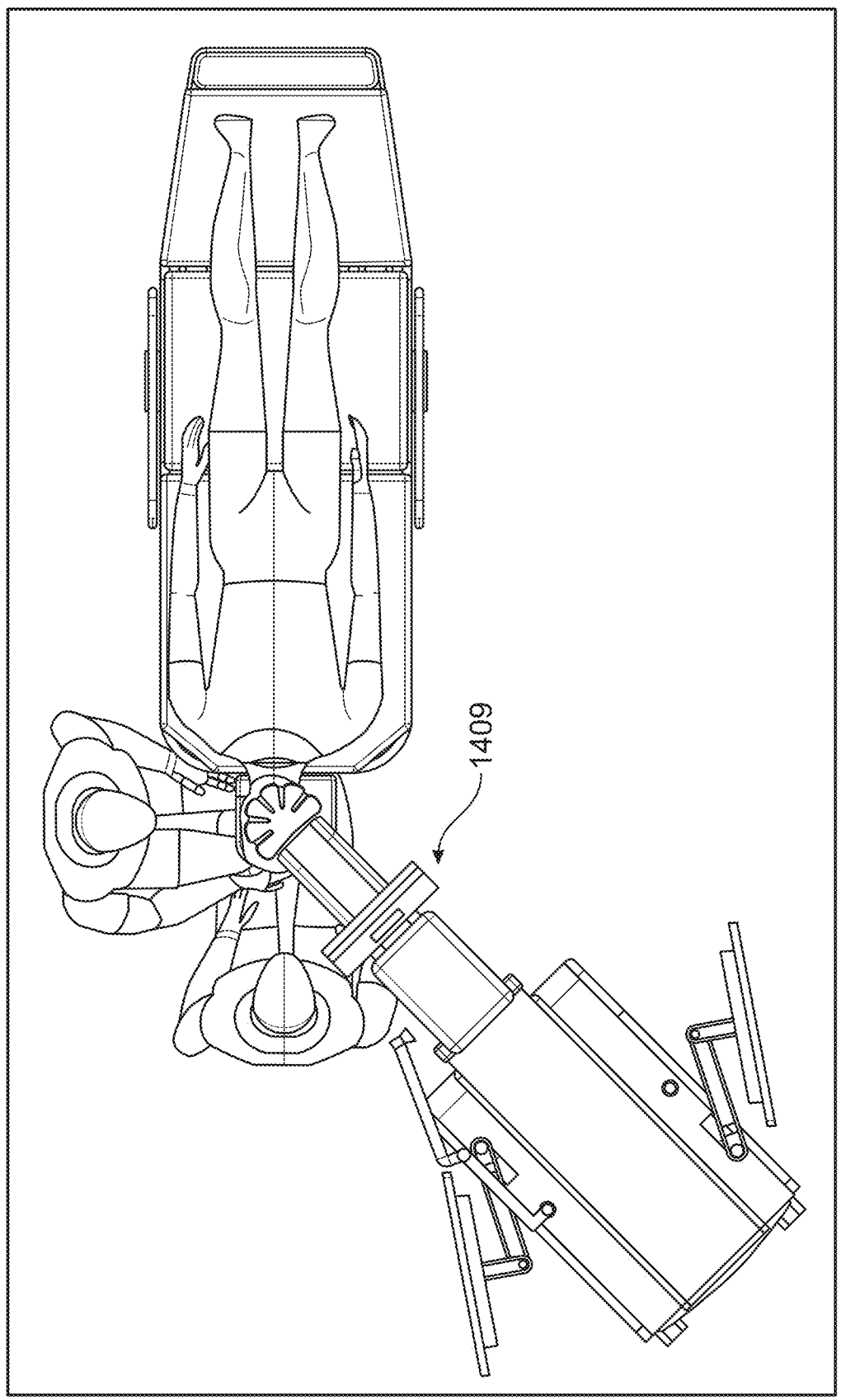

PATIENT INTERFACE DEVICES AND METHODS AND SYSTEMS FOR COMBINED SONIC AND LASER APPLICATIONS

The present application claims priority to and claims under 35 U.S.C. § 119(e)(1) the benefit of the filing date of U.S. provisional application Ser. No. 62/956,731 filed Jan. 3, 2020, the entire disclosure of which is incorporated herein by reference.

BACKGROUND OF THE INVENTION

Field of the Invention

The present invention relates to systems and methods for treating the structures of the eye, including animal, mammal and human eyes. In particular, embodiments of the present inventions relate to systems and methods for the combined use of sonic energy, including ultrasonic, and light energy, including laser, for addressing conditions of the eye.

The anatomical structures of the natural human eye are shown in general in FIG. 11, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIG. 11A, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens.

FIG. 11A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 11 and 11A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 7.2 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general, refractive error is typically due to variations in the axial length of the eye. Myopia is when the eye is too long resulting in the focus falling in front of the retina. Hyperopia is when the eye is too short resulting in the focus falling behind the retina. In general, cataracts are areas of opacification of the ocular lens which are sufficient to interfere with vision.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population.

Accommodative amplitude has been shown to decline with age steadily through the fifth decade of life.

As used herein unless specified otherwise, the recitation of ranges of values herein is merely intended to serve as a shorthand method of referring individually to each separate value falling within the range. Unless otherwise indicated herein, each individual value within a range is incorporated into the specification as if it were individually recited herein.

Generally, the term "about" as used herein unless stated otherwise is meant to encompass a variance or range of ±10%, the experimental or instrument error associated with obtaining the stated value, and preferably the larger of these.

As used herein, unless specifically stated otherwise, the terms "phacoemulsification", "phaco", "phaco system", are to be given their broadest construction possible, refer to the same general equipment and procedures and generally relate to the use of ultrasonic energy to drive a needle or tip to, for example, cut, fragment, separate, and emulsify tissue, including tissue of the eye, such as the lens and cataracts. Such procedures and systems may also include components and methods for aspiration, irrigation and both.

As used herein, unless specifically stated otherwise, the terms "femtosecond laser," "femtosecond laser beam", "femtosecond pulse", and similar such terms, are used to refer to the pulse duration, and thus also pulse length of a laser beam (which can also be referred to as pulse width), and would mean all lasers and laser beams with pulse durations of less than 1 picosecond (less than $1 \times 10^{-12}$ seconds) to and including 1 femtosecond (fs) ($1 \times 10^{-15}$ seconds).

As used herein, unless specifically stated otherwise, the terms "picosecond laser," "picosecond laser beam", "picosecond pulse", and similar such terms, are used to refer to the pulse duration, and thus also pulse length of a laser beam, (which can also be referred to as pulse width) and would mean all lasers and laser beams with pulse durations of 1 picosecond (ps) ($1 \times 10^{-12}$ seconds) up to 1 nanosecond (ns) ($1 \times 10^{-9}$ seconds).

As used herein, unless specifically stated otherwise, the terms "distal" and "proximal" have the following means. For the laser, laser beam, and laser components, distal means the side, location or position that is closer to the laser beam source. For the phacoemulsification system, distal means the side, location or position, that is closer to the ultrasound energy source. For the laser, laser beam and laser components, the term proximal means the side, location or position that is further away from, along the laser beam path, the laser beam source; and thus, in operation closer to the patient. For the phacoemulsification system, the term proximal means the side, location or position that is further away from, along the energy transmission path, the ultrasound energy source; and thus, in operation closer to the patient. Conversely, the distal end of the laser component or the phacoemulsification component are further from the patient during operation of those systems.

Ultrasonic energy, in addition to being a diagnostic tool, has therapeutic uses. Ultrasonic energy can be focused, directed, used to move, e.g., oscillate or vibrate, cutting devices, tools or tips to cut, soften or emulsify tissue, to create mists and vapors, and combinations and variations of these. In general, phacoemulsification is a medically recognized technique that uses ultrasonic energy for crystalline lens removal. Generally, phacoemulsification includes making a corneal incision, a scleral incision and one or more both of these. The insertion through one of those incisions of a phacoemulsification handpiece, which is typically comprised of a needle that is ultrasonically driven, in order to, for example, emulsify (i.e., to liquefy), the natural crystalline lens, break a cataract into small pieces, and combinations and variations of these. The emulsified pieces may subsequently be removed using the same handpiece or another handpiece. The surgeon may then insert implants in the eye through the incision.

In general, therapeutic laser procedures for the eye involve positioning the patient on a bed, or patient support, aligning the eye with the laser beam path of the laser system and attaching a patient interface between the laser system and the eye. The therapeutic laser beam is then delivered in a laser beam pattern to perform a therapeutic laser operation on the eye, and in particular, the structures of, or associated with the eye to address conditions of the eye. Thus, for example, laser procedures, to address cataracts, presbyopia, refractive errors (both natural and induced) and other conditions of the eye are known to the art.

To date, in the operating room and medical offices, typical medical ultrasonic devices and systems, and in particular phacoemulsification systems, are standalone systems, having their own power source, control systems, monitors, control and instruction inputs, housing, cabinets and bases. Similarly, to date, in the operating room and medical offices, typical medical therapeutic laser devices and systems are standalone systems, having their own power source, control systems, monitors, control and instruction inputs, housing, cabinets and bases.

Although the art has expressed a need for combining ultrasonic devices with other therapeutic devices, such as lasers, and provided some rudimentary combinations, it is believed that this need has gone largely unanswered. To date, it is believed that no one has successfully integrated a therapeutic ultrasonic system with another system, such as a therapeutic laser delivery system to provide a compact, efficacious medical system that meets both regulatory and medical practitioner's requirements and needs. In particular, prior to the present inventions, it is believed that no one has successfully integrated an ophthalmic phacoemulsification system with an ophthalmic therapeutic laser system to provide a compact, efficacious, ergonomic medical system that meets both regulatory and medical practitioner's requirements and needs. Meeting both of these requirements and needs involves more than just the mere combination of two systems, which combination has been suggested by the art. These needs are meet through the present inventions, embodiments of which provide for integrated ultrasonic-laser, and in particular, phacoemulsification-laser (phaco-laser) systems, that are compact, efficacious, ergonomic, medical system that meet both regulatory and medical practitioner's requirements and needs.

This Background of the Invention section is intended to introduce various aspects of the art, which may be associated with embodiments of the present inventions. Thus, the forgoing discussion in this section provides a framework for better understanding the present inventions, and is not to be viewed as an admission of prior art.

SUMMARY

There has existed a long standing and unfulfilled need to address and improve, alone or in combination, the size of systems in operating rooms and medical offices, the ergonomics of the operating theater, surgical systems and equipment, the time required to efficaciously perform a procedure, and patient comfort, among other things. These long standing needs have been present and continue, in among other things, the field of ophthalmology, including addressing cataracts, addressing refractive based issues, addressing presbyopia, addressing diseases, conditions and injuries of the eye, as well as, in other procedures on, and conditions of, the eye and nearby structures. The present inventions, among other things, solve these and other needs by providing the articles of manufacture, devices and processes set forth in this specification, drawings and claims.

Thus, there is provided a patient interface device (PID) for ophthalmic procedures, the device having: a ridged arm, having a top and a bottom end; the bottom end having an annular ring structure; the annular ring structure having a top side, a bottom side and an opening configured for the transmission of a therapeutic laser beam; a first and a second port; wherein the ports are in fluid communication with at least one of the opening, the top side, and the bottom side; the top side of the annular ring structure having: a plurality of pins extending upward from a surface of the top side and defining a pin height; a plurality of clips extending upwardly above the surface of the top side and having clip engagement surfaces, thereby defining a clip engagement surface height; wherein the clip engagement surface height is greater than the pin height; an annular wall extending upwardly from the surface of the top side and defining a wall height; and, wherein the annular wall defines in part a first annular channel and a second annular channel.

Moreover, there is provided these systems, methods and devices having one or more of the following features: a window, wherein the window defines a window height; and wherein the window is held between the clip engagement surfaces and the pins; and, wherein the window is positioned over the opening; a window, wherein the window defines a window height; and wherein the window is held between the clip engagement surfaces and the pins; and, wherein the window is positioned over the opening, and wherein the bottom of the window is at a height that is higher than the top of the annular wall; an annular vacuum ring structure attached to the bottom side of the annular ring structure; and, wherein the annular vacuum ring is in fluid communication with at least one of the ports; the annular vacuum ring structure having a bottom side; an annular vacuum ring structure attached to the bottom side of the annular ring structure; and, wherein the annular vacuum ring structure is in fluid communication with at least one of the ports; the annular vacuum ring structure having a bottom side; having a flexible eye engagement ring, having an inner annual skirt and outer annual skirt, and thereby defining a flexible annular vacuum channel configured for engagement with an eye; the flexible eye engagement ring attached to the bottom side of the annular vacuum ring structure and in fluid communication with at least one of the ports; and a flexible eye engagement ring, having an inner annual skirt and outer annual skirt, and thereby defining a flexible annular vacuum channel configured for engagement with an eye; the flexible eye engagement ring attached to the bottom side of the annular vacuum ring structure and in fluid communication with at least one of the ports.

In addition, there is provided these systems, methods and devices having one or more of the following features: wherein the pin height is the same as or lower than the wall height; wherein the pin height is lower than the wall height; wherein the pin height is about 1 mm lower than the wall height; wherein the ridged arm is a unitary structure; wherein the annular vacuum ring structure is a unitary structure; wherein the annular ring structure is a unitary structure; wherein the flexible eye engagement ring is a unitary structure; wherein the top end of the arm is attached to one of the present laser-ultrasound, laser-phaco, femto-phaco systems; wherein the top end of the arm is attached to a laser head of one of the present laser-ultrasound, laser-phaco, femto-phaco systems.

Yet further, there is provided a patient interface device (PID) for ophthalmic procedures, the device having: an arm having a top and a bottom end; a structure at the bottom end of the arm supporting a window; and, a meniscus inverter.

Additionally, there is provided a laser-ultrasound system, having: an assembly, the assembly having: a therapeutic laser for providing a therapeutic laser beam along a laser beam path; a phacoemulsification system for providing therapeutic ultrasonic energy; an arm attached to the assembly; the arm having a distal end and a proximal end, wherein the distal end is attached to the assembly; wherein the proximal end has a laser delivery head; wherein the arm contains a portion of the laser beam delivery path; and, has any one of these PIDs.

Yet further, there is provided a laser-ultrasound system, having: a therapeutic laser for providing a therapeutic laser beam along a laser beam path; a phacoemulsification system for providing therapeutic ultrasonic energy; optics defining four pupils in the system, and wherein the laser beam path extends through at least two of the pupils; and, any one of these PIDs.

Moreover, there is provided a laser-ultrasound system, having: a therapeutic laser system; a phacoemulsification system for providing therapeutic ultrasonic energy; and, a safety interlock, whereby the laser system is prevented from firing the laser when the phacoemulsification system is in operation.

In addition, there is provided a laser-ultrasound system, having: a means for providing a first and a second therapeutic laser beam; the system having optics defining a laser beam path; the first and the second laser beam path traveling along the laser beam path; wherein the first therapeutic laser beam has a pulse width of about 1,000 fs to about 2000 fs; the system having a laser beam delivery pattern for performing a lens cut with the first therapeutic laser beam; wherein the second therapeutic laser beam has a pulse width of about 100 fs to about 500 fs; the system having a laser beam delivery pattern for performing a corneal cut with the second therapeutic laser beam; a phacoemulsification system for providing therapeutic ultrasonic energy; and, having any one of these PIDs.

Furthermore, there is provided these systems, methods and devices having one or more of the following features: wherein the system is non-handed; wherein the system has a phaco tray, a phaco cassette and is non-handed; wherein the system has a wireless foot switch, configured to control the laser, the phacoemulsification or both; and, wherein the system has a wireless foot switch; and, wherein the system comprises a laser head defining an opening, wherein a therapeutic laser beam path travels through the opening, and associated with the opening is a means for closing the opening during operation of the phaco system, when the laser head is in a retracted position, or both.

Additionally, there is provided the method of servicing, upgrading a software, operating, or preforming a surgery using, any of these systems.

Furthermore, there is provided a method of laser transmission, the method including transmitting a laser beam through the window of any one of the PIDs of claims 2 to 13.

Further, there is provided these systems, methods and devices wherein the PID creates and maintains an open reservoir of fluid, e.g., BSS, below the lower surface of the window and in contact with the upper surface of the eye. The open revisor has an outer annular wall (ridge) that has a diameter that is greater than the diameter of the window, thereby creating an opening (e.g., an annular opening) between the wall and the window for the fluid, e.g., BSS, to flow from the reservoir. The top of the wall is lower than the bottom side of the window, whereby the meniscus of the fluid, e.g., BSS, is inverted. The top of the wall can be about 1 mm lower, about 0.7 mm lower and about 0.5 mm lower than the bottom of the window. In this manner the fluid is in full contact with the underside of the window and no bubbles are trapped under the window. In this manner the meniscus is inverted in that its outer edge is pointing downward, i.e., like an inverted bowl. Thus, the outer edge is lower than (i.e., proximal to) the center of the meniscus.

Additionally, there is provided these systems, methods and devices wherein the PID creates and maintains an open reservoir of fluid, e.g., BSS, below the lower surface of the window and in contact with the upper surface of the eye; wherein the top of the annular wall forming the reservoir is higher than the bottom of the window, and thus does not invert the meniscus. Thus, the outer edge of the meniscus is pointing upward.

BRIEF DESCRIPTION OF THE DRAWINGS

FIG. 4B is a schematic of an embodiment of the Scheimpflug optical systems and optical paths of the embodiment of FIG. 4.

FIG. 4C is a schematic of an embodiment of the IR camera with viewing along the optical path of the therapeutic laser (down the pipe) optical systems and optical paths of the embodiment of FIG. 4.

FIG. 16C is a plan view of the system of FIG. 14 in an operating room and in a fully extended laser operational configuration in accordance with the present inventions.

FIG. 17A shows the neutral extended position for testing and calibration of the laser systems. FIG. 17B shows the first operational extended position for therapeutic laser operations. FIG. 17C shows the second operational extended position (fully extended) for therapeutic laser operations.

FIG. 20 B is a perspective view of the PID of FIG. 20.

DESCRIPTION OF THE PREFERRED EMBODIMENTS

Figure 1:
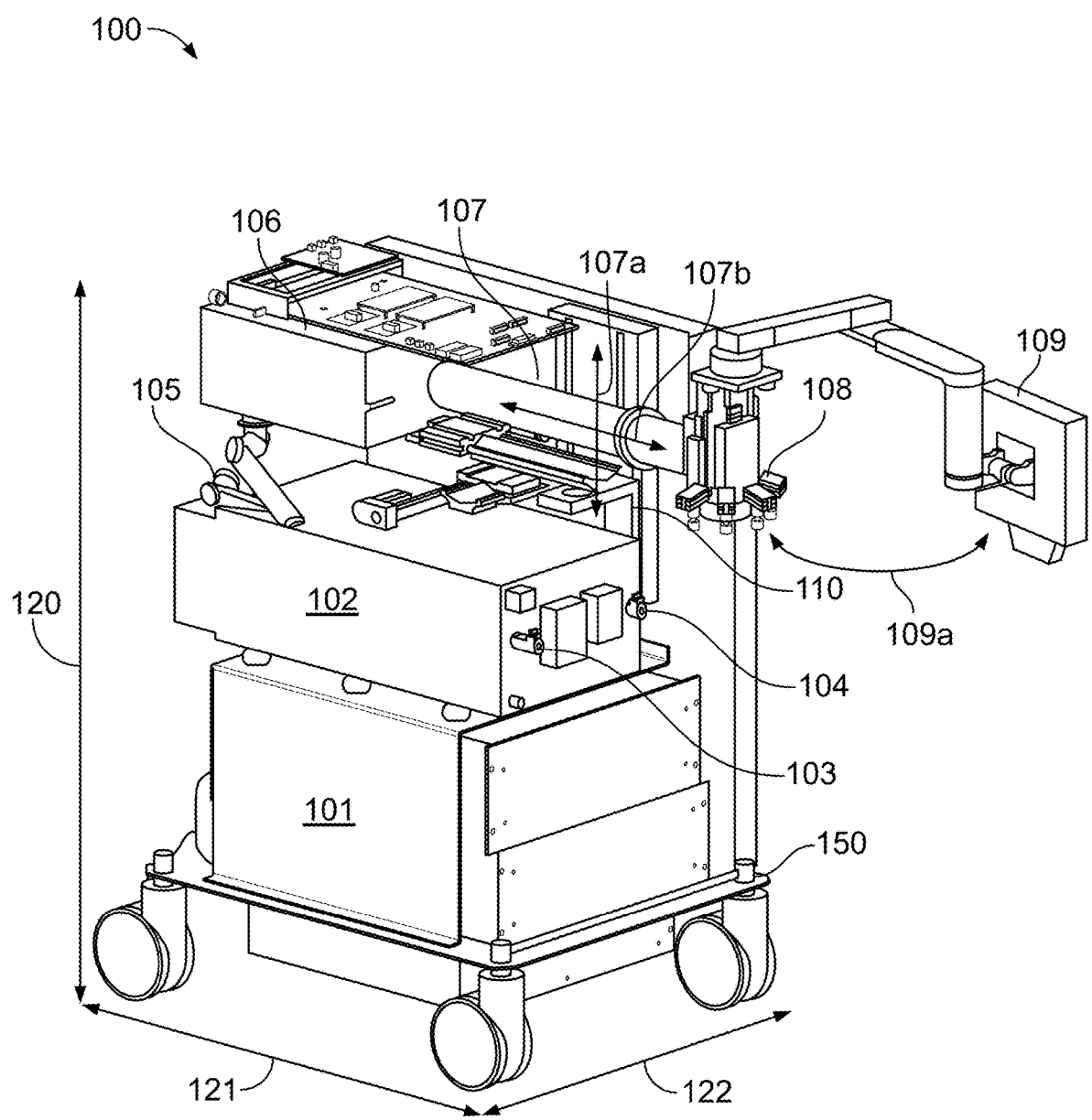
FIG. 1 is a perspective view of an embodiment of a laser-ultrasound system, in accordance with the present inventions.

In general, embodiments of the present inventions provide systems and methods for addressing conditions of the eye, including the cornea, natural crystalline lens, and other structures of and associated with the eye, and in particular for delivering laser energy, ultrasonic energy and both to the eye to address, mitigate, improve and reverse these conditions.

In general, embodiments of the present inventions relate to ergonomic systems, integrated systems, and combinations and variations of these that provide, among other things, the ability to use ultrasound and laser beams to diagnose, treat and combinations and variations of these, conditions of the human eye and its related structures. In embodiments of the present system the laser and ultrasound components are integrated into a single device that is configured to operate, control and deliver therapeutic ultrasound energy and laser energy to the eye. Embodiments these integrated devices can have: integrated and interactive control systems; integrated patient information systems; integrated billing systems; integrated electronic medical records; integrated and interactive operation, control, delivery, voice commands, voice recognition, and voice controlled menus and combinations of these systems, between the laser and ultrasound system; integrated and interactive protocol, including safety systems, between the laser and ultrasound system; integrated and interactive input systems for surgeons and practitioners to input information and instructions into the device; integrated and interactive monitoring systems, displays and both; integrated and common power sources and power management; integrated thermal load, (e.g., heat) management; non-interfering energy generation and delivery systems; and combinations and variations of these features, as well as other features.

In an embodiment, these integrated devices or systems are associated with and form a further system with a patient support bed. In a preferred embodiment these devices and this patient support bed are configured to permit multiple avenues of access by a surgeon to the left and the right eye of the patient, without requiring movement or reposting of the patient. Thus, this preferred embodiment of the system permits surgeons to easily position patients, based upon the surgeons individual preferred method of approaching one or both of the eyes, without having to reposition the patient, and without having to reconfigure the laser, the ultrasound, and both. In this manner, patient conform is enhanced, ergonomics for the surgeon are enhanced, efficiency is enhanced, efficacy is enhanced, time to complete the total procedure (e.g., both eyes) on a patient is reduced, and combinations and variations of these and other benefits can be obtained.

In an embodiment, these integrated devices or systems are associated with a phaco tray or phaco cassette that is configured for orientation and operation from either side of the system. In this manner the surgeon can access and use the components of the cassette from any of the possible surgeon-patient orientations that the system provides.

In an embodiment, these integrated device or systems provide the ability for the surgeon to shift from or between laser and phaco operations without having to move the patient, without the surgeon having to change positions relative to the system, and preferably both.

In embodiments the patient is positioned on a patient support, e.g., a support bed. The system is then moved into position near the patient. The system can be positioned by the surgeon in any of the multiple orientations described in this specification. The laser system and the ultrasound systems are then used to perform the procedures on the patient.

Embodiments of the present systems can include one or more and all of the features of the foregoing embodiments and paragraphs, as well as, embodiments in the following paragraphs.

Embodiments of these systems, such as an embodiment of an integrated phaco-laser system are configured to, and capable of addressing various conditions of the eye, and performing various procedures on the eye, including for example: capsulotomies; custom shaped non-circular and non-elliptical capsulotomies; lens cutting, fragmentation, sectioning and removal; cataract cutting, fragmentation, separation and removal; emulsification of lens and cataract tissue; corneal cutting and incisions; creation of corneal flaps and pockets; making limbal relaxing incisions; addressing and correcting refractive errors (natural and induced); removal of residual cortical material; removal of lens epithelial cells; vitreous aspiration and cutting associated with anterior vitrectomy; addressing bipolar coagulation; and intraocular lens injection.

Embodiments of these systems, such as an embodiment of an integrated phaco-laser system are configured to, and capable of addressing various conditions of the eye, and performing various procedures including keratoplasty, radial keratotomy (RK), astigmatic keratotomy (AK) and limbal relaxing incisions (LRI), and combinations and variations of these. These incisions can be made by the laser prior to or after the phaco procedure and lens implantation. RK would include, micro-RK, micro-RK'AK and traditional RK, while micro-RKs are preferred. For micro-RK the radial incisions can be used in optical zones that are preferably larger about 5.00 mm and larger, however smaller zones are contemplated. The length of the incisions is typically about 2.50 mm. The typical parameters for the incisions are set forth in Table 1. Typically, 1, 2, 3, or more incisions are made in the cornea in a micro-RK procedure.

TABLE 1

| Radial Incision Parameter | Range | Preferred Value | Default Value | Units |
|---|---|---|---|---|
| Optical Zone | 4.00-6.25 | 5.00 | 5.00 | mm |
| Min. Clearance to AK | 0.00-0.50 | 0.20 | 0.20 | mm |
| Desired Radial Length | 0.50-2.50 | 2.00 | 2.00 | mm |
| Min. Residual Stroma | 100-300 | 150 | 150 | μm |
| Depth | 20-90 | 80 | 80 | % |
| Entrance Overcut (+) | −0.20-+0.20 | 0.06 | 0.06 | mm |

In an embodiment of these systems, the associated patient support bed is an intelligent patient support bed. This intelligent patient support bed has position determining devices, (e.g., positioning devices, RFID, optical, accelerometers, sensors, location devices, etc.) that are in communication with the laser-ultrasound device to provide the exact location of the patient, and in particular the patient's head, with respect to the laser beam delivery component, the laser beam path, the laser docking component, the ultrasound component, the combined laser-ultrasound device and combinations and variations of these.

In an embodiment of these systems, there is an associated intelligent head rest that can be associated with any standard patient support; e.g., patient support bed. This intelligent head rest has position determining devices, (e.g., positioning devices, RFID, optical, accelerometers, sensors, location devices, etc.) that are in communication with the laser-ultrasound device to provide the exact location of the patient, and in particular the patient's head, with respect to the laser beam delivery component, the laser beam path, the laser docking component, the ultrasound component, the combined laser-ultrasound device and combinations and variations of these.

In an embodiment of these systems, there is an associated patient intelligent device, such as patient tag, band or cap that can be associated with the patient's head or neck, e.g., worn by or placed on the patient. This patient intelligent device has position determining devices, (e.g., positioning devices, RFID, optical, accelerometers, sensors, location devices, etc.) that are in communication with the laser-ultrasound device to provide the exact location of the patient, and in particular the patient's head, with respect to the laser beam delivery component, the laser beam path, the laser docking component, the ultrasound component, the combined laser-ultrasound device and combinations and variations of these.

In embodiments the patient intelligent device can also have network capabilities, storage capabilities, identification capabilities and combinations and variations of these. For example, the patient intelligent device can be used to confirm patient identity, or confirm identity in conjunction with other biometric systems, such are retinal images or iris scans. Moreover, and in this manner, the patient intelligent device can be in communication with the laser systems, medical billing information, electronic patient medical records, and health and information management systems that the surgeon, insurance, the patient, others, and combinations and various of these, require or request.

This position determining device for the patient, which is also referred to as an orientation/position tracking system for the patient, that determines the position of the patient, e.g., the patient's head, with respect to the position of the laser and laser beam path, can be for example, an electromagnetic tracking systems, such as the Polhemus Patriot™ 6-DOF. Embodiments of such tracking systems are disclosed and taught in U.S. Pat. Nos. 5,307,072, 6,369,594, 6,400,139, 6,624,626, 7,710,395, 6,762,600, 7,292,948, 7,873,491 and 8,013,595, the entire disclosure of each of which are incorporated herein by reference. Such devices may also be referred to as a patient locator or patient location device or system.

In an embodiment the laser-ultrasound system, and in particular the laser-phaco system is configured so that the therapeutic laser beam can be delivered in a therapeutic laser beam pattern to one or both eyes of the patient, and a phacoemulsification procedure can be performed on one or both eyes of the patient, without the patient or the surgeon having to move, from their relative positions with respect to the laser-phaco system.

In an embodiment, the size of embodiments of the present devices, e.g., the integrated phaco-laser device, is greatly reduced, compared to the size of the two systems if placed side by side, or merely placed in a common housing or cabinmate, to provide a smaller foot print in the operation room than the total space required for separate laser systems and ultrasound systems. This provides a significant advancement in the art, as before the present inventions, it is believed that a completely integrated laser-ultrasound system has not been used in an operating room or obtained regulatory approval. The reduced size of this embodiment provides several improvements over the art, in efficiency, efficacy and both. The ability to replace two systems, eliminating the need to move patients, systems or both during the treatment of a patient, eliminating the need for patients to be moved from one operating room to another (in the case were the laser system and ultrasound system are in different rooms), are some of the benefits from this smaller sized device embodiment. This smaller sized device embodiment also provides the ability to be used in more, e.g., smaller, operating rooms, with greater ease for the surgeons and other professions working in the operating room to move about. It also can provide advantages in operating clean up, as well as, freeing up space to provide the ability to have other systems in the operating room, such as diagnostic devices and microscopes. The problems associated with integrating the ultrasound and the laser systems into a single device having this small footprint, and small overall volume (height, width, length), without having interference between the devices, maintaining the ability for each device to operation as intended, and maintaining the required efficacy of each device, as well as, the solution to those problems, it is believed, were not identified, addressed or solved by the art prior to embodiments of the present inventions.

In embodiments of these systems the time to change, or switch, from one mode of operation to another preferably occurs quickly. Thus, the device can change from one mode to another, e.g., from laser mode to phacoemulsification mode, in from about 45 sec to about 10 sec, from about 30 sec to about 5 sec, in less than 1 min, in less than 30 sec, in less than 15 sec, in less than 10 sec, in less than 5 sec and in less than 2 sec. It being understood that additional patient preparation time may be needed after the device mode has been changed before a particular procedure may be conducted.

The ability to change between laser and phaco procedures or operations without the patient, the system, the surgeon, and preferably all of these having to be repositioned with respect to each other, provides additional benefits and advantages. For example, this capability to quickly, and unobtrusively, change between femto and phaco configurations or operations, allows the patient to be completely prepped for both procedures before entering the operating room. Further, the patient can even be draped before entering the operating room.

In embodiments of these laser-ultrasound systems, e.g., an integrated phaco-laser device, the device (not including the patient bed), has a floor space volume of less than about 50 cubic feet ($ft^3$), less than about 40 cubic feet ($ft^3$), less than about 35 $ft^3$, less than about 30 $ft^3$, less than about 25 $ft^3$, less than about 200 $ft^3$, about 31 $ft^3$, from about 28 to about 33 $ft^3$, and combinations and variations of these, as well as, larger and smaller values. In embodiments the volume of the device may be adjustable, in which case the volume of the device would be the smallest volume, unless expressly stated otherwise. This device can have a height from about 45 inches (in) to about 75 in, about 65 in, about 60 in, about 50 in, about 55 in, less than 60 in, less than 58 in, from about 52 in to about 58 in, and combinations and variations of these, as well as, larger and smaller sizes. (In embodiments where an arm, extension or component, can be moved to a vertical, or about vertical position, for storage or other purpose, the height should be measured when that component is in an operable configuration or position, e.g., typically horizontal, or about horizontal.) In embodiments the height of the device may be adjustable, in which case the height of the device would be the shortest height, unless expressly stated otherwise. This device can have a length of about 30 in to about 50 in, about 33 in, about 38 in, about 40 in, less than about 45 in, less than 40 in, from about 34 in to about 38 in, about 36 in, and combinations and variations of these, as well as, larger and smaller sizes. In embodiments the length of the device may be adjustable, as by way of, for example, a movable arm assembly, tray or carriage, in which case the length of the device would be the shortest length, unless expressly stated otherwise. This device can have a width of about 15 in to about 40 in, about 20 in, about 25 in, about 30 in, less than about 45 in, less than about 30 in, from about 22 in to about 27 in, about 20 in to about 30 in, and combinations and variations of these, as well as, larger and smaller sizes. In embodiments the width or length of the device may be adjustable, as by way of, for example, a movable arm, assembly, tray or carriage, in which case the width of the device would be the shortest width, unless expressly stated otherwise. Embodiments of these devices can have a device foot print area, i.e., the area of floor space occupied by this device, can be from about 400 $in^2$ to about 1,300 $in^2$, from about 400 $in^2$ to about 600 $in^2$, from about 400 $in^2$ to about 500 $in^2$, from about 450 $in^2$ to about 700 $in^2$, about 450 $in^2$, about 500 $in^2$, about 550 $in^2$, about 600 $in^2$, less than about 1,200 $in^2$, less than about 1,100 $in^2$, less than about 1,000 $in^2$, about 1,000 $in^2$, about 950 $in^2$, about 900 $in^2$, about 800 $in^2$, from about 850 $in^2$ to about 950 $in^2$, and combinations and variations of these, as well as, larger and smaller sizes. In embodiments the width, length and both of the device may be adjustable, as by way of, for example, a movable arm, assembly, tray or carriage, in which case the foot print of the device would be the smallest area, unless expressly stated otherwise. The devices length and width can be the same, e.g., the foot print is in the shape of a square or a circle, or they can be different, e.g., the foot print is in the shape of a rectangle or an ellipse. In being understood that other shapes for the foot print area are envisioned, e.g., star shaped, "L" shaped, "H" shaped, etc.

Typically, a phacoemulsification device has a footprint of about 20 by about 25 in, and thus has a foot print area of about 500 $in^2$ (i.e., the "standard phaco foot print area") Thus, embodiments of the phaco-laser integrated systems can have a foot print area that is about 70% and smaller about, about 80% and smaller, about 90% and smaller, about 100% and smaller, about 110% and smaller, about 120% and smaller, about 130% and smaller, about 140% and smaller, about 150% and smaller, than the typical phaco foot print area of 500 $in^2$. This synergism realized by embodiments of the present inventions, of having two devices, and thus two therapeutic functionalities, in an area that is only slightly larger than one device, provides significant benefits and advantages in the operating room and medical office, for work flow, available rooms for patient care (e.g., smaller rooms can now be utilized), patient and staff comfort, and efficacy, among others.

Further, even in situations where the phacoemulsification system is smaller than the typical foot print, the combined laser-ultrasound systems of the present inventions can be configured to occupy less space than a separate laser and such smaller footprint ultrasound systems.

In embodiments of these systems further synergisms are realized by the use of custom trays, and devices that hold and position various surgical tools, instruments, kits and equipment that are used in the laser therapeutic procedures, laser diagnostic procedures, the phacoemulsification procedures, and lens implantation, as well as in any refractive procedure. These custom surgical trays and kits can be single use disposables that are detachably fixed to the device house (or held by, or in, the device housing), they can be integral trays that hold disposable or reusable tools and instruments, and combinations and variation of these.

In embodiments of these systems the laser procedure is optimized for providing the most efficient, e.g., lowest, phaco energies to remove the particular lens material. Thus, laser parameters such as the femto energy, laser shot spacing, line spacing, etc. and phaco parameters, such as phaco energy, BSS (balanced saline solution) flow, fluidics, can be optimized, and done in highly integrated and predetermined manner, given the integrated control, monitor and storage capabilities of the present systems and devices.

In the embodiments of these systems having dual laser pulse widths, further advantages and benefits would include the ability to reduce the need and use of equipment such as diamond blades and knifes. Thus, reducing costs, risks of infection and the time of the procedure.

It should be understood that the present specification contemplates that embodiments of the present systems can include one or more and all of the features of the foregoing embodiments and paragraphs, in various combinations as one of skill in the art would understand in view of the teachings and disclosure of this specification, as well as, embodiments in the following paragraphs.

Turning to FIG. 1 there is shown a perspective view of an embodiment of a laser-ultrasound system 100. The system 100 is a device that has a first housing 101 and a second housing 102. The housing 101 and 102 contain power components, control components, operating components, analytic prediction and diagnostic devices, position determining and location equipment, laser beam generation components, and ultrasound generation components. In a preferred embodiment the ultrasound generation components are components of a phacoemulsification system and the laser beam generation components provide a laser beam having a pulse length of about 10 ps, 5 ps, 2 ps, and shorter.

These components can be distributed, in whole and in part, between the two housings 101, 102, for among other reasons: to optimize space, to avoid interference between components, to manage heat and vibration, and to provide for more efficient control and operation of the system 100. The two housings 101, 102 can be standalone housings, on the same base or frame 150, they can have communication, control, power, optical and other connections between them, they can be a single same housing, they can be subdivided or partitioned into a third or fourth, etc., housing or sub-housing, and combinations and variations of these.

There is an optical conduit 105 that connects housing 102 with housing 106. Housing 106 contains the scanning devices and beam shaping optics for the therapeutic laser beam, which scanning devices, optics and both, can also be used for monitoring and diagnostic laser beams and optical paths. It being understood that in embodiments these components of housing 106 can be located in whole or in part in one of the other housings 102, 101, and likewise, components from housing 102, 101 can be located in housing 106. Housing 106 could be integral with or a part of the housings 102, 101. Housing 106 can be subdivided or partitioned into one or more housings or sub-housings, and combinations and variations of these. In a presently preferred embodiment housing 106 contains and isolates the scanners and beam shaping optics. The scanner and beam shaping optics, or other components that may be contained in housing 106, are in control communication with the controllers and operating systems of the system 100. By control communication it is meant that information regarding the operation of the devices is transmitted to and from the devices, information obtained or received by the devices is transmitted to and from the devices, and control information, instructions or commands, is transmitted to the devices, and combinations and variations of these, as well as other data and information. The devices may be in direct control communication with each other, or they may be in indirect control communication with each other, such as for example, by being in control communication with a central, e.g., the system 100 controller, the monitor 109, which may also have control capability and combinations and variations of these. These devices may also be in both direct and indirect control communication with each other.

The optical conduit 105 can be a light pipe (e.g., hollow tube or channel having an internally reflective surface so that the laser beam is transmitted through the free space within the hollow tube, the free space within the hollow tube can have a partial vacuum, have air at ambient, contain an inert gas, and combinations and variations of these), an articulated light pipe, a telescoping light pipe, a flexible light pipe, an optical fiber, one or more optical fibers, a hollow conduit, a beam guide and combinations and variations of these and other laser beam conveyance structures.

The housing 106 has an arm 107, which can be moved, extended, contracted and combinations and variations of these, in the direction of arrows 107a, and 107b. The arm 107, and the housing 106 moves in the vertical direction by elevator device 110, as shown by arrow 107a. The arm 107 has an assembly or device 108 for determining the shape and position of the eye and structures within the eye. The arm 107 at its proximal end, i.e., the end furthest along the laser beam path, and thus furthest from the laser beam source, and below the device 108, has a patient interface device (PID) (not shown in this figure). The arm 107 has monitor 109 that moves on an articulated arm in the direction of arrow 109a. The monitor can provide information, such as the procedure, conditions of the system, laser status, ultrasound status, cataract density, ultrasound setting, laser pattern setting, and can receive surgeon input and instructions. The monitor is in control communication with the system 100 control system, the monitor may also contain part or all of the system 100 control system. The monitor is in control communication with the laser control system and the ultrasound control system, either directly, through the system 100 control system, through the monitor 109, and combinations and variations of these. The monitor and its articulated arm may be located on other structures in the system 100 or may be free standing. One, two and additional monitors may be used. The monitors may have 3D viewing or displaying capabilities.

The arm 107 forms or contains a laser beam conveyance structure, such as a hollow tube that provides free space for the transmission of the laser beam. In embodiments the arm 107 may contain a beam path in free space, or optical fibers for transmitting the laser beam to, for example a scanner, that is located at the proximal end of the tube instead of the distal end, i.e., the end near the housing 106. The arm 107 may also be, or contain, any of the laser beam conveyance structures of the types described for use as the optical conduit 105. The tube may also contain optics. In the embodiment of FIG. 1, the arm 107 contains a laser beam that is non-collimated, and thus the arm 107 can be referred to as containing a laser beam and laser beam path that is non-collimated, in other words the arm 107 contains, surrounds or houses "non-collimated space" along the laser beam path. The arm 107 may house or surround collimated space, that is space where the laser beam on the laser beam path is collimated. It may house space that contains optics. It may house both collimated and non-collimated space. The arm 107 in embodiments may pivot from a distal point, rotate, be telescoping, articulated and combinations and variations of these. The proximal end of the laser beam path in the arm 107 contains mirrors or optics to direct the laser beam through the PID and to, and into, the patient's eye.

The system 100 has two ports 103, 104 for connecting cables and lines to ultrasound, aspiration, other tools, and combinations and variations of these. In an embodiment these ports are configured to connect to phacoemulsification tools, or a phaco cassette system. The ports 103 and 104 are shown on the housing 102, it being understood that they could be on the housing 101, or other locations on the system, or could be part of a phaco cassette that has been inserted into the system 100.

In embodiments the laser system has external, internal or both cooling. Such as for example cooling fluid that is flowed into and out of the laser housing.

The system 100 has a height shown by arrow 120, the system has a length shown by arrow 121, and a width shown by arrow 122. The width and length define the foot print area of the system 100, and the volume is defined by the height 120, length 121 and width 122.

Therapeutic Laser and System—Generally

Any laser that is configured to proved a laser beam that is useful, safe and effective for treating the eye, its structures and adjacent tissues, and conditions thereof, can be used to provide a therapeutic laser beam. Tunable lasers, adjustable lasers and combinations and variations of these lasers, can be used, e.g., pulse width can be varied, pulse rate can be varied, power can be varied and wavelength can be varied. More than one therapeutic laser can be used. The therapeutic laser can be a pulsed laser, such as femto second laser or a pico second laser, and longer and shorter pulses, a continuous laser and combinations of these.

The therapeutic laser can have a wavelength in the IR spectrum, the UV spectrum, as well as other wavelengths. The therapeutic laser beams can have wavelengths of from about 300 nm to about 2,500 nm, from about 1,000 nanometers (nm) to about 1,300 nm, 1020 nm, about 1020 nm, 1030 nm, about 1030 nm, 1040 nm, about 1040 nm, 1050 nm, about 1050 nm, and from about 1020 to about 1050 nm, and combinations and variations of these as well as other wavelengths.

The therapeutic laser can have pulse durations of from about 1 fs to about 100 ps, from about 200 fs to about 500 ps, from about 300 fs to about 100 ps, from about 300 fs to about 10 ps, from about 300 fs to about 2,000 fs, and combinations and variation of these durations, as well as longer and shorter durations. The system can have one or more "short pulse duration" therapeutic lasers having pulse widths of 300 fs, about 300 fs, 350 fs, about 350 fs, 400 fs, about 450 fs, 500 fs, about 500 fs, from about 300 fs to about 600 fs and combinations and variations of these. The system can have one or more "long pulse duration" therapeutic lasers having pulse durations of 1000 fs, about 1000 fs, 1200 fs, about 1,200 fs, 1,300 fs, about 1,300 fs, 1,500 fs, about 1,500 fs, from about 1,200 fs to about 1,600 fs and combinations and variations of these.

These dual beam embodiments, i.e., having at least both short pulse duration and long pulse duration therapeutic laser beams have several advantages and benefits that would include, for example, the ability to reduce the need and use of equipment such as diamond blades and knifes. Thus, reducing costs, risks of infection and the time of the procedure.

The therapeutic laser beams can have pulse repetition rates of from about 50 kilohertz (kHz) to about 5 megahertz (Mhz), from about 50 kHz to bout 2 Mhz, from about 50 kHz to about 1 Mhz, from about 50 kHz to about 750 kHz, from about 100 kHz to about 200 kHz, from about 150 kHz to about 350 kHz, about 100 kHz, about 150 kHz, about 200 kHz, about 300 kHz and variations and combinations of these and greater and smaller rates.

The therapeutic laser beams can average output power at a specified pulse repetition rate of from about 1 Watt (W) to about 8 W, from about 2.5 W to about 5 W, from about 3 W to about 4.5 W, from 3 W to 5 W, less than 6 W, less than 5 W, any power where laser induced optical breakdown (LIOB), photodisruption or both occurs and combinations and variations of these, and lower and higher powers.

Embodiments of these system also can perform subthreshold treatments, diagnostics and combinations and variations of these. Thus, the therapeutic laser beam can be delivered to the eye at a power, or in a manner, that is below the point where LIOB would occur. The therapeutic laser beam can be delivered to the eye at a power or in a manner where the power is below the point where photodisruption occurs. Thus, in an embodiment of the present procedures, a sub-threshold laser procedure can be performed, a laser procedure that induces photodisruption can be performed and a phacoemulsification can be performed, and combinations and variations of some or all of these procedures, can be performed without moving the location of the patient or the device.

The therapeutic laser beams can have a pulse energy of from about 1 nanojoule (nJ) to about 2 millijoule (mJ), from about 1 nJ to about 1 mJ, from about 2 microjoules (µJ) to about 70 µJ, from about 5 µJ to about 45 µJ, from about 2 µJ to about 35 µJ, from about 10 µJ to about 30 µJ, less than 45 µJ, less than 35 µJ, any pulse energy where photodisruption, LIOB or both occurs, and combinations and variations of these, and lower and higher energies.

The therapeutic laser beams of the present systems can have one or more of the above beam features, e.g., wavelength, duration, repetition rate, power, and pulse energy, and combinations and variations of these.

A Yb:YAG laser that generates ultrashort laser pulses in the 1030 nm wavelength can be used as a therapeutic laser. In general, the therapeutic laser provides a beam that is of a wavelength that transmits through the cornea, aqueous and lens. The beam can be of a short pulse length, together with the energy and beam size, to produce photodisruption, LIOB or both of the targeted ocular tissue, e.g., cornea, limbus, lens capsule, lens, cataractous tissue, opacified tissue, and other tissue. Thus, as used herein, the term laser shot or shot refers to a laser beam pulse delivered to a location that by itself or in combination with other pulses results in a therapeutic effect, e.g., LIOB. As used herein, the term photodisruption essentially refers to the conversion of matter to a gas by the laser. In embodiments, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 kHz to several GHz. Generally, lower pulse rates correspond to higher pulse energy in commercial laser devices. A wide variety of laser types may be used to have a therapeutic effect, e.g., cause photodisruption, LIOB or both of ocular tissues, dependent upon pulse length and energy density, as well as other factors. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) µjewel D series D-400-HR, which is a Yb:fiber oscillator/amplifier having a wavelength of 1045 nm, less than a 1 picosecond pulse width, about 5 MHz PRF, with 100 nanojoules; the Coherent Staccato, which is a YB:Yag having a wavelength of 1030 nm, about 1.5 picosecond pulse width, about 80 KHz PRF, with 30 microjoules; and, the Coherent Rapid, which is a YB:Yag having a wavelength of 1030 nm, about 1.5 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) pJewel D series D-400-NC, which is a Yb:fiber oscillator/amplifier having a wavelength of 1045 nm, less than a 100 picosecond pulse width, about 200 KHz PRF, with 4 microjoules. These and other similar lasers may be used a therapeutic laser and to generate therapeutic laser beams.

Embodiments of laser systems, methods and apparatus for performing laser operations on the eye are disclosed and taught in US patent application Publication Nos. 2016/0302971, 2015/0105759, 2014/0378955, and U.S. Pat. Nos. 8,262,646 and 8,708,491, the entire disclosures of each of which are incorporated herein by reference.

Laser Beam Delivery—Generally

In general, embodiments of the optics for delivering the therapeutic laser beam to the natural lens of the eye should be capable of providing a series of shots to the natural lens in a precise and predetermined pattern in the x, y and z dimension. The optics should also provide a predetermined beam spot size to cause photodisruption, LIOB or both with the laser energy reaching the natural lens or other targeted tissue. Thus, the optics may include, without limitation: an x y scanner; a z focusing device; and, focusing optics. The focusing optics may be conventional focusing optics, flat field optics, telocentric optics, and combinations and variations of these, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the ACRES Rhino Scanner. Examples of such z focusing devices would be the Phsyik International Peizo focus unit Model ESee Z focus control and the SCANLAB varrioSCAN.

Laser Control System—Generally

In general, embodiments of the control system for delivering the therapeutic laser beam may be any computer, controller, software hardware and combinations and variations of these that is capable of selecting and controlling x y z scanning parameters and laser firing, among other things. These components may typically be associated at least in part with circuit boards that interface to the x y scanner, the z focusing device, the laser and combinations and variations of these. Among other things, the laser control system may contain the programs that direct the laser through one or more laser shot patterns. The laser control system also, has the further capabilities of integrating with the system control system, and function with, or otherwise working as an integrated system with the ultrasonic control, and the monitor or control panel. The system controller, the laser controller, the ultrasound controller and combinations and variations of these can also control other components of the system, as well as, maintaining data, obtaining data, analyzing data and images, preparing and suggesting table and treatments, and performing calculations. The control system may contain the programs that direct the laser through one or more laser shot patterns.

Position and Shape Determination—Generally

In general, in embodiments, the assembly or device for determining the shape and position of the eye and structures within the eye can be an optical coherence tomography (OCT), a Scheimpflug device having a single moveable camera, multiple fixed cameras, combinations and variations of these, and other types of devices for making such determinations. This device, in embodiments, determined the relative distance of portions of the lens, or other structures of the eye or tissue adjacent to the eye, from the laser, for example the optics head. In embodiments, this distance is maintained constant by for example the PID. In embodiments, this device determines the position of the lens and other structures, with respect to the scanning coordinates for the laser delivery pattern in all three dimensions. This may be accomplished by several methods and apparatus. For example, x y centration of the lens may be accomplished by observing the lens through a co-bore sighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor, the Aculux Laser Ranger LR2-22 and combinations and variations of these. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera or cameras, which can view a reference and the natural lens, and would also include a light source to illuminate the natural lens. Such light source could be a structured light source, such as for example a slit illumination designed to generate 3-dimensional information based upon geometry. Further one, two, three, four or more, light sources can be positioned around the eye and the electronically activated to provide multiple views, planar images, of the eye, and in particular the cornea and the lens, at multiple planar slices that can then be integrated to provide data for position and location information relative to the laser system about those structures. Examples of assemblies, methods, devices for determining the shape and position of the eye and structures, with respect to the laser, laser shot pattern, and laser beam, are disclosed and taught in US patent publications and patents numbers 2018/0085256, 2016/0302971, 2015/0105759, 2012/0330290, 2016/0030244, U.S. Pat. Nos. 9,180,051 and 8,708,491, the entire disclosure of each of which is incorporated herein by reference. Iris registration devices for determining the position of the eye are taught and disclosed in US patent publication number 2015/0105759, the entire disclosure of which is incorporated herein by reference. Generally, images (optical images) travel back from the structure of the eye, the PID, or other structures, to the device or system along an optical path, e.g., along an image path, which can be through free space, optical components (lens, mirrors, fibers etc.) and both.

Patient Interface—Generally

A further component of embodiments of these systems can be the laser patient interface or PID. It is noted that all or some of the PID is typically not a part of the system, but is preferably a single use device, (e.g., a disposable) that is added to the system for each patient prior to, or as set up for, a laser procedure. In embodiments, this interface provides that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that can be circular or elliptical that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics, some structure that is of known distance from the laser along the path of the laser beam and fixed with respect to the laser, and combinations and variations of these. Examples of patient interfaces devices, and system to engage the PID with the eye, and systems to engage the PID with the laser system, are disclosed and taught in US Patent Application Publication Nos. 2011/0190739, 2017/0290703, 2010/0022994, 2011/0022035 and 2015/0088175, the entire disclosures of each of which are incorporated herein by reference.

During testing and calibration, a laser beam, and preferably the therapeutic laser beam can be transmitted through the window of the PID.

Ultrasound/Phacoemulsification—Generally

Any ultrasonic generator, e.g., ultrasonic driver, horn or other device to create ultrasonic energy, that is configured to provide ultrasonic energy that is useful, safe and effective for treating the eye, its structures and adjacent tissues, and conditions thereof, can be used to provide the ultrasonic energy for the present systems. In particular, some or all of the comports of any, preferably approved by a medical device regulatory body, phacoemulsification system can be used, or reconfigured for use, in embodiments of the present systems.

Generally, in embodiments of the present integrated systems, and the methods they can perform, phacoemulsification includes making a corneal scleral incision (and combinations and variations of these) preferably with the therapeutic laser beam, and the insertion of a phacoemulsification handpiece, which is typically comprised of a needle that is ultrasonically driven, in order to, for example, emulsify, i.e., to liquefy, the natural crystalline lens, break a cataract into small pieces, and combinations and variations of these. Preferably, this ultrasonic procedure is performed on a lens, lens material, cataractous material, that has been cut, sectioned, softened and combinations and variations of these, by the laser beam. The emulsified pieces may subsequently be removed using the same handpiece or another handpiece. The surgeon may then insert implants, e.g., interocular lens, IOLs, in the eye through the incision.

In embodiments, the phaco frequency of the vibration of the tip of the phaco needle can be greater than 20 kHz, greater than 30 kHz, greater than 40 kHz, from about 30 kHz to about 50 kHz, from about 30 kHz to about 45 kHz, less than about 50 kHz, from about 35 kHz to about 45 kHz, about 35 kHz, about 40 kHz, about 45 kHz, 35 kHz 40 kHz, 45 kHz, and combinations and variations of these, as well as, higher and lower frequencies.

In embodiments, the length of the stroke, longitudinal movement, of the phaco needle can be from about 28.1 µm to about 95.25 µm, from about 25 µm to about 160 µm, from about 50 µm to about 90 µm, from about 50 µm to about 150 µm, from about 25 µm to about 110 µm, from about 35 µm to about 100 µm, from about 20 µm to about 60 µm, from about 80 µm to about 150 µm, and combinations and variations of these, as well as, larger and smaller distances.

Generally, phaco systems can have pulse rates from about 20 pulses per second to about 150 pulses per second, and combinations and variations of these, as well as, higher and lower values. And, these systems can have burst widths from about 30 milliseconds to about 4 milliseconds and combinations and variations of these, as well as, higher and lower values.

In embodiments of the present systems, the phacoemulsification handpiece is generally coupled to an irrigation source and an aspiration pump. The aspiration pump is located a housing in the system. The handpiece includes a tip for insertion within the anterior chamber of the patient's eye that emits the ultrasonic energy, or vibrates at ultrasonic frequencies, to cut, to emulsify, and combinations and variations of these, the crystalline or natural lens. The handpiece further includes an irrigation port distal to the tip, which is coupled to an irrigation source via an irrigation line, and an aspiration port at the tip, which is coupled to an aspiration pump via an aspiration line. Fluid from the irrigation source, which is typically an elevated bottle of saline solution, is irrigated into the eye via the irrigation line and the irrigation port, and the irrigation fluid and emulsified crystalline lens material are aspirated from the eye by the aspiration pump via the aspiration port and the aspiration line.

Other medical techniques for the eye that an ultrasound system may be configured to perform also typically include emulsifying, irrigating the eye and aspirating. Such procedures may or may not include the destruction, alteration or removal of features of the natural eye using the emulsification, irrigation and aspiration. Thus, the ultrasonic power delivered by the surgical console, and the flow of fluid to and from a patient through the irrigation or aspiration console, and the consequent need to control the phacoemulsification handpiece to deliver the foregoing, is selected and controlled by the system, by the surgeon, and by combinations and variations of these.

Phacoemulsification components, e.g., subassemblies, of embodiments of the present systems typically include a control system, e.g., a programmable microprocessor, a console with operator-selected presets for controlling, which in embodiments is the system monitor, for example, aspiration rate, vacuum and ultrasonic power levels. The phacoemulsification handpiece may be interconnected with the system by an electric cable for powering and controlling the piezoelectric transducer that provides the emulsification. Tubing provides the irrigation fluid to the eye, and enables withdrawal of aspiration fluid from an eye, through the handpiece under the control of the console.

In embodiments, phase angles and other aspects associated with handpiece operation are determined and measured at all times during operation of the handpiece, such as to adjust the driving circuitry, achieve an optimum phase angle, and otherwise effect energy transfer into the tissue from the phacoemulsification handpiece. Automatic tuning of the handpiece may be provided by monitoring the handpiece electrical signals and adjusting the frequency and other aspects to maintain consistency with selected parameters.

In embodiments, the control systems address the requirements of power control for the phacoemulsification handpiece based on the phase angle between voltage applied to a handpiece piezoelectric transducer and the current drawn by the piezoelectric transducer, the amplitude of power pulses provided to the handpiece, and both of these. The typical arrangement may be tuned for the particular handpiece, and, for example, power may be applied in a continuous fashion or in a series of solid bursts subject to the control of the surgeon. For example, the system may apply power for 150 ms, then cease power for 350 ms, and may repeat this on/off sequence for the necessary duration of power application. Application of power during the aforementioned 150 ms period may be defined as a constant application of a 25 kHz to 50 kHz sinusoid. In certain circumstances, the surgeon or operator may apply the power bursts for a duration of time, then cease application of power, then reapply at the initial or another power setting. The frequency and duration of the burst is typically controllable, as is the length of the stream of bursts applied to the affected area. The time period where power is not applied may enable periods in which broken sections may be removed using aspiration, such as may be provided by the handpiece or a secondary aspiration apparatus.

In embodiments of the present systems the control method for the ultrasonic power delivery can generally be in several modes, e.g., variable, predetermined variable, panel and linear. Variable mode provides the surgeon or operator the greatest flexibility for selecting the conditions of the ultrasonic therapy, it could be viewed as manual. Predetermined variable mode is the mode where the control system determines optimum ranges for the ultrasonic therapy, based upon the laser therapy provided, the grade of the cataract, and other information obtained by the system prior to, during and after the laser therapeutic procedure. Thus, in this mode the system, working in conjunction with the laser controller system, and the phacoemulsification control system, predetermines, and makes available, recommends and preferably optimizes ranges, and settings for the phacoemulsification procedure. Generally, the panel mode typically provides strict, fixed values upon user selection. Generally, the linear mode allows only the simplest form of linear adjustment from 0% to 100%, In embodiments, intermediate adjustments, or adjustments outside of system recommended options or ranges for delivery of the ultrasonic therapy are not made freely available, e.g., they are restricted, hi part hi order to minimize the need for and risk inherent in manual adjustment.

The phacoemulsification ultrasound probe delivers energy into the eye that is used to break up the remaining cataractous lens material after laser fragmentation or cutting, to facilitate emulsification and aspiration of the remaining pieces. The phacoemulsification ultrasound probe delivers energy into the eye that is used to break up a cataract where no laser fragmentation of the cataract has been performed, for example where the surgeon elects to perform a laser capsulotomy and laser incision for insertion of the phacoemulsification probe, but does not use the laser to fragment the lens or cataract. The phacoemulsification ultrasound probe delivers energy into the eye that is used to break up the cataract accomplishes this by vibrating at a fixed frequency when the control switch, e.g., a foot pedal is depressed to predetermined position, the same control switch can control the firing or delivery of the therapeutic laser beam and pattern, other types of control switches, buttons, triggers, audio, etc. can be used. In embodiments, to increase the amount of ultrasound power, the machine increases the stroke length of the probe.

Generally, the probe can deliver power in a longitudinal manner, in a lateral manner, and in combinations and variation of these. In the longitudinal manner the phaco needle moves forward and back. In the latter manner the ultrasound power is also delivered through lateral motion of the probe and can increase cutting efficiency, for example, by reducing repulsion of lens material.

In general, there are two types of lateral motion in phacoemulsification. Torsional lateral motion, in which the phaco tip oscillates in a rotational manner along its primary axis. Transversal lateral motion, in which the phaco tip moves in an elliptical path. Generally, based upon their types of motion, torsional typically works better with an angled phaco needle while transversal typically works equally well with either a straight or angled needle. Combining lateral motion phaco with traditional longitudinal phacoemulsification can aid cutting efficiency, since the cataract material is emulsified in more than one direction.

Although the art describes phacoemulsification as delivering ultrasound energy, it is understood that it is the stroke of the phaco needle that creates a mechanical impact as the metal phaco needle hits the target material, e.g., laser effected cataract material. Typically, the needle also creates cavitation and implosion as a microvoid is created just in front of the phaco needle. A fluid and particle wave is propagated into the cataract material and finally, heat is created as a by-product. It is important to avoid choosing phaco power settings that cause excessive heat build-up as this can burn the cornea and damage the delicate ocular structures. Unrestricted flow through the surrounding irrigating sleeve is also very important, as the constant cooling effect of balanced salt solution moving around the phaco probe helps to prevent heat build-up.

In embodiments of the present system, during surgery, the system controller, the phaco controller, and combinations and variations of these, can monitor, record and analyze the average phaco power, given as a percentage of maximum, as well as the total time during which phaco ultrasonic power was delivered, as well as other conditions and factors. In embodiments the common monitor can display these values as "U/S AVE," which stands for "ultrasound average," and "EPT," which is "elapsed phaco time", as well as, other parameters and features. The total energy delivered into the eye is the product of the phaco power multiplied by the time the power is on, known as the absolute phaco time (APT). The system controller, the phaco controller, and combinations and variations of these can automatically calculate the APT by multiplying the "U/S AVE" by the "EPT," so that the surgeon can compare the total ultrasonic energy delivered in different cases.

In embodiments, to decrease the APT maximally, the surgeon needs to decrease the phaco time, the average phaco power and combinations and variations of these. The average phaco power can be decreased by selecting a parameter on the monitor, or through limiting the position of the control switch, or by decreasing the maximum phaco power level on the machine. The phaco time can be decreased by applying the ultrasonic power only when cataract pieces are at the phaco tip and vacuum alone is insufficient to aspirate the piece. Additionally, phaco time can be reduced by delivering shorter pulses or bursts of phaco power instead of continuous ultrasound power or by decreasing the duty cycle (the ratio of the on:off pulses). This method of breaking up the ultrasonic power into smaller packets of pulses and bursts is called phaco power modulation.

In embodiments the basic power settings can be continuous, pulse, and burst. In the continuous power setting, energy delivery is continuous with variations in power, controlled by the control switch position, e.g., the amount of foot pedal depression.

In embodiments, the system provides for combinations and variations of these, as well as, for power setting that provide hybrid or mixed levels of these power modes, as the variations in power can be more accurately determined and provided in a predetermined manner by the control system working in conjunction with the phaco control system, and in situations also with the surgeons input.

In embodiments, in the pulse mode, the pulse power increases linearly by the position of the control switch, e.g., how far down the foot pedal is depressed. The farther it is positioned, e.g., depressed, the greater the power will be of each sequential pulse of energy. A feature of embodiments of a pulse mode operation is that after each pulse of energy delivered, there is a period of time in which no energy is delivered between increasing pulses of energy, the "off" period. Alternating between equal "on" and "off" pulse times reduces heat and delivers half the energy into the eye.

In embodiments, in the burst mode, each burst has the same power but the interval between each burst decreases as the control switch is advanced, e.g., the foot pedal is depressed. In embodiments, the farther the control switch is advanced, e.g., the foot pedal is depressed, the shorter the "off" period will be between each burst. Thus, in embodiments at the maximum control switch position, e,g., at maximum foot pedal depression, the bursts of energy become continuous delivery of energy.

In embodiments burst mode can provide phaco-assisted aspiration of the lens nucleus. The surgeon uses the vacuum and fluidics of the phaco machine to aspirate the cataract and then gives small bursts of phaco power only when necessary. Because one, preferably the control system, can program or recommend these bursts of phaco power to be very short (as quick as a few milliseconds), there can effectively be delivered hundreds of tiny bursts and still less than for example 1 second of total phaco time.

The present systems, provide embodiments where the range of programmability of the pulse and burst phacoemulsification settings, as well as other settings, has the same features as prior systems, and in embodiments is greatly expanded over prior systems. Embodiments of the present systems, unlike any prior system, provide the ability to have predetermined and recommend phaco settings based upon the laser systems delivered laser pattern or therapy, and to provide those setting instantly with no need for either the surgeon or the patient to move.

In embodiments, the phaco control system, alone or in combination with the system control system can perform various active monitoring and control functions such as: monitoring intraocular pressure (IOP) and can adjust the function of the system to maintain the IOP at the desired pressure; monitoring and controlling vacuum levels; optimizing power settings; and predicting pressure changes and proactively responding to occlusion breaks. The sensors to provide this information and data for the monitoring and autonomous control of the phaco system operating parameters can be in the system, on the various pumps and devices, based upon current or other electrical load, or in or on the hand piece.

An example of the performance features, and components that can be used, in the present phaco-laser systems is the Alcon CENTURION® Vision System and the Alco ACTIVE SENTRY® Handpiece and INTREPID® Hybrid Tip. In embodiments, the phaco handpiece can have a built-in fluidics pressure sensor that detects pressure in real time and communicates with the systems control system, the phocosystem control system or both. An example of the various features, and components that can be used, in the present phaco-laser systems is the AMO WHITESTAR SIGNATURE® PRO Phacoemulsification System.

Features, methods of using, and components of, phaco systems and subsystems are disclosed and taught in U.S. Pat. Nos. 8,020,565, 9,549,850, 9,549,851, 9,849,030, 9,877,865, 9,931,447, 9,937,077, 10,258,505, 10,314,953, 10,111,990, and US Published Patent Applications Nos. 2019/0133824, 2019/0021906, 2019/0099526, 2017/0266046, and 2017/0112668, the entire disclosures of each of which are incorporated herein by reference.

Ultrasound-Laser Combinations—Generally

These embodiments include any combined laser-ultrasound system, and in particular, include a combined phacoemulsification laser systems, and a combined phacoemulsification femtosecond laser systems ("femto-phaco" or "phaco-femto", which unless specifically stated otherwise are used interchangeably). These embodiments can have or utilize one or more of the embodiments, features, functions, parameters, components, or systems of the Therapeutic Laser and System, Laser Beam Delivery, Laser Control System, Position and Shape Determination, Patient Interface, and Ultrasound/Phacoemulsification, General teachings disclosed in this specification, as well as, one or more of the features of the systems in the Examples.

In a preferred embodiment of the laser-ultrasound system, and in particular a laser-phaco system, and more in particular a femto-phaco system, the system has two therapeutic laser beams, which can be provided by the same or different laser sources, one a short pulse duration laser beam and the second a long pulse duration laser beam.

Generally, the short pulse duration laser is for performing procedures on the cornea, e.g., cutting the cornea, limbal relaxing incisions, etc. Generally, the long pulse duration laser beam is for performing procedures on the lens, e.g., capsulotomy, lens fragmentation, cataract fragmentation, etc.

These embodiments having multiple types of different therapeutic laser beams, e.g., a short pulse duration and long pulse duration, can have or utilize one or more of the embodiments, features, functions, parameters, components, or systems of the Therapeutic Laser and System, Laser Beam Delivery, Laser Control System, Position and Shape Determination, Patient Interface, and Ultrasound/Phacoemulsification General teachings disclosed in this specification, as well as, one or more of the features of the systems in the Examples.

Systems, e.g., femto-phaco systems, can have multiple therapeutic laser beams, e.g., 1, 2, 3, 4 or more, beams having different properties. These laser beams can follow the same laser beam path and thus travel through and interact with the same optical components, they can travel through different laser beam paths and thus travel through and interact with different optical components, and combinations and variations of these. For example, the system can have a first beam having a first pulse duration and a first power or energy, a second beam having a second pulse duration and second power or energy, and a third beam having a third pulse duration and third power or energy. The first, second and third, pulse durations, first, second and third powers, and first, second and third energies, can be the same, different and combinations and variations of these.

In an embodiment the multiple therapeutic laser beam laser system is associated with (either integral or modular) with another therapeutic device, e.g., an ultrasound device, a diagnostic device, and combinations and variations of these.

In an embodiment where the long pulse duration and short pulse duration laser beams are provided by the same therapeutic laser source, the time to switch between the pulse lengths is less than about 3 seconds (sec), less than about 2 sec, less than about 1.5 sec, from about 3 sec to 1 sec, about 2 sec, about 3 sec, and combinations and variations of these, as well as longer and shorter times.

Although, the preferred embodiments of the present inventions are directed to laser-ultrasound, and in particular Femto-phaco systems, it is understood that the present improvements to, and embodiments of laser systems, find value, and can be used alone, without being a part of a laser-ultrasound system.

Embodiments of these present systems provide an important advantage over the prior art. Because the present systems can provide the optimum laser energy pattern, permit the evaluation of the eye, after that delivery, and then without moving the patient, and then with minimal time delay (less than 1 min, less than 30 sec., less than 15 sec.) perform the phaco procedure, the important goal of using as little ultrasonic phaco energy as possible during the cataract surgery can be accomplished, and preferably accomplished in a predetermined manner for all patients.

EXAMPLES

The following examples are provided to illustrate various embodiments of systems, components of the systems, processes, compositions, applications and materials of the present inventions. These examples are for illustrative purposes, may be prophetic, and should not be viewed as limiting, and do not otherwise limit, the scope of the present inventions.

The embodiments of these Examples 1 to 46 can have or utilize one or more of the embodiments, processes, methods, features, functions, parameters, components, or systems of the Therapeutic Laser and System, Laser Beam Delivery, Laser Control System, Position and Shape Determination, Patient Interface, Ultrasound/Phacoemulsification, and Phaco-Femto Combinations General teachings disclosed in this specification, and combinations and variations of each of these; as well as, one or more of the embodiments, processes, methods, features, functions, parameters, components, or systems provided in one or more of the other Examples and other embodiments provided in this specification.

Example 1

Figure 2:
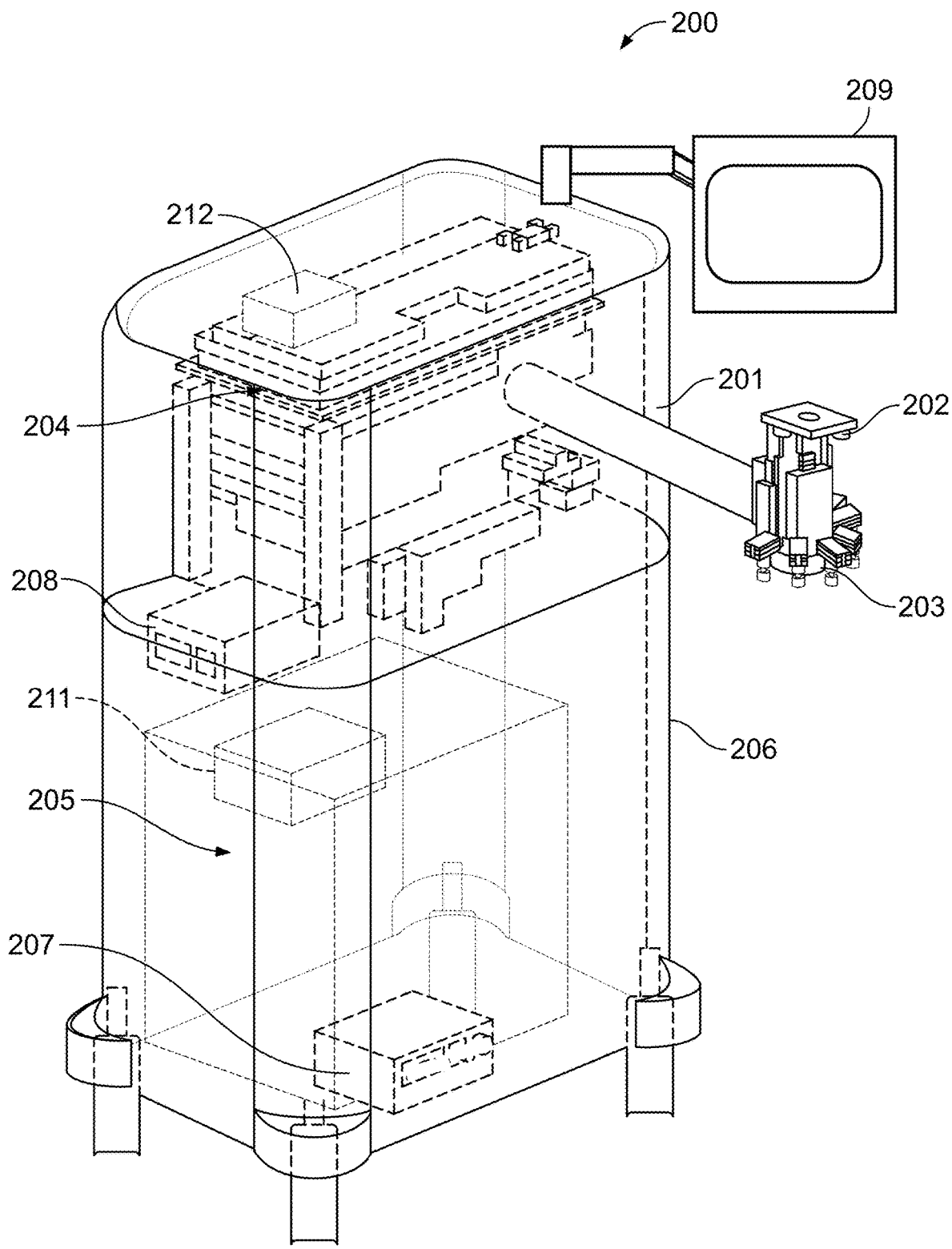
FIG. 2 is a perspective view of an embodiment of a femto-phaco system, in accordance with the present inventions.

Turning to FIG. 2 there is shown a perspective, partial cutaway view of an embodiment of a femto-phaco laser system 200. The system 200 has a laser subsystem 204 and a phacoemulsification subsystem 205 that are contained within a common housing 206. The laser subsystem 204 includes a therapeutic laser beam source, and in embodiments a slow pulse duration and long pulse duration therapeutic laser beam source. The laser subsystem 204 includes a laser that defines a therapeutic laser beam path that the therapeutic laser beam travels along and optical components that are positioned or located along the laser beam path. These components would include z-direction focusing optics, and an x-y scanner.

The system 200 has an arm 201 that houses the therapeutic laser beam path, as well as other optical paths. In embodiments the arm 201 also houses or carries control and power cables for the imaging and position apparatus 203, and the docking assembly (not shown in this figure). The arm 201 has at its proximal end a therapeutic laser beam delivery head 202. The laser delivery head 202 has a position and shape deterring apparatus, which can be an OCT system, or the Scheimpflug systems of the present examples, and combinations and variations of these and other shape and position determining apparatus. The laser delivery head has a docking and positioning system that in conjunction with a PID docks to the patient's eye.

The system 200 has a common power supply 207 for the laser subsystem 204, and the phaco subsystem 205. The common power supply 207 provides all power for the entire system, eliminating the need for secondary power supplies, or sources of power. This permits the system to plugged into a single power supply in the operating room.

The system 200 has a common control system 208. The common control system 208 has a controller operating control software or operating instructions. In a preferred embodiment the common control system 208 is in control communication with one or more of and preferably all of: a control system and controller 212 in the laser subsystem; a control system and controller 211 in the phaco subsystem; in control communication with the operator interface 209; in control communication with the emergency stop 210; and in communication with a network that is for example a patient medical record system, an accounting system, and combinations and variations of these configurations.

Typically, the docking system, and imaging and position determining apparatus are controlled by the laser subsystem control system. In embodiments they may in whole or in part be controlled directly by the common control system 208.

In an embodiment the laser control system and the phaco control system are partially, and can be fully integrated into a single common control system. Thus, in an embodiment only one control system, or a single control system is present in the femto-phaco system.

Example 2

Figure 3:
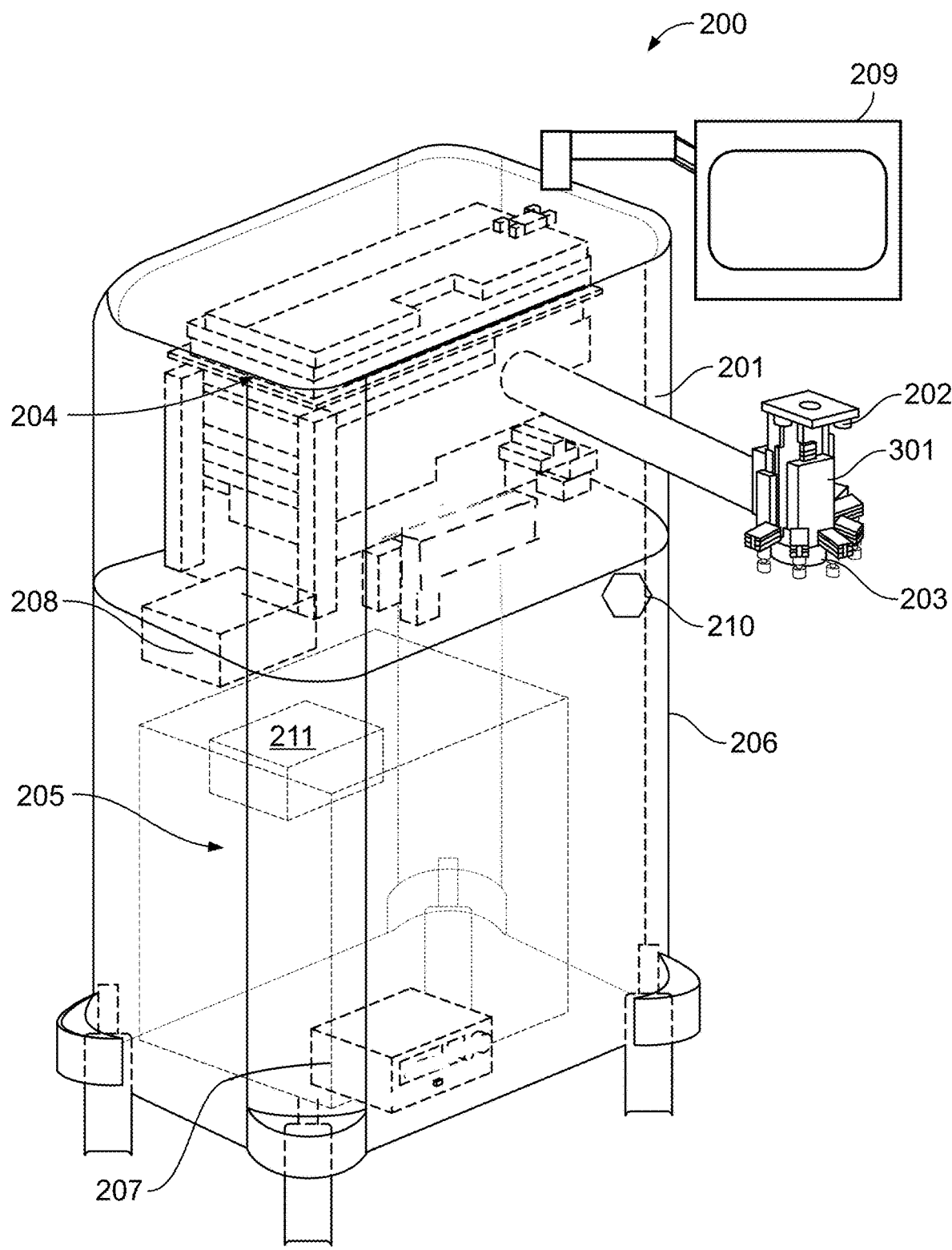
FIG. 3 is a perspective view of an embodiment of a femto-phaco system, in accordance with the present inventions.

Turning to FIG. 3, there is shown an embodiment of a femto-phaco system along the lines of Example 1, like numbers indicating like components. In the embodiment of FIG. 3 the x-y scanner 301, is located in the laser delivery head 202.

Example 3

Turning to FIGS. 4, and 4A to 4D there are shown schematics of the optical paths and optical configurations for embodiments of the present laser systems, laser-ultrasound systems, and in particular femto-phaco systems.

The optical system 430 has four optical systems, 400, 401, 402, 403, which may have light of different wavelengths, powers and for different purposes. Optical system 400 is for the therapeutic laser beam and contains optical components and defines a therapeutic laser beam path along which the therapeutic laser beam travels. Optical system 403 is for the image and position determining apparatus, e.g., Scheimpflug device, which determines among other things, the shape and location of structures of the eye, and does so in direct relationship to the therapeutic laser beam and laser beam path. This system 403 provides an image path. Optical system 401 is for a camera, preferably an IR camera, as can be seen from the drawing this beam path travels along, i.e., is coincident with, the therapeutic laser beam path 400 for the majority of that path. This system 401 provides an image path. The two paths are combined at a beam splitter, and the Vario (Z-Axis laser deflection optic) for the therapeutic laser is not a part of the camera beam path 401. Optical system 402 is for a second camera, preferably a color camera. This system 402 shares some of therapeutic laser beam path. This system 402 provides an image path.

These systems also have an IR DTP ("Down The Pipe", e.g., configured for viewing along the laser beam path)

camera 480, beam splitter cubes 481, 482 (R: 880 (S); T: 880 (P), 1030 (S+P)), galvo mirrors 483, a DTP relay 491, a vario 484, a 1× telescope 485, an F-theta lens 486, a color DTP camera 487, a beam splitter cube 489 (R: 880, 1030; T: visible) and a Scheimpflug camera assembly 490.

The telescope 485 has a pair of telocentric 120 mm lenses 493, 494. The Scheimpflug camera assembly 490 has an image plane 470 with a tilt angle of 15 degrees, a Thorlabs lens (30 mm) 471, an aperture stop (4.4 mm) 472, and a fold mirror 473. The IR DTP Camera 480 has an aperture stop (3 mm) 450. The Color DTP camera 487 has an aperture stop (2 mm) 451.

Figure 4:
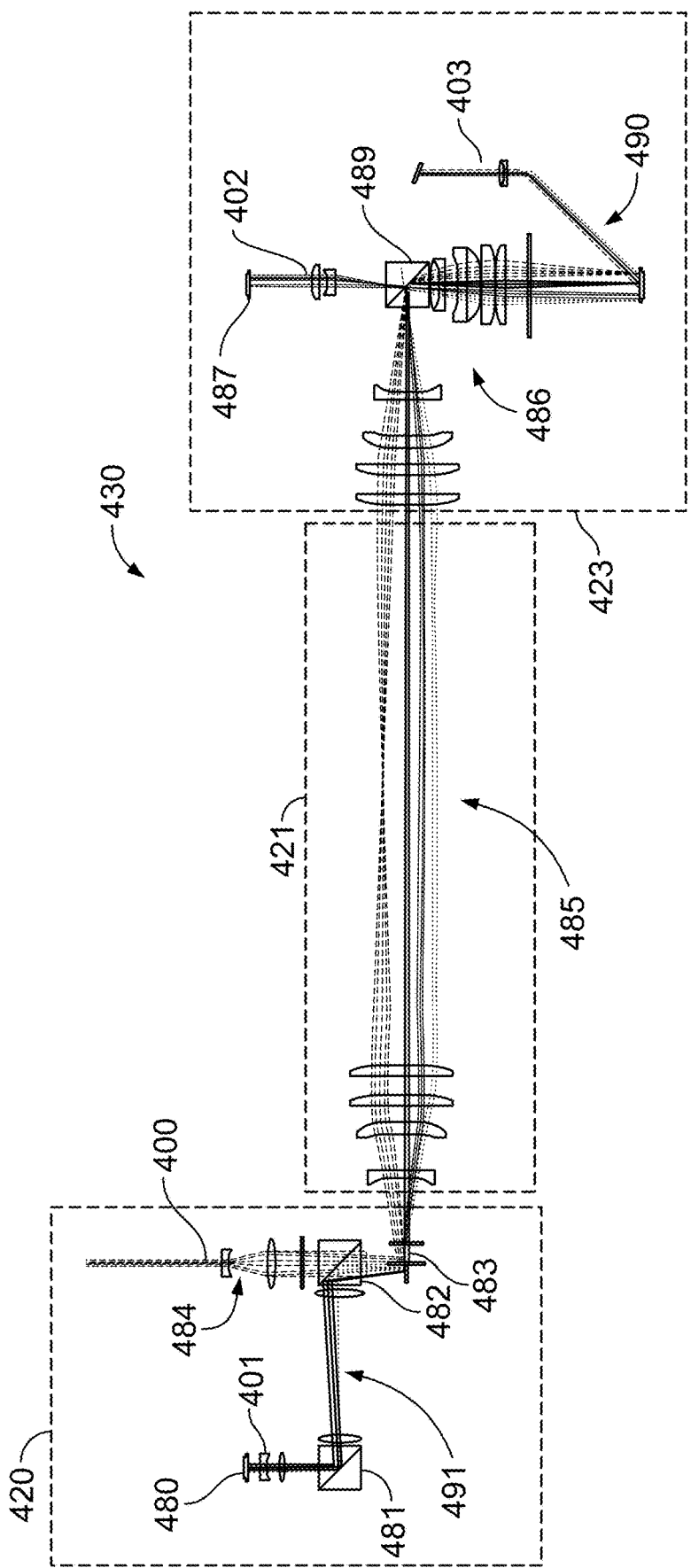
FIG. 4 is a schematic of an embodiment of the optical systems and optical paths for a femto second laser system, and an embodiment of a femto-phaco system, in accordance with the present inventions.
Figure 4A:
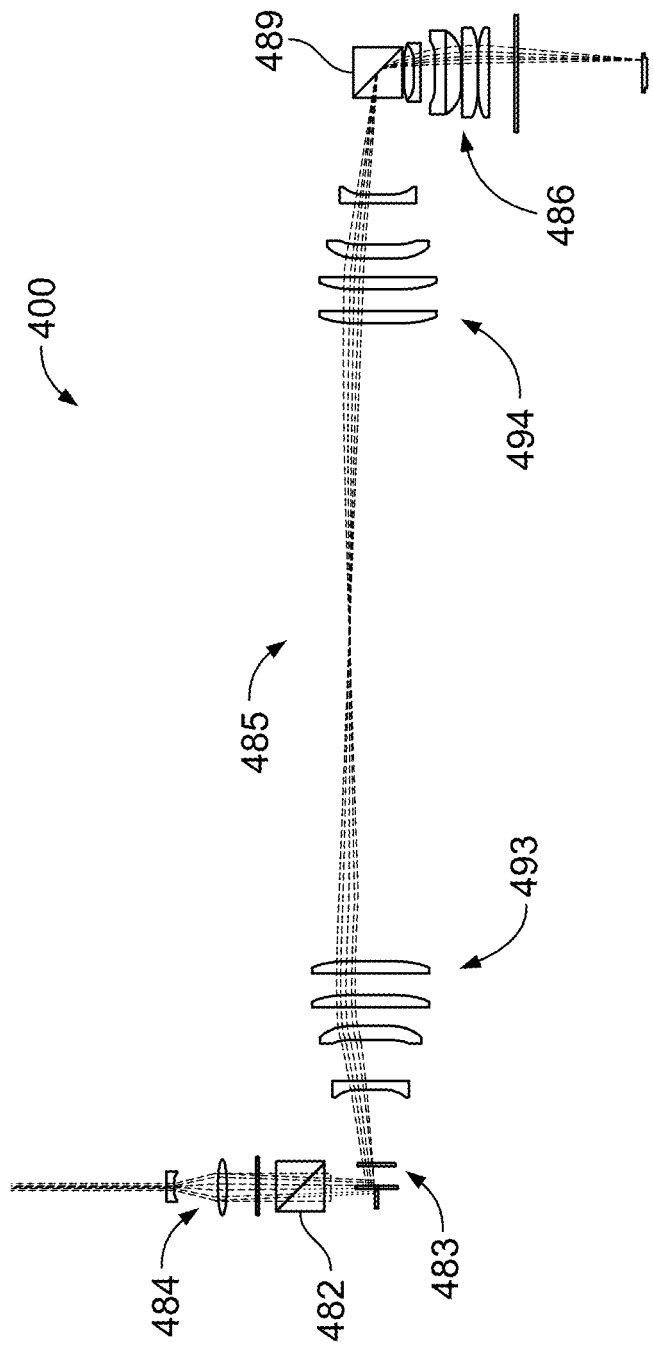
FIG. 4A is a schematic of an embodiment of the therapeutic and scanning laser optical systems and optical paths of the embodiment of FIG. 4.
Figure 4D:
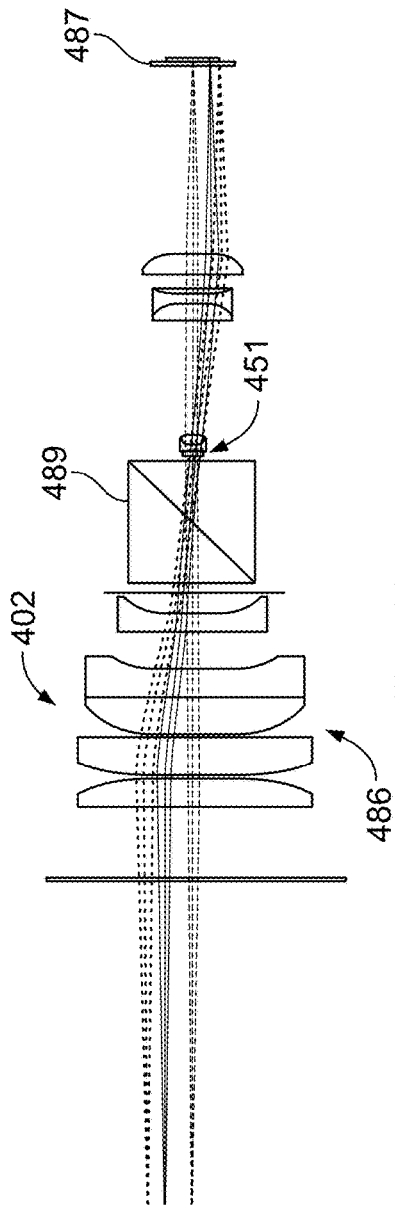
FIG. 4D is a schematic of an embodiment of the color camera with viewing along the optical path of the therapeutic laser (down the pipe) optical systems and optical paths of the embodiment of FIG. 4.
Figure 4E:
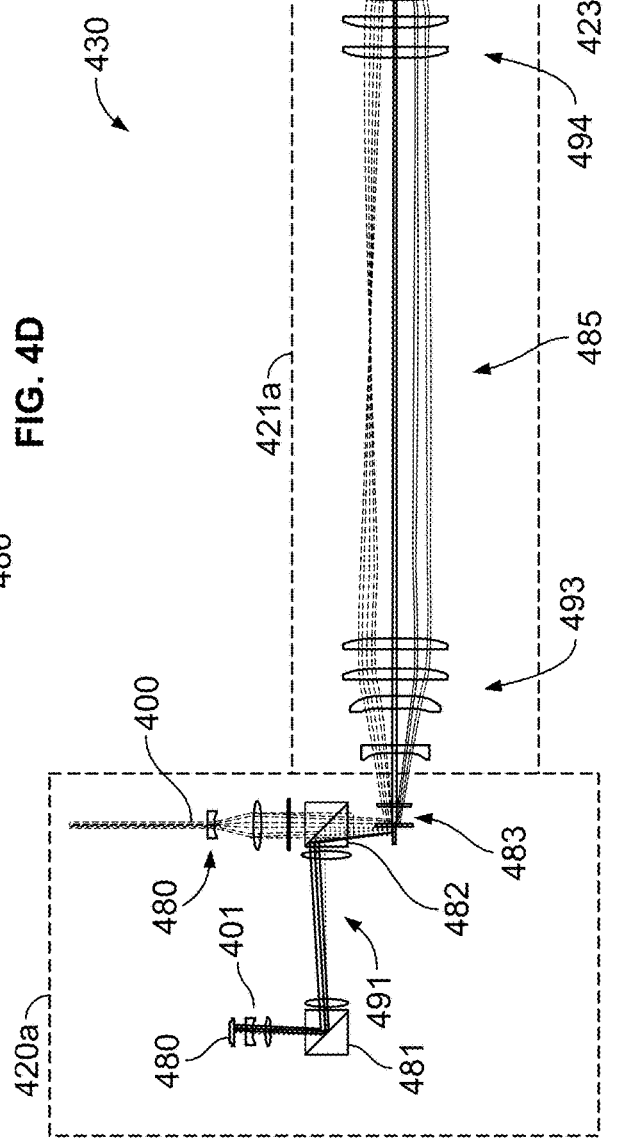
FIG. 4E is a schematic of an embodiment of optical systems and paths in accordance with the present inventions.
Figure 4F:
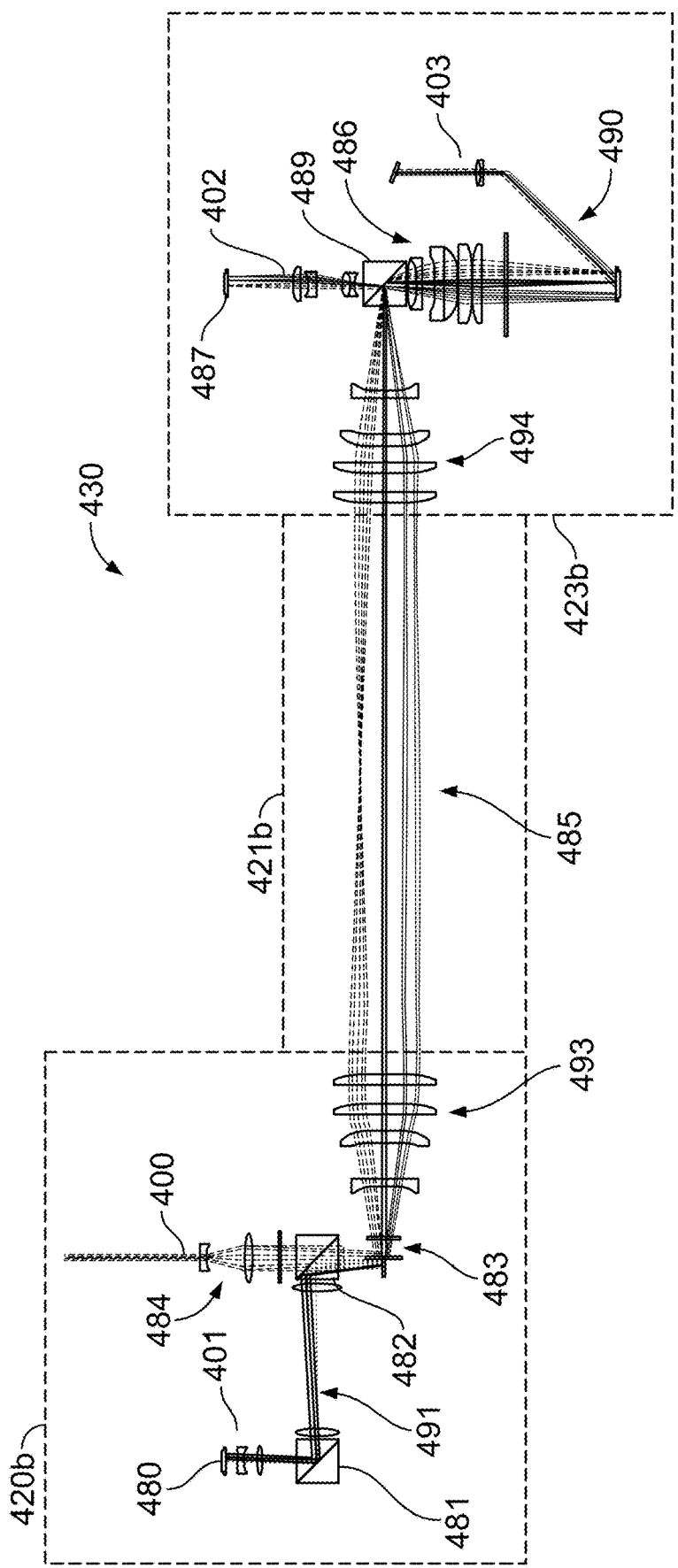
FIG. 4F is a schematic of an embodiment of optical systems and paths in accordance with the present inventions.

Sections or parts of these optical systems 400, 401, 402, 403, can be located or contained in various housings and components of embodiments of laser systems, embodiments of laser-ultrasound systems and femto-phaco systems. Thus, by away of illustration, as shown in FIG. 4 portions of the optical systems can be housed or contained within a distal housing 420, (such as for example housing 503 of FIG. 5, or housing 106 of FIG. 1), an arm 421 (such as for example arm 201 of FIG. 3, light pipe of 504 of FIG. 5 or arm 107 of FIG. 1) and a laser head or proximal housing 423 e.g., a proximal assembly or laser head (such as for example the proximal end of arm 107 in FIG. 1, head 202 in FIG. 2, or head 505 in FIG. 5). These optical systems 400, 401, 402, 403 may also be distributed between and contained within distal housing 420a, arm or connector 421a and proximal housing, e.g., a proximal assembly or laser head 423a, as shown in the configuration of FIG. 4E. These optical systems 400, 401, 402, 403 may also be distributed between and contained within distal housing 420b, arm 421b and proximal housing 423b e.g., a proximal assembly or laser head, as shown in the configuration of FIG. 4F. Other distribution and containment or housing arrangements for these optical systems is also contemplated.

Figure 4G:
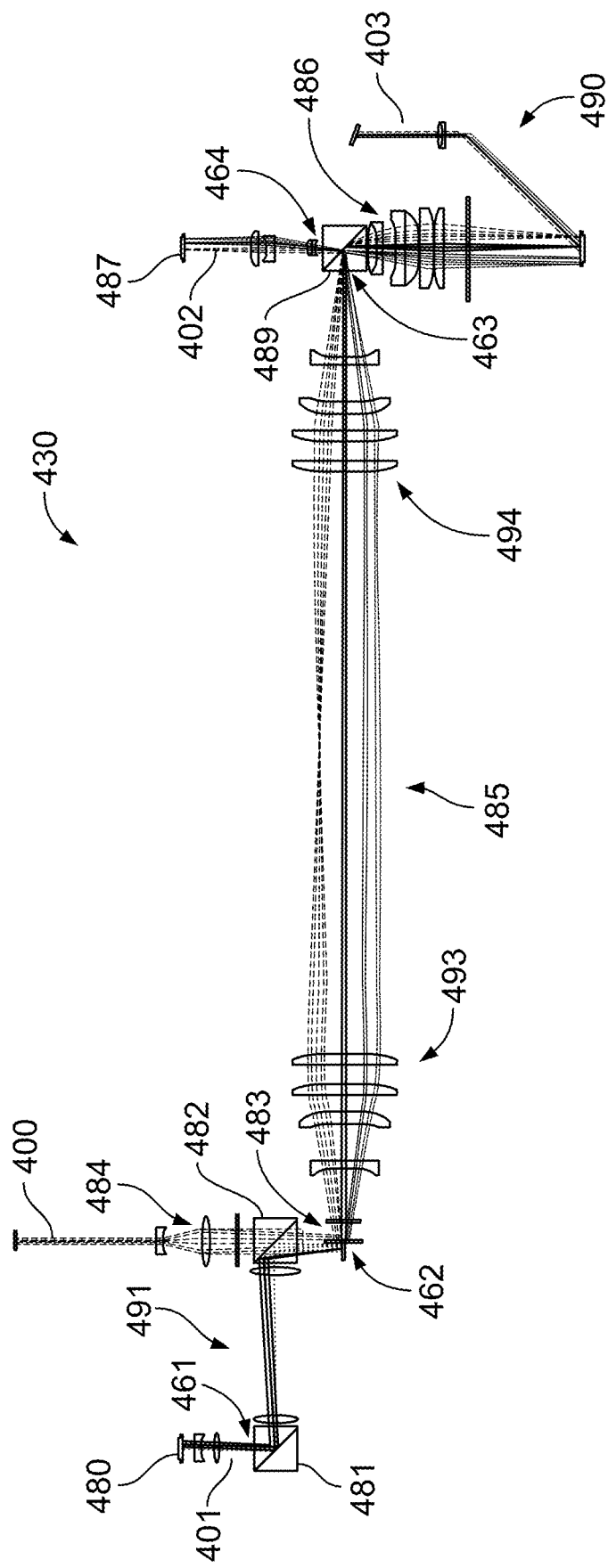
FIG. 4G is a schematic of an embodiment of optical systems and paths in accordance with the present inventions.

Turning to FIG. 4G it is seen that the optical system 430 has four pupils 461, 462, 463, 464. In this embodiment the pupils are conjugate telocentric pupils. It is noted that only three of the four pupils are along the therapeutic laser beam path.

Example 3A

The embodiment of Example 3 has coincident with the therapeutic laser a scanning laser to illuminate the structures of the eye so that optical components etc., from 403 can take images to know where the eye structures are located. Additionally, an eye fixating light source is present to aid the patient in fixation during the docking process. The fixation light source and path for this light is via the beam splitting cube that is between 402 and 403 in FIG. 4G.

Example 4A

The femto-phaco system has an image and position determining apparatus is an ultrasound based imaging system. In an embodiment the image and position determining apparatus is an Optical Coherence Tomography (OCT) system, which can determine the shape and position of the structures of the lens and structures of the eye with respect to the therapeutic laser and the therapeutic laser beam. The OCT system is integrated with, and in control communication with the laser subsystem control system, the phaco subsystem control system, the femto-phaco system control system, and combinations and variations of these.

OCT systems can also be used, for example, in the embodiments of FIGS. 1, 2, 3, 5, 14, as well as, other embodiments.

Example 4B

The embodiments of FIGS. 1, 2, 3, 5 and 14 have and use a Scheimpflug camera system as their image and position determining apparatus. The Scheimpflug camera system is an entirely different system from the OCT system. The Scheimpflug camera has a very different way of operating, functions in a different manner, and provides an output, e.g., results, that are very different from an OCT system. The Scheimpflug systems of the present inventions are believed to be superior to OCT for position and shape determinations of structures of the eye.

The Scheimpflug camera system is integrated with, and in control communication with the laser subsystem control system, the phaco subsystem control system, the femto-phaco system control system, and combinations and variations of these.

The Scheimpflug camera system may also be in control communication with a footswitch, and preferably a wireless footswitch. The control communication can be by way of bus, such as the communication bus shown in FIG. 22A

Example 5A

In an embodiment of a Femto-Phaco system the phacoemulsification subsystem has the following components and features a system that integrates both a Peristaltic and Venturi pump, allowing surgeons to independently select either pump mode for Phaco or Vitrectomy procedures. Features of this phaco subsystem include: a twin Pump System, Peristaltic and Venturi; High Vacuum Occlusion; High Speed Vitrectomy. The phaco subsystem is capable of and preforms the following procedures: diathermy, irrigation, sculpt, flop and chop, vit, visco. The user interface and software provide menu items and monitory fields for these and other phaco procedures. The interface may have GUI screens and menus such as the types shown in FIGS. 23A to 23D.

Example 5B

In an embodiment of a Femto-Phaco system the phacoemulsification subsystem has components from an Alcon CENTURION® Vision System and the Alco ACTIVE SENTRY® Handpiece and INTREPID® Hybrid.

Example 5C

In an embodiment of a Femto-Phaco system the phacoemulsification subsystem has components from an AMO WHITESTAR SIGNATURE® PRO Phacoemulsification System.

Example 6

In embodiment of a laser-ultrasound system, and in particular for a femto-phaco system, the system has a safety interlock. The safety interlock is preferably in the common control system, but could be located in, or a part of the laser control system, the phaco control system and combinations and variations of these. The safety interlock prevents the therapeutic laser from being fired when the phaco system is operating. In an embodiment, there are three stages, or gates, in the interlock system: (i) phaco system is powered down—laser can be operated: (ii) phaco system is on, and warming up, but not operational or operating—laser can be operated; and (iii) phaco is operational or operating—laser cannot be fired.

In an embodiment, stage (iii) will allow the laser to operate when the phaco system is operational, but not operating. In this embodiment only when the phaco system is operating, i.e., delivering ultrasonic energy, will the therapeutic laser be locked out, i.e., not able to fire or propagate a laser beam.

Example 6A

In an embodiment the three stages, or gates, in the interlock system are: (i) the phaco system and femto system to be powered on, primed/warming up; (ii) phaco system is on and primed but not operational—laser can be operated; and (iii) phaco is operational or operating—laser cannot be fired.

Example 7

Figure 5:
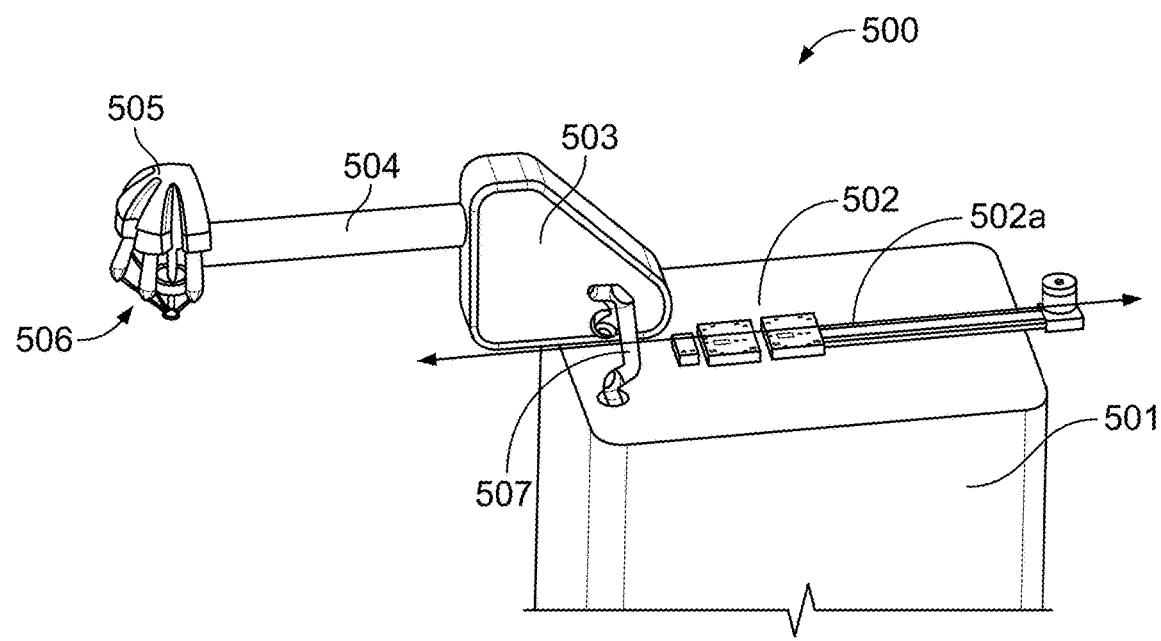
FIG. 5 is a perspective view of a system in accordance with the present inventions.

Turning to FIG. 5 there is shown a perspective view of femto-phaco laser device or system 500. The system has a lower or main housing 501 (which is only partially shown in the figure). The lower housing 501 contains the phaco system, location for phaco cartridges, and a cartridge during procedures, a therapeutic laser for generating the therapeutic laser beam, and control systems. A sliding mechanism 502 is located in the main housing 501. The slide mechanism 502 provides for movement of the upper or movable housing 503. The movable housing 503 is moved by the sliding mechanism 502 in the direction of arrow 502a, i.e., laterally, horizontally, or in and out towards and away from the patient.

The sliding mechanism can be moved automatically by for example by motors controlled by for example a joy stick, it could be moved manually and in combinations of these, e.g., where the motors can be free-wheeling. The motors can have set or predetermined positions, and can also be in control communication with the smart head rest, so as to precisely locate or position the laser delivery head 505 over the patient head rest and by this the patient and the patient's eye to be operated on.

The upper or movable housing 503 contains the laser focusing z-direction optics, x-y scanning optics and other beam processing or handling components. The housing 503 may also contain other optical systems and optical paths as discussed in Example 3.

The housing 503 is in optical communication with the therapeutic laser by way of an articulated light pipe 507. The articulated light pipe provides a free space laser beam path that directs the laser beam from the lower housing 501 to the housing 503 and delivers the therapeutic laser beam along a laser beam path to the optical components in housing 503. In this embodiment, as seen in greater detail in FIG. 5I, the articulated light pipe 507 has six joints having a reflective surface on the inside of each joint. Preferably, the light pipe 507 keeps the therapeutic laser and housing 501 in optical communication with housing 503 and the optical components in that housing in all of the possible positions and orientations of housing 503.

The housing 503 has an arm 504, which is a rigid hollow light pipe that houses or contains one or more optical paths, including the therapeutic laser beam path, and the other paths as discussed in Example 3. The arm 504 connect the housing 503 with the laser delivery head 505, and keeps those components in optical communication. The arm 504 may also carry control and communication cables, optical fibers or wires for transmitting controls and in formation between the components of the laser head and the control systems. The laser head 505 is located at the proximal end of arm 504 and the housing 503 is located at the distal end of arm 504.

The laser head has a position and shape determining apparatus 506, which is a Scheimpflug device, having five cameras. (In an embodiment there are six fixed cameras. In an embodiment a there is a single movable camera.)

Example 8

Turing to FIGS. 5A to 5H there is shown various views of and embodiments of position adjustment mechanisms for use with the system of FIG. 5 (like numbers having like meaning and referring to like components).

Figure 5A:
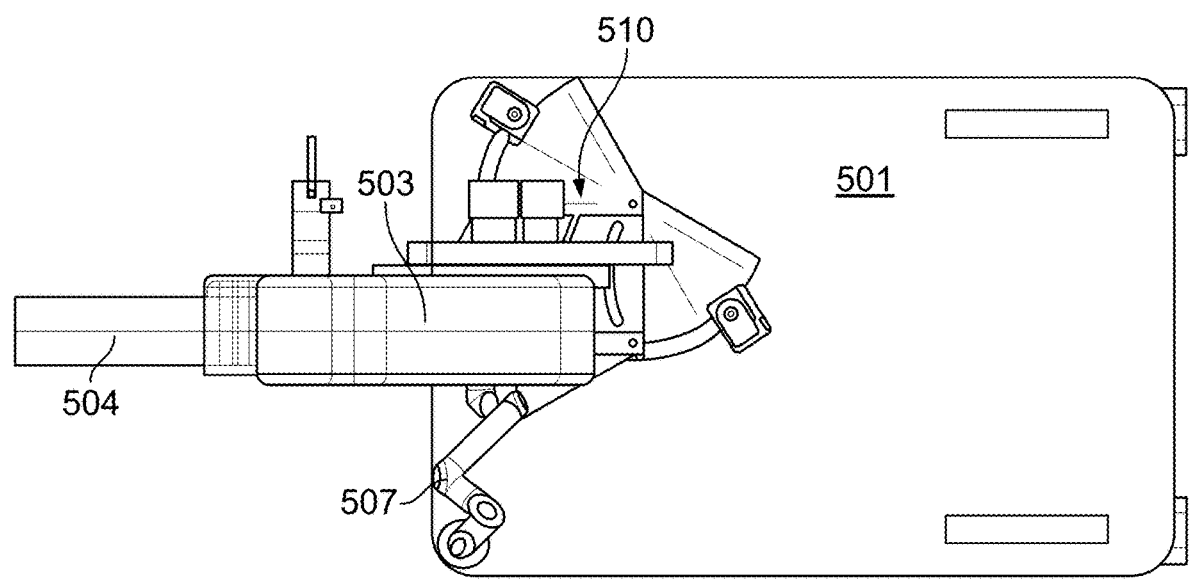
FIG. 5A is a top view of a portion of an embodiment of a system in accordance with the present inventions.

Turning to FIG. 5A The position adjustment mechanism 510 is generally positioned on the other side of housing 503 away from the arm 507. Parts of the mechanism 510 may be located below the housing 503 and on or in the housing 501.

Figure 5B:
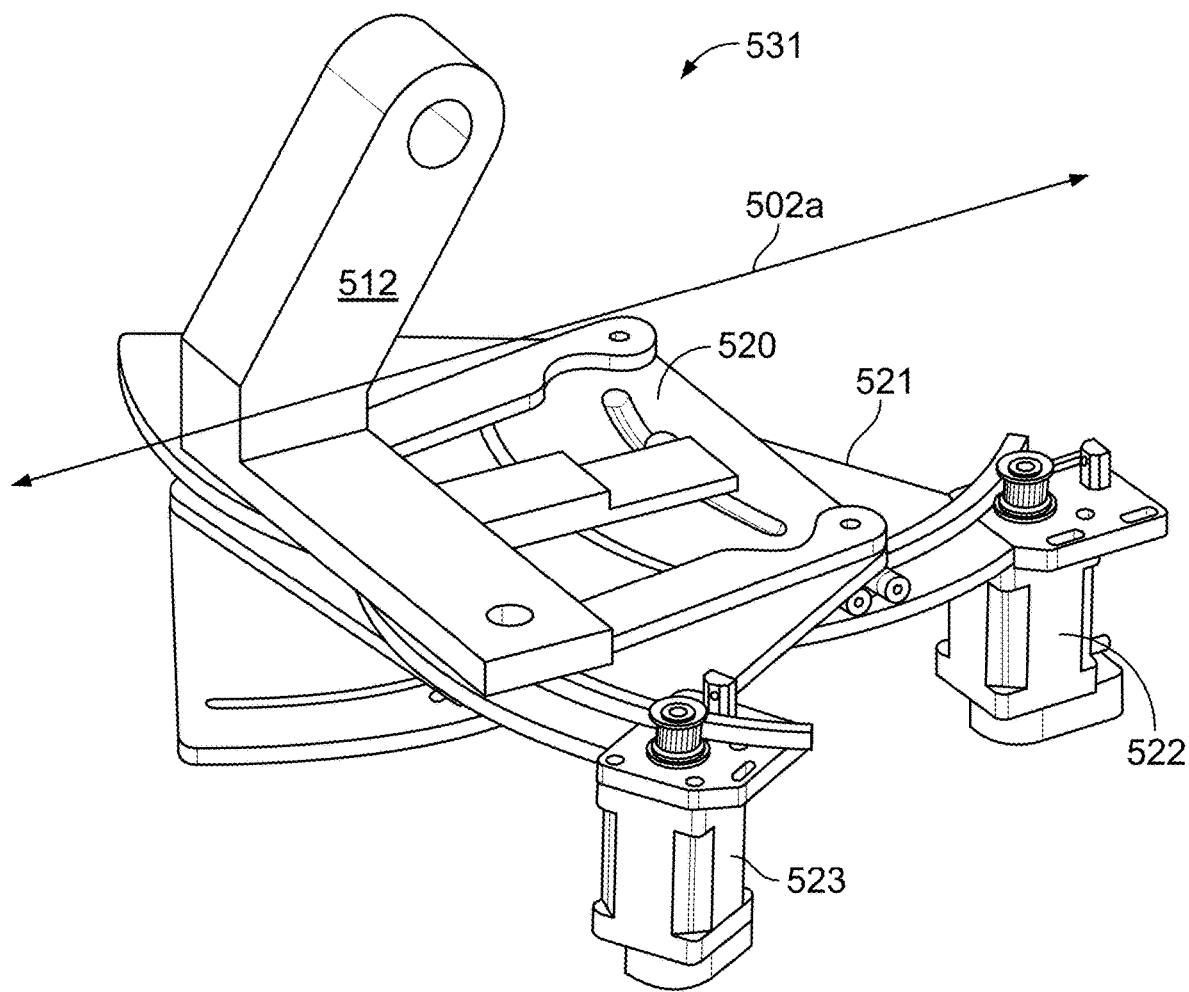
FIG. 5B is a perspective view of an embodiment of a positing assembly in accordance with the present inventions.

FIG. 5B shows the lateral movement assembly 531, which is a part of the position adjustment mechanism 510. The lateral movement assembly 531 has a first plate 520, and a second plate 521 that are moveably mechanically associated with motors 523 and 522, by for example drive gears or wheels. The plates 520, 521 are moved in an arcuate manner that translates into lateral movement, i.e., in the direction of arrow 502a, for the fixed post 512. Fixed post 512 is attached to a free movement assembly, such as assembly 513. The lateral movement assembly 531 is mechanically associated with housing 501, and can be housed on, and preferably within housing 501.

Example 9

Figure 5C:
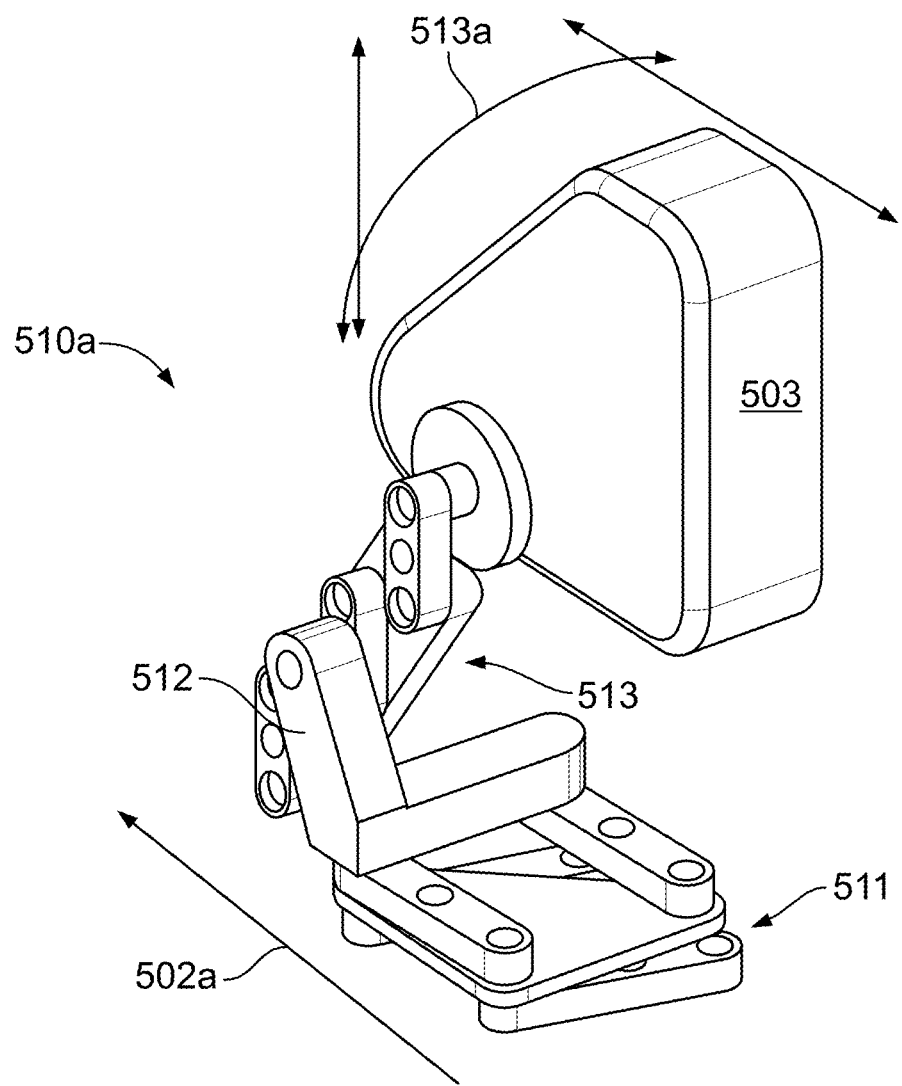
FIG. 5C is a perspective view of an embodiment of a positing assembly in accordance with the present inventions.
Figure 5D:
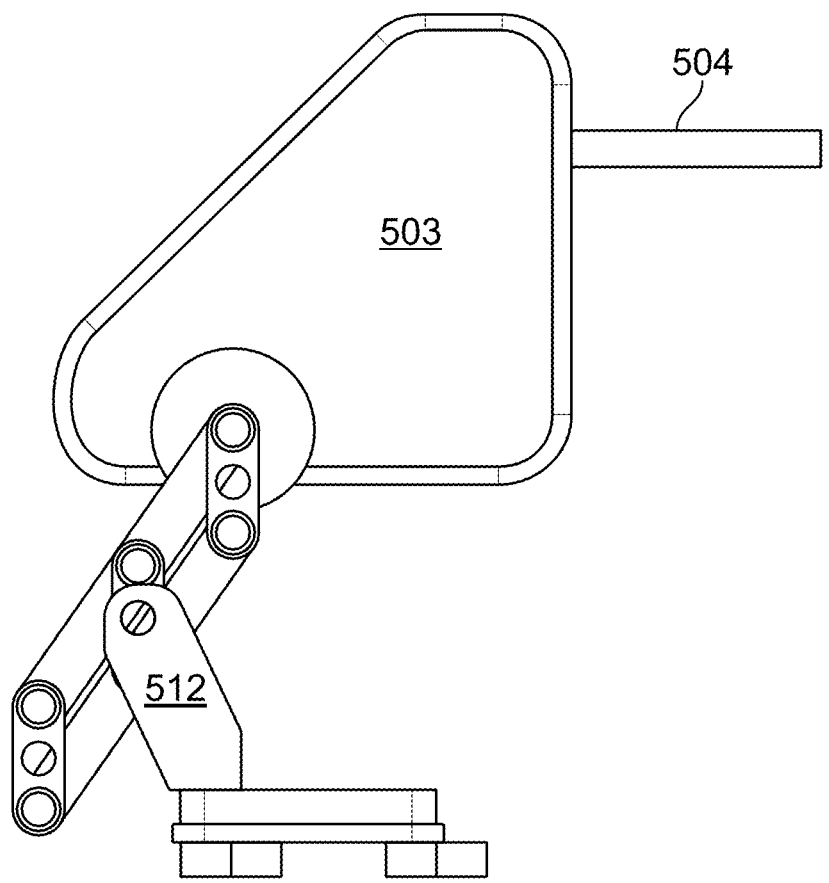
FIGS. 5D TO 5H are side view of positions of an embodiment of the present systems in accordance with the present inventions.

Turning to FIG. 5C there is shown a lateral movement assembly 511 that has a four bar linkage, which is part of the position adjustment mechanism 510a; and provides movement in the direction of arrow 502a. The lateral movement assembly 511 is mechanically associated with housing 501, and can be housed on, and preferably within housing 501.

It being understood that the lateral movement assembly 511 of Example 8 may be used with the position adjustment mechanism 510a of Example 9 and vis versa. It being understood that the free movement assembly 513 can be used with either lateral movement assembly 511 or lateral movement assembly 531. It being understood that other free movement type mechanical and electro-mechanical devices, and lateral type movement mechanical and electro-mechanical devices can be used.

The assembly 511 is attached to a fixed post 512. The assembly moves fixed post 502 in the direction of arrow 502a. The fixed post 512 is connected to a free movement assembly 513. Free movement assembly 513 provide movement of housing 503 in an arcuate manner, a lateral manner, a vertical manner and combinations of these, as generally shown by the collection of arrows 513a. Assembly 513 is a parallelogram linkage.

The assembly 513 can be motorized, can have predetermined positions, or can be operated by hand, e.g., holding the arm 504, the housing 503 or other part, and changing the position of the housing 503. In an embodiment the housing 503, arm 504 and laser head 505 are counterbalanced such that the housing 503 can be moved with less than 10 lbs of force, less than 7 lbs of force, less than 5 lbs of force and less than 2 lbs of from, from about 2 to about 7 lbs of force, from about 4 to about 6 lbs of force, and combinations and variations of these. Preferably, once moved, the housing 503 will stay in the position it was placed in, until acted upon by sufficient force to move it. (For simplicity the arm 504, and laser head 505, are not shown in FIG. 5C)

Figure 5E:
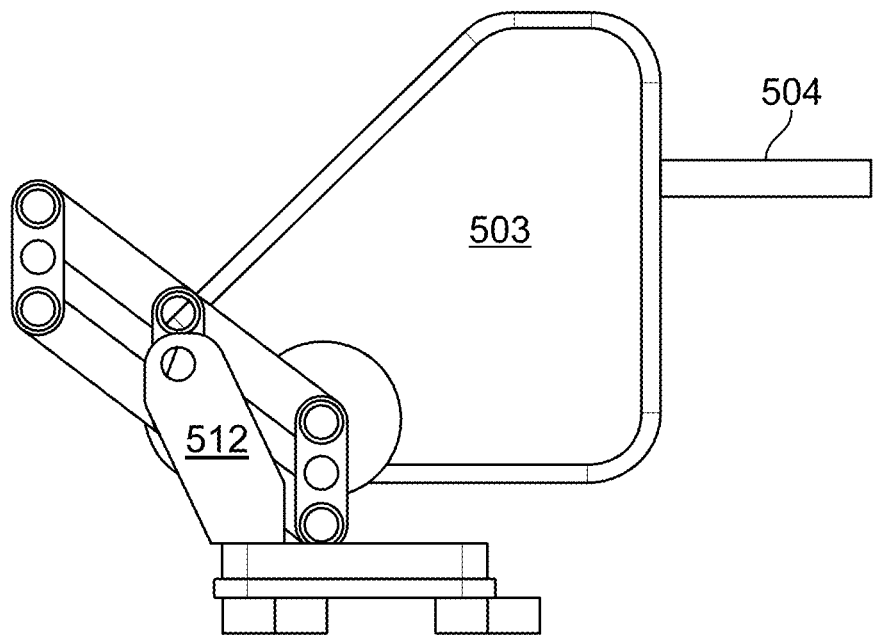
Figure 5F:
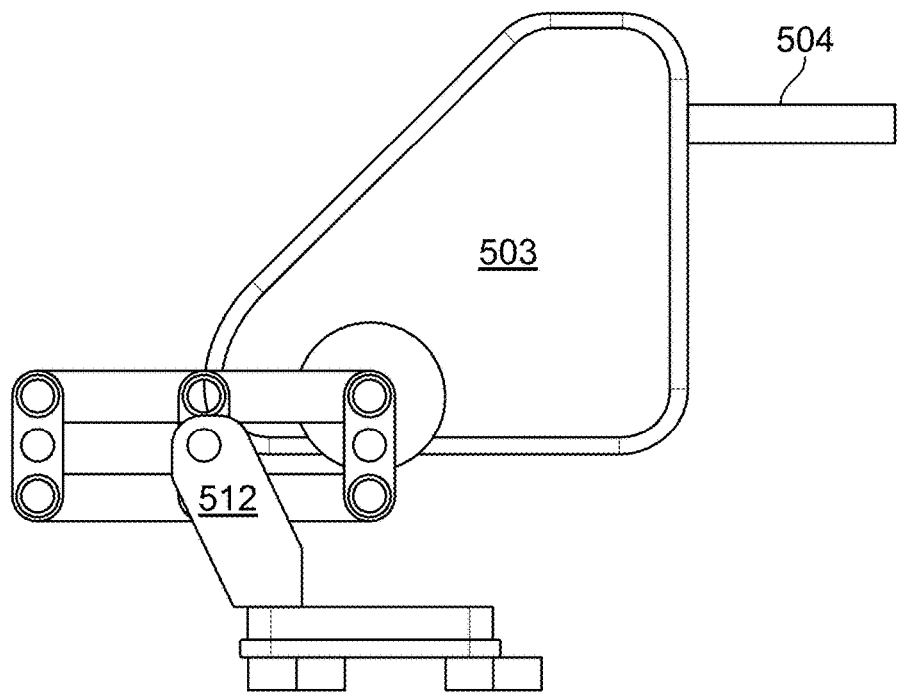
Figure 5G:
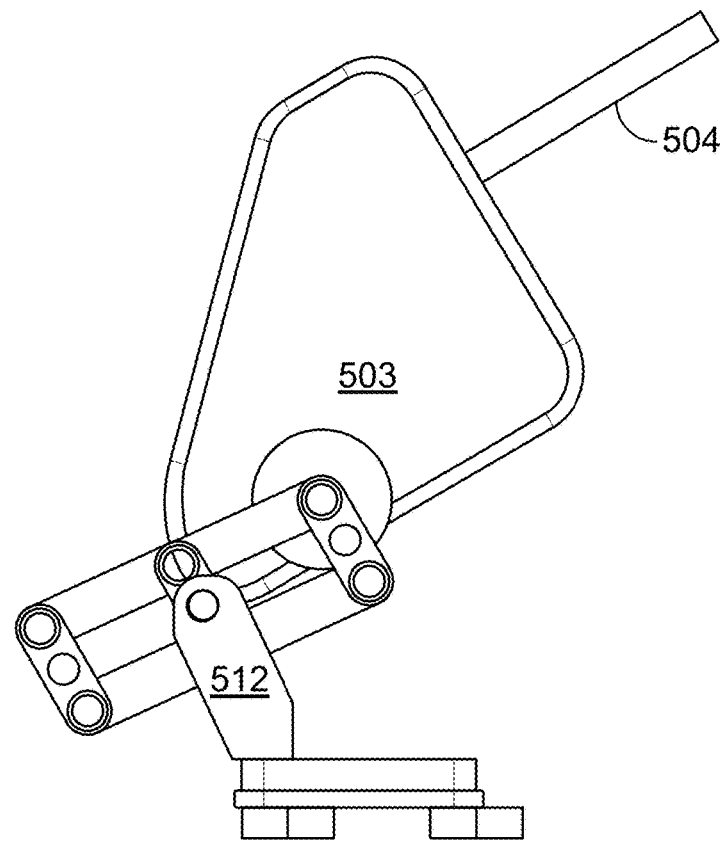
Figure 5H:
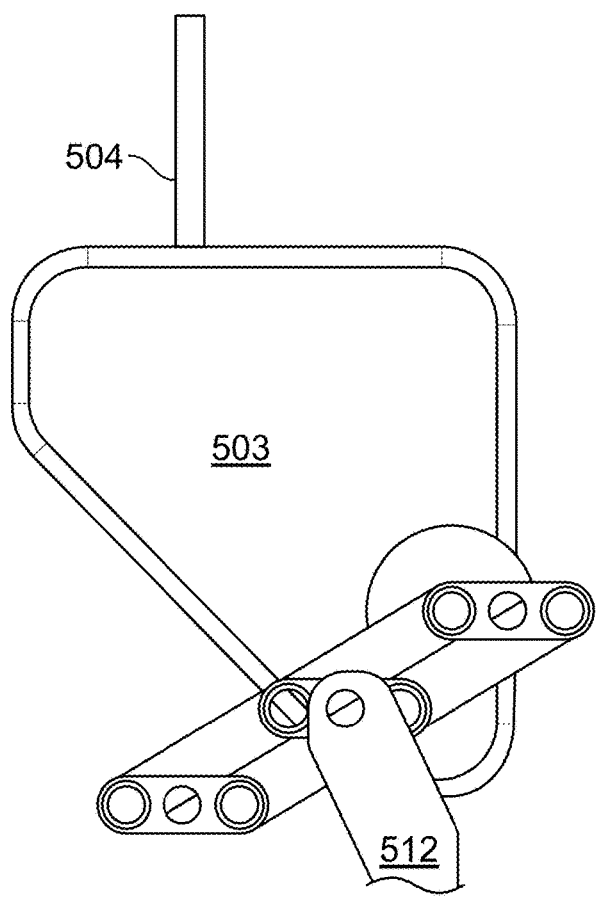
Figure 5I:
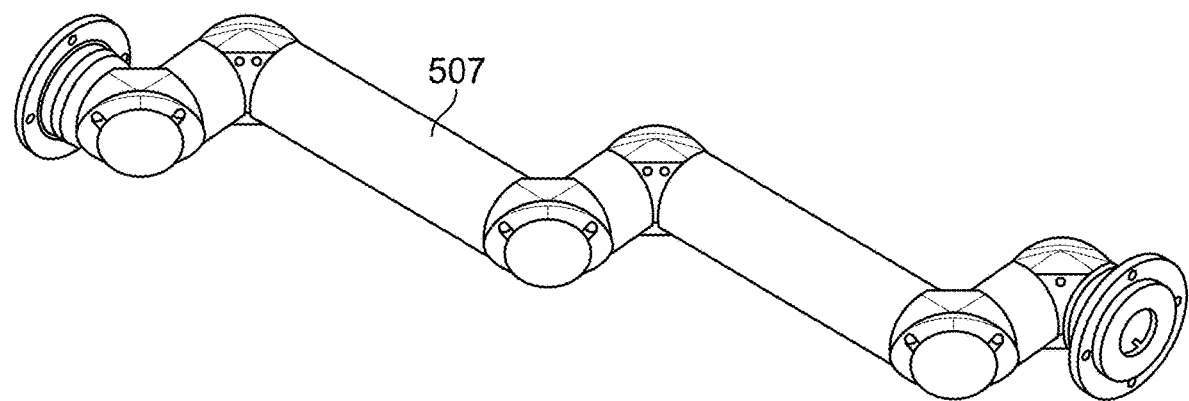
FIG. 5I is a perspective view of an embodiment of an articulated light pipe in accordance with the present inventions.

FIGS. 5D to 5H show some of the positions that the free movement assembly 513 can place the housing 503 in. The position of FIG. 5H is idea for storage of the system, and for cleaning of the operating room. The position of FIG. 5E is for performing laser operations on a patient.

Example 10

In an embodiment the laser-ultrasound system, and in particular a femto-phaco system has the patient bed or support attached to the system.

Example 11

In an embodiment the patient support, e.g., bed, is not attached to the laser-ultrasound system, and in particular a femto-phaco system. The patient support and the femto-phaco system are completely positionable with respect to each other, with no physical restraints between them. Thus, the femto-phaco system can be positioned in any location or orientation with respect to the patient support (provided of course that the patients head is within reach of the arm and the phaco tubing). An orientation/positional tracking system using NC electromagnetic fields, gyroscopes, accelerometers, and magnetometers is used to determine the orientation of the patient's head with respect to the therapeutic laser and the therapeutic laser beam path. This orientation tracking system can determine the angle of the arm, e.g., arm 504 of the system of FIG. 5, to within ±5 degrees, ±3 degrees, and ±2 degrees, and greater and lesser accuracies. Using this angle, the therapeutic laser beam delivery pattern is adjusted, preferably by the control system, to deliver the laser beam pattern at the correct angle of orientation for the patient's eye.

In an embodiment a Polhemus Patriot™ 6-DOF tracking sensor is located in the patient headrest, with the transmitter mounted on the system frame near the front of the delivery system. This provides sufficient information to determine the orientation of the headrest with respect to the laser delivery system. This orientation/position tracking system is further described in Appendix A, the entire disclosure of which is incorporated herein by reference.

Example 12

The electromagnetic tracking system is used in a stand alone therapeutic laser system, that does not have a phaco subsystem. The stand alone therapeutic laser system has a patient support that is not attached to the laser system. The electromagnetic tracking system determines the angle of orientation of the patient's eye to the laser system. The laser system configures the laser delivery pattern to meet the determined angle.

Example 13

The systems of Examples 11 and 12 have flexible or positionable mechanical attachments between the patient support and the therapeutic system. The electromagnetic tracking system is used to determine the position and, in particular, the angle of the patient's eye to the therapeutic system. The laser system configures the laser delivery pattern to meet the determined angle.

Example 14

The components of the electromagnetic tracking system, e.g., gyroscope, accelerometer and magnetometer are arranged in the patient support, the patient head support, on the patient themselves, and in the therapeutic system in various arrangements, with the gyroscopes, accelerometers, and magnetometers being located in one or more of those components.

Example 15

In an embodiment a combination of devices such as gyroscopes, accelerometers, and digital compass are located in the patient head rest and two magnetometers are positioned in the femto-phaco system. This provides sufficient devices to determine the orientation, e.g., the angle of the patient to the laser arm and laser beam path and pattern.

A compass based position deterring system using gyroscopes, accelerometers, and magnetometers is used to determine the position of the patient's head, and in particular the eye upon which the surgery is going to be performed is to know with respect to the therapeutic laser and the therapeutic laser beam path. This compass based positioning system can determine the angle of the arm, e.g., arm 504 of the system of FIG. 5, to within ±5 degrees, ±3 degrees, and ±2 degrees, and greater and lesser accuracies. Using this angle, the therapeutic laser beam delivery pattern is adjusted, preferably by the control system, to deliver the laser beam pattern at the correct angle of orientation for the patient's eye.

In an embodiment a gyroscope and an accelerometer are located in the patient head rest and two magnetometers are positioned in the femto-phaco system. This provides sufficient devices to determine the orientation, e.g., the angle of the patient to the laser arm and laser beam path and pattern.

The components of the compass based position determining system, e.g., gyroscope, accelerometer and magnetometer are arranged in the patient support, the patient head support, on the patient themselves, and in the therapeutic system in various arrangements, with the gyroscopes, accelerometers, and magnetometers being located in one or more of those components.

The systems of Examples 11 and 12 have flexible or positionable mechanical attachments between the patient support and the therapeutic system. The compass based position determining system is used to determine the position and, in particular, the angle of the patient's eye to the therapeutic system. The laser system configures the laser delivery pattern to meet the determined angle.

The compass based position determining system is used in a stand alone therapeutic laser system, that does not have a phaco subsystem. The stand alone therapeutic laser system has a patient support that is not attached to the laser system. The compass based position determining system determines the angle of orientation of the patient's eye to the laser system. The laser system configures the laser delivery pattern to meet the determined angle.

Example 16

The head rest, or other remote component (i.e., not a part of the therapeutic system) of the tracking system, e.g., the electromagnetic tracking system, has rechargeable batteries, that can be recharged at separate charging station, storage container, or on the therapeutic system.

Example 17

In an embodiment of the femto-phaco system the control system recommends, e.g., matches, cataract grade, laser power and pattern, and ultrasound rate, power, phase angles, flow and fluidics rates and other aspects associated with handpiece and phaco operation. In this manner the system recommends and predetermines all energies and fluid flow rates that are delivered to the eye as part of the therapy as a fully integrated device. In an embodiment the phaco hand piece is tuned by the system controller to optimize the phaco procedure based on the prior laser procedure, which in turn was based on prior cataract grading. The system provides a single system that is capable of quickly, and without requiring the movement of the patient or the location of the system, determining the shape and position of the structures of the cornea, e.g., anterior and posterior surfaces, the lens of the eye, e.g., anterior capsule, posterior capsule, grade the type or density of the cataract, perform a laser capsulotomy, and a laser fragmentation on the lens, and then perform phacoemulsification of the laser fragmented lens material to remove that material for insertion of an IOL. The system is configured to use information obtained from each prior step of the procedure to optimize the next step in the procedure. In this manner the system provides completely integrated and predetermined total energy delivery, and energy delivery profile, to the eye during the ophthalmic procedure. In embodiments the total energy delivery and energy delivery profiles are based upon the grade of the cataract being treated. The total energy delivery and energy delivery profiles include both laser energy and ultrasonic energy.

Example 18

In embodiment the femto-phaco system provides a predetermined variable mode for the surgeon or practitioner providing the procedure. Thus, in this mode the system, working in conjunction with the laser controller system, and the phacoemulsification control system, predetermines, and makes available, recommends and preferably optimizes ranges, and settings for the phacoemulsification procedure. This embodiment further can "learn" based upon the surgeon's selections and preferences to provide tailored optimum ranges based upon the surgeons practice and inputs.

Example 19 in embodiment the femto-phaco system provides adjustable modes providing for more variability, and predetermined variability, such as for example, by the system providing ranges of adjustments for the ultrasound that are based upon the laser beam pattern or laser therapy delivered to the lens, the cataract grade, which is preferably determined by the system or which can be provided to the system, and other factors. The system can then provide recommend ranges and adjustment for the procedure that would include: (i) recommendation of torsional lateral motion; transversal lateral motion, or no lateral motion; (ii) recommendation of laser pattern to increase fragmentation, and thus lower phaco power to manage heat buildup in the eye; (iii) a recommended duty cycle.

Duty cycles, and duty cycle recommendations can include for example the choice of a mode such as pulse mode, which alternates phaco power pulses with periods of rest, the default ratio is 50:50. This is called a 50% duty cycle, as each complete cycle is composed of power on for 50% of the time, then power off for 50% of the time. This default ratio can be changed to alter the ratio of ultrasound energy to the rest interval. For example, 40% results in 40 msec on, 60 msec off giving a ratio of 40:60. When are higher or lower duty cycles preferred? The answer depends on the phase of surgery. For sculpting the nucleus, such as with the technique of divide-and-conquer, the surgeon needs to deliver sufficient energy to be able to cut the grooves. This requires a duty cycle of about 40% to 60%. Once the surgeon has placed grooves in the nucleus and has achieved cracking that results in quadrants, a lower duty cycle can be used during the phaco-assisted aspiration of the quadrants. For this quadrant removal, a lower duty cycle of 20% to 40% can be used since the principal force for aspiration is the fluidics and not the ultrasound.

Example 20

In embodiment the phaco subsystem is used to only separate the laser cut material, as for example, when the laser cuts the material in sizes that are smaller than the phaco aspiration needle opening.

Example 21

The laser ultrasound system, and in particular a femto-phaco system has an integrated microscope.

Example 22

An adaptor is used in the housing of the phaco-femto system to fit or use multiple companies' or types of phaco packs and phaco cassettes. The adaptor has the requisite hardware adapters and software to provide for full, efficacious, and approved operation of the system. The adaptor may be a part of the housing, it may be a separate insert or component for the housing, or it may be a part of or integral with the cassette.

Example 23

Figure 6:
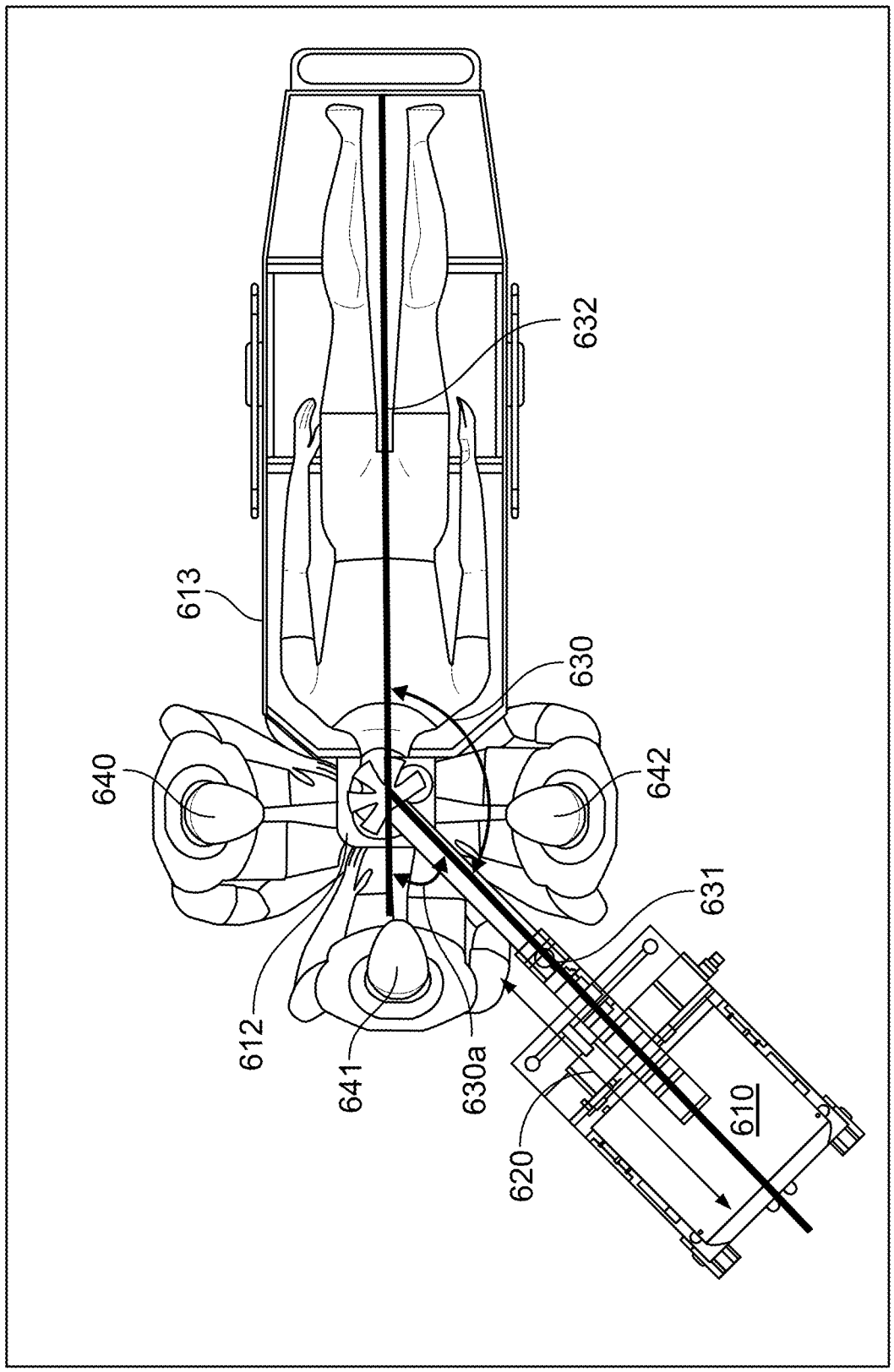
FIG. 6 is a top view of a embodiments of configurations of systems in accordance with the present inventions.

Turning to FIG. 6 there is shown a plan view of a laser-ultrasound system, in particular a femto-phaco system positioned for use in preforming a laser-ultrasound therapeutic procedure. The femto-phaco system 610 is positioned at an angle between the temporal position and the superior position. The laser delivery head can be extended to the patient for performing the laser surgery, and moved away from the patient for the ultrasound procedure as shown by arrow 620. The head rest 612 and the patient support 613 are positioned with respect to the femto-phaco system. The system and the patient support have a positioning system, e.g., an electromagnetic positioning system, that determines angle 630, angle 630*a* or both of the laser system with respect to the patient head rest and thus the patient. The angle is measured is the angle between the longitudinal axis 631 of the arm and the longitudinal axis 632 of the patient, in particular the patient's head, as determined by the head rest.

Three positions of a surgeon are shown, superior 641, and temporal 640, 642. As can be seen regardless of the surgeon's preference to their position, the laser arm does not interfere with the procedure.

Additionally, the laser head can readily and easily be repositioned to access and perform laser procedures on both eyes of the patient, without requiring repositioning of the patient support or the location of the femto-phaco system.

In embodiments laser system can be positioned to have an angle 630 of from about 30 degrees to about 320 degrees and any angle within this range. The only restriction to this angle is the area where the patient support is located. The surgeon being able to be positioned at the superior or either temporal positions, among others.

Example 24

Figure 7:
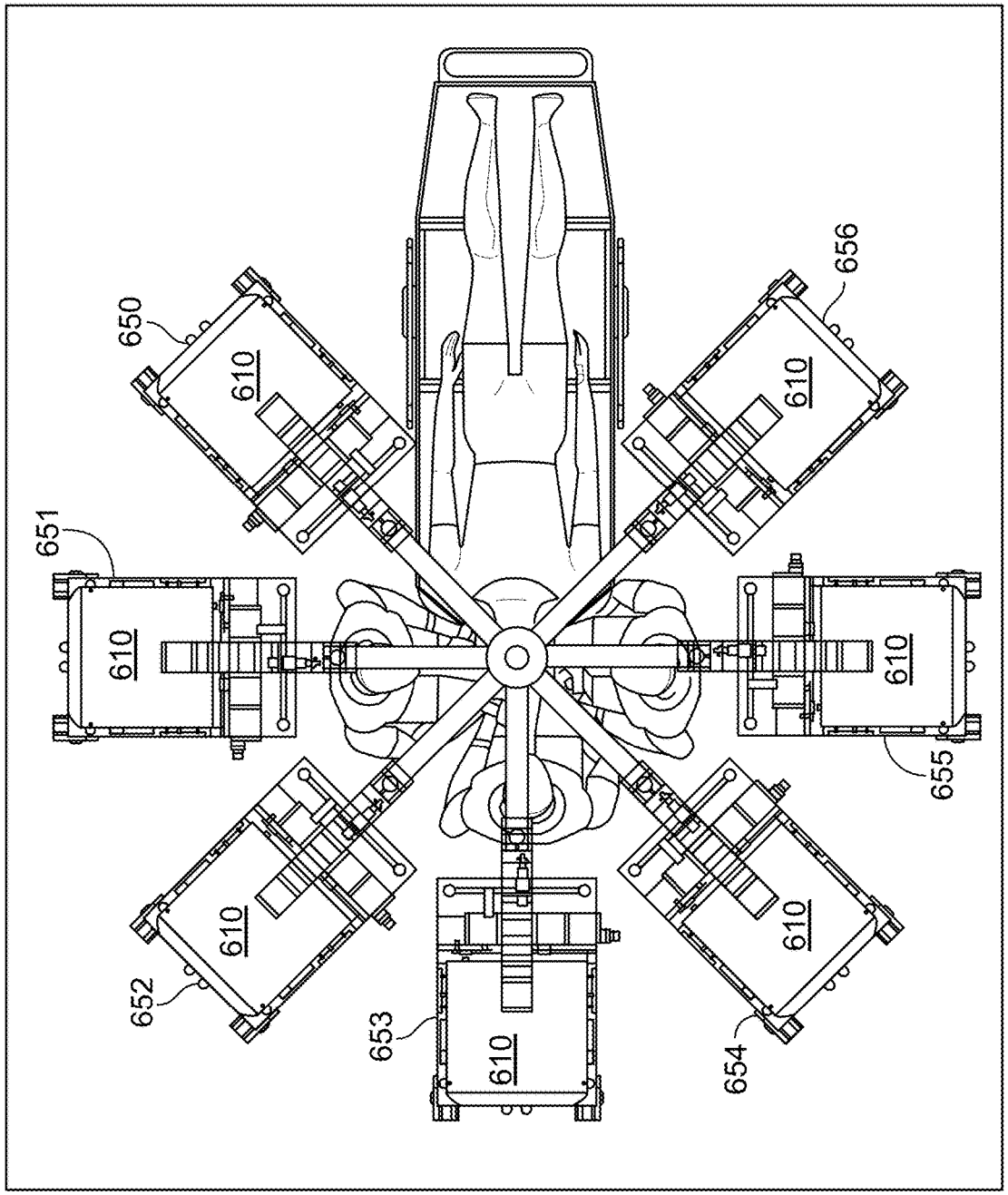
FIG. 7 is a top view of a embodiments of configurations of systems in accordance with the present inventions.

Turning to FIG. 7 there is shown several of these possible configurations and surgeon positions, all providing full access to the surgeon. This full access is to either eye of the patient, for each of these configurations. Thus, the laser-ultrasound system 610 can be located at: a 45 degree angle 656, a 90 degree angle (i.e., temporally) 655, a 135 degree angle 654, a 180 degree angle (i.e., superiorly) 653, a 225 degree angle 652, a 270 angle (i.e., temporally) 651 and a 315 degree angle 650. It being understood that the laser-ultrasound system can be located at any angular position between those shown in the figure. Thus, there is provide for full positioning, e.g., "clocking" of laser-ultrasound system around each of the eyes of the patient. In this manner the system can be said to non-handed, in that the system configuration is the same for both left handed and right handed positions for a surgeon.

Example 25

Figure 8:
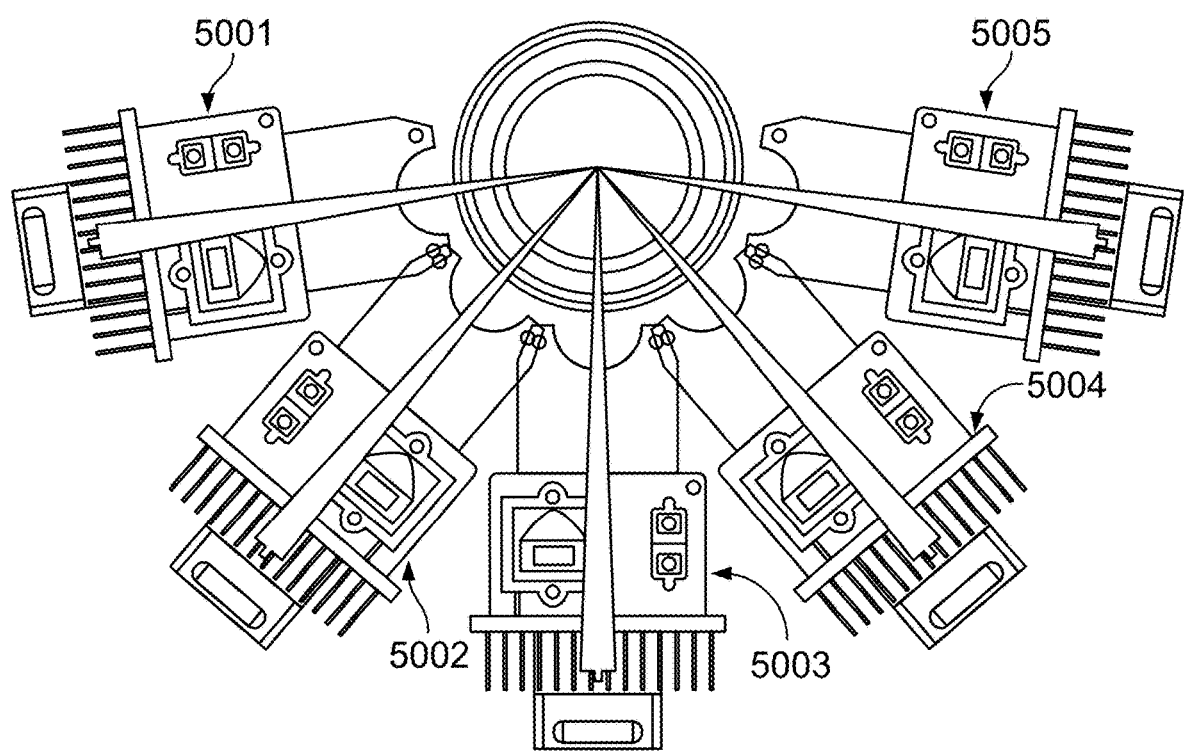
FIG. 8 is a top view of an embodiment of a Scheimpflug assembly in accordance with the present inventions.

FIG. 8 is an embodiment of a Scheimpflug shape and position determining assembly for use in a laser delivery head of the present systems. This embodiment is a 5 camera configuration, with the cameras 5001, 5002, 5003, 5004, 5005 being spaced 40 degrees apart. This placement allows for the system to operate in any of the configuration of Examples 23 and 24. Even though in some configurations and for some patients one or two cameras may be blocked the system will still operate and provide reliable images for shape and position determinations.

Example 26

Figure 9:
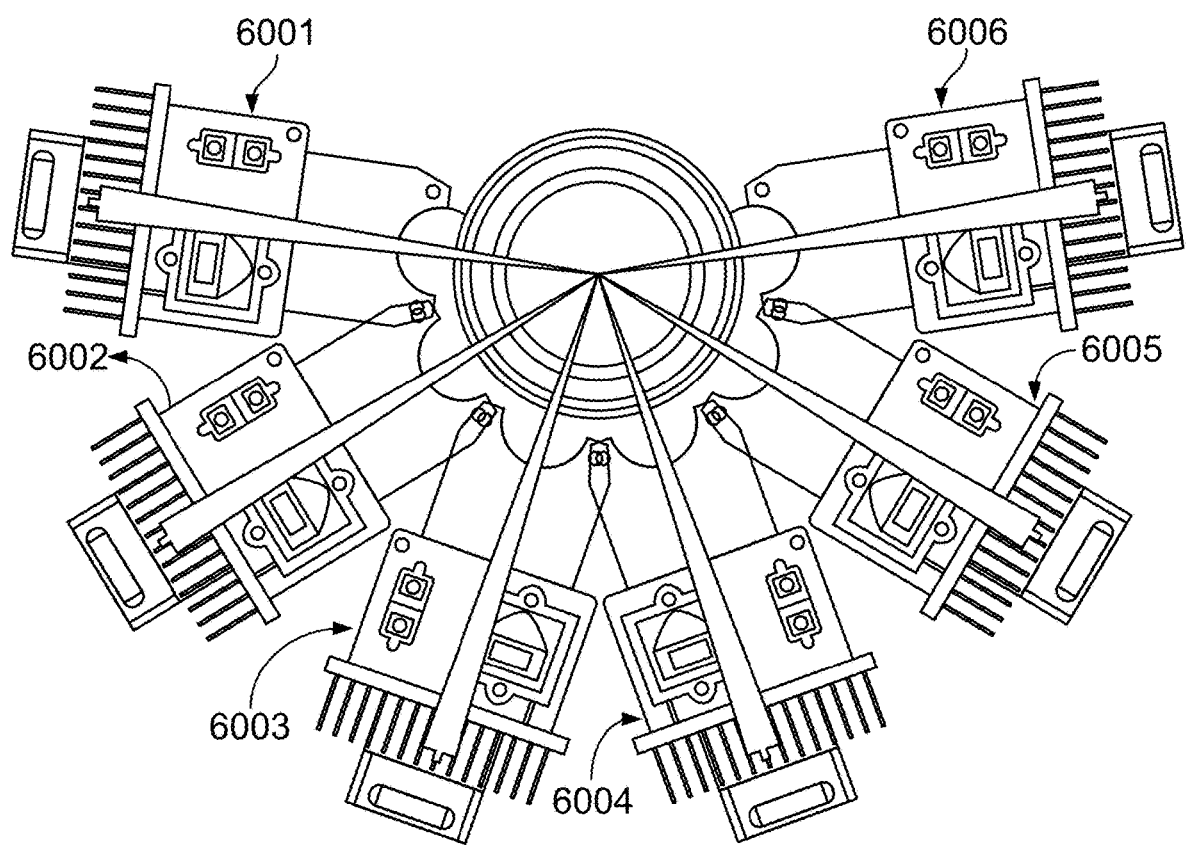
FIG. 9 is a top view of an embodiment of a Scheimpflug assembly in accordance with the present inventions.

FIG. 9 is an embodiment of a Scheimpflug shape and position determining assembly for use in a laser delivery head of the present systems. This embodiment is a 6 camera configuration, with the cameras 6001, 6002, 6003, 6004, 6005, 6006 being spaced 40 degrees apart. This placement allows for the system to operate in any of the configuration of Examples 23 and 24. Even though in some configurations and for some patients one or two or three cameras may be blocked the system will still operate and provide reliable images for shape and position determinations.

Example 27

Figure 10A:
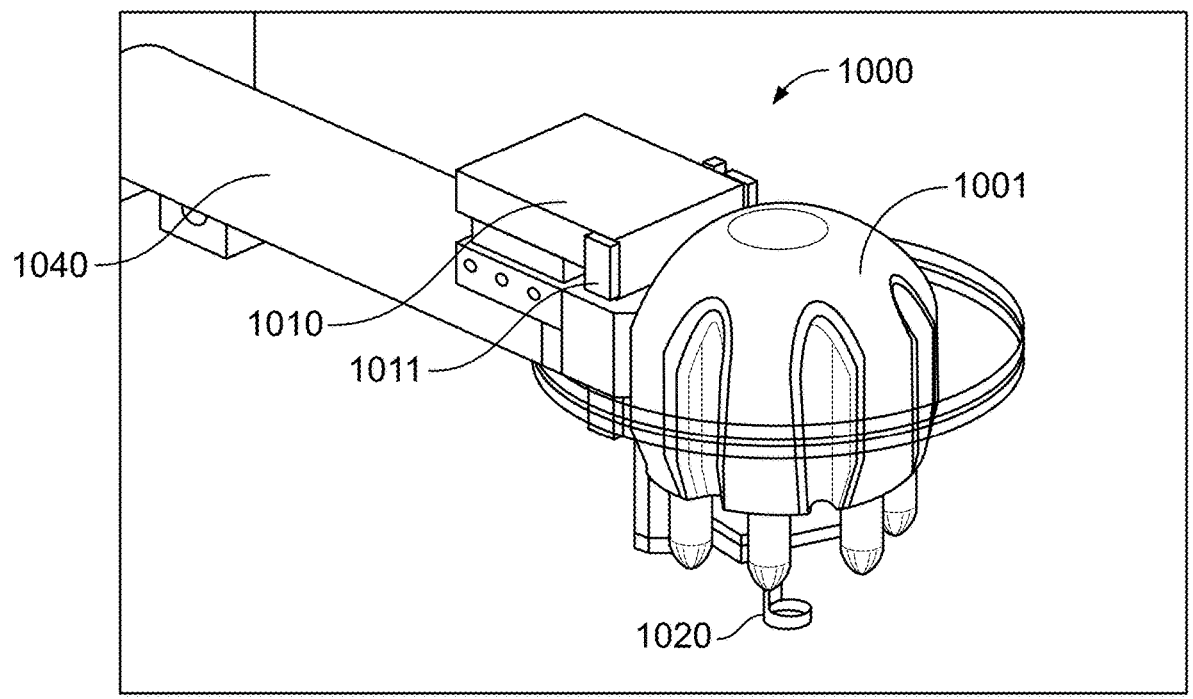
FIGS. 10A and 10B are prospective views of an embodiment of a proximal assembly and docking system in accordance with the present inventions.
Figure 10B:
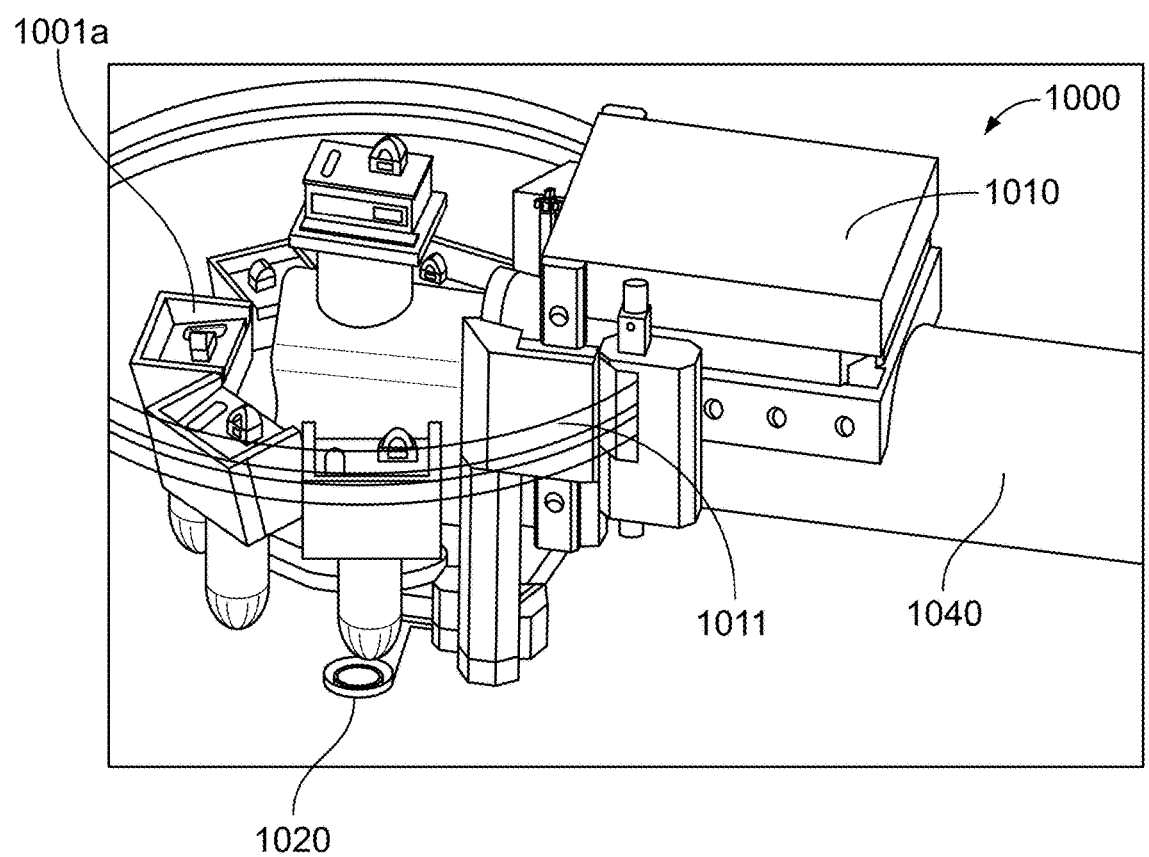
Figure 11:
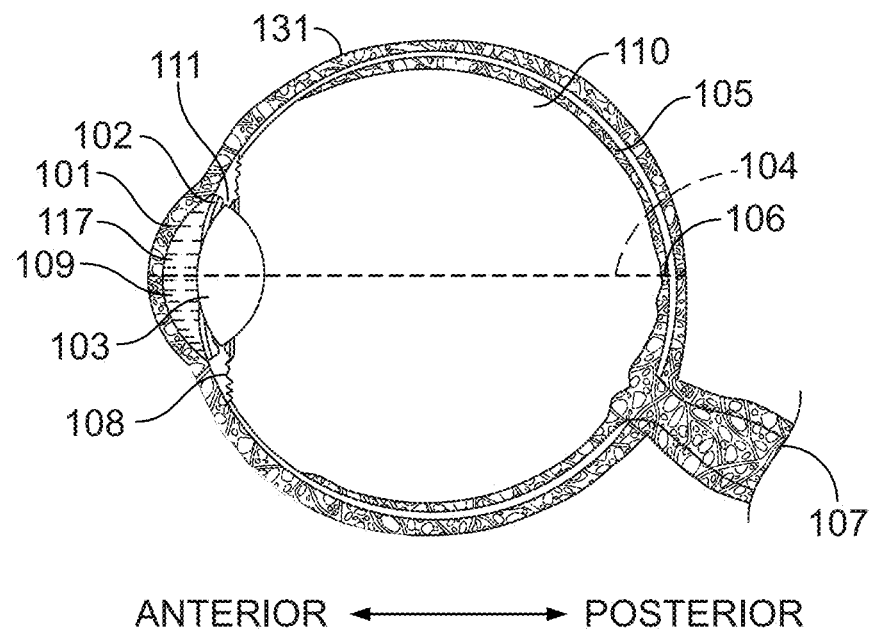
FIG. 11 is a cross sectional view of a human eye.
Figure 11A:
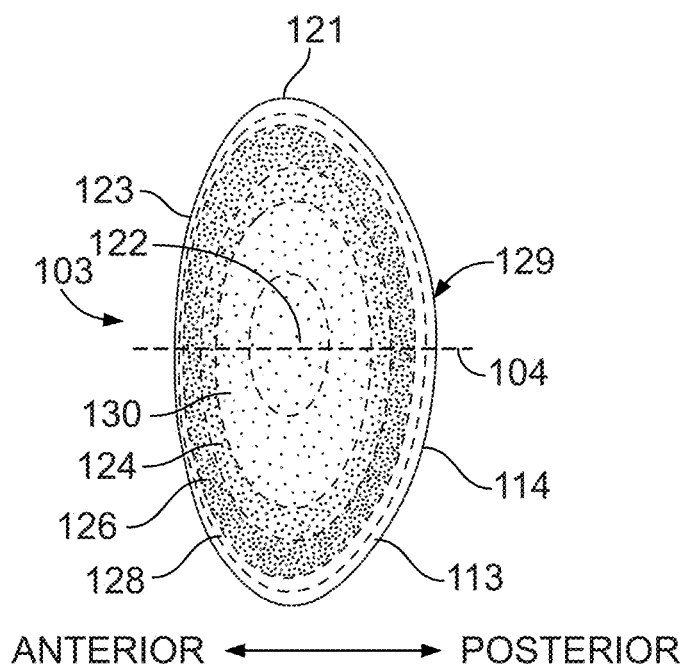
FIG. 11A is a cross sectional view of the lens of the eye of FIG. 11.
Figure 12A:
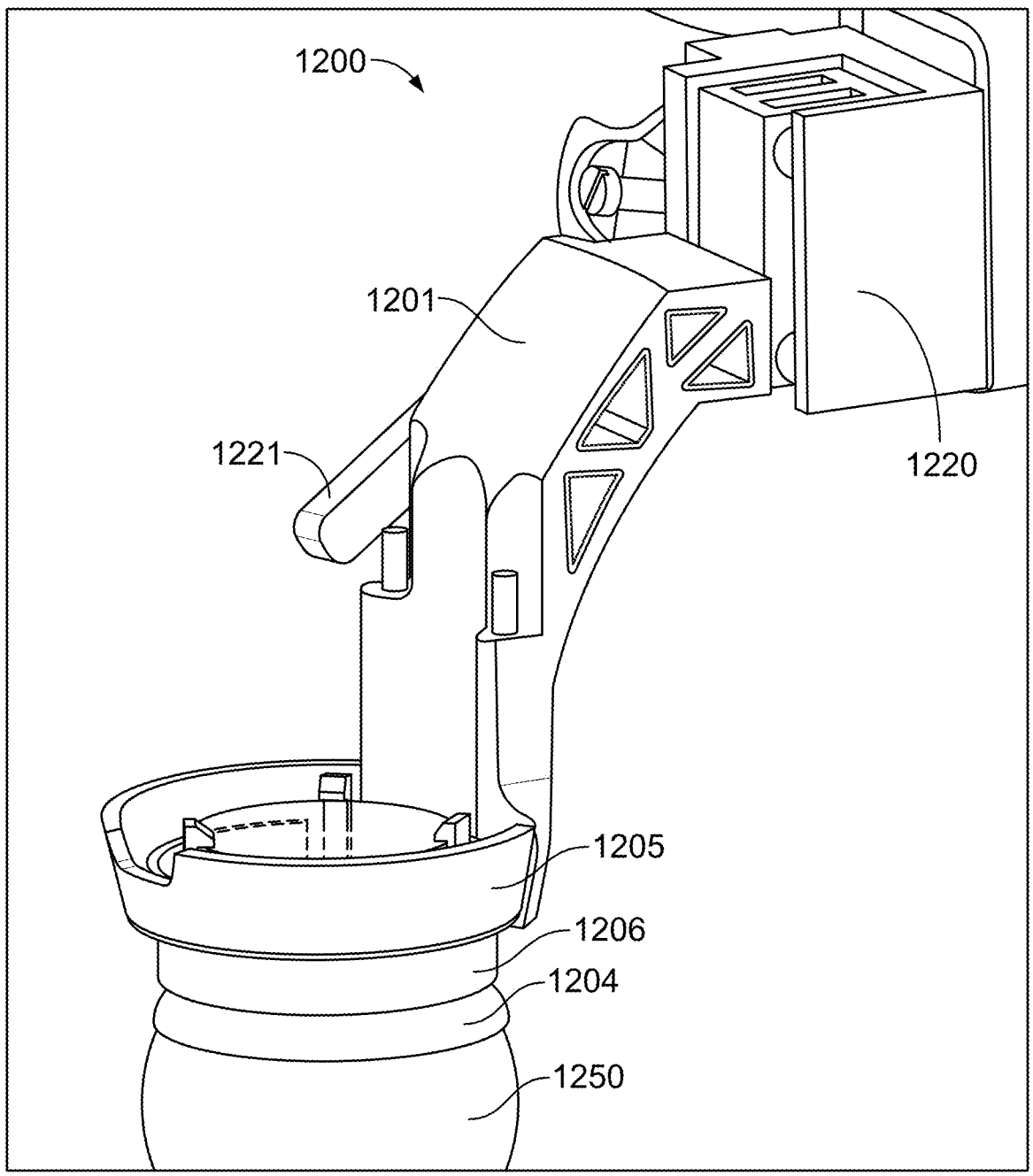
FIG. 12A is a perspective view of an embodiment of a patient interface device (PID) in accordance with the present inventions.
Figure 12B:
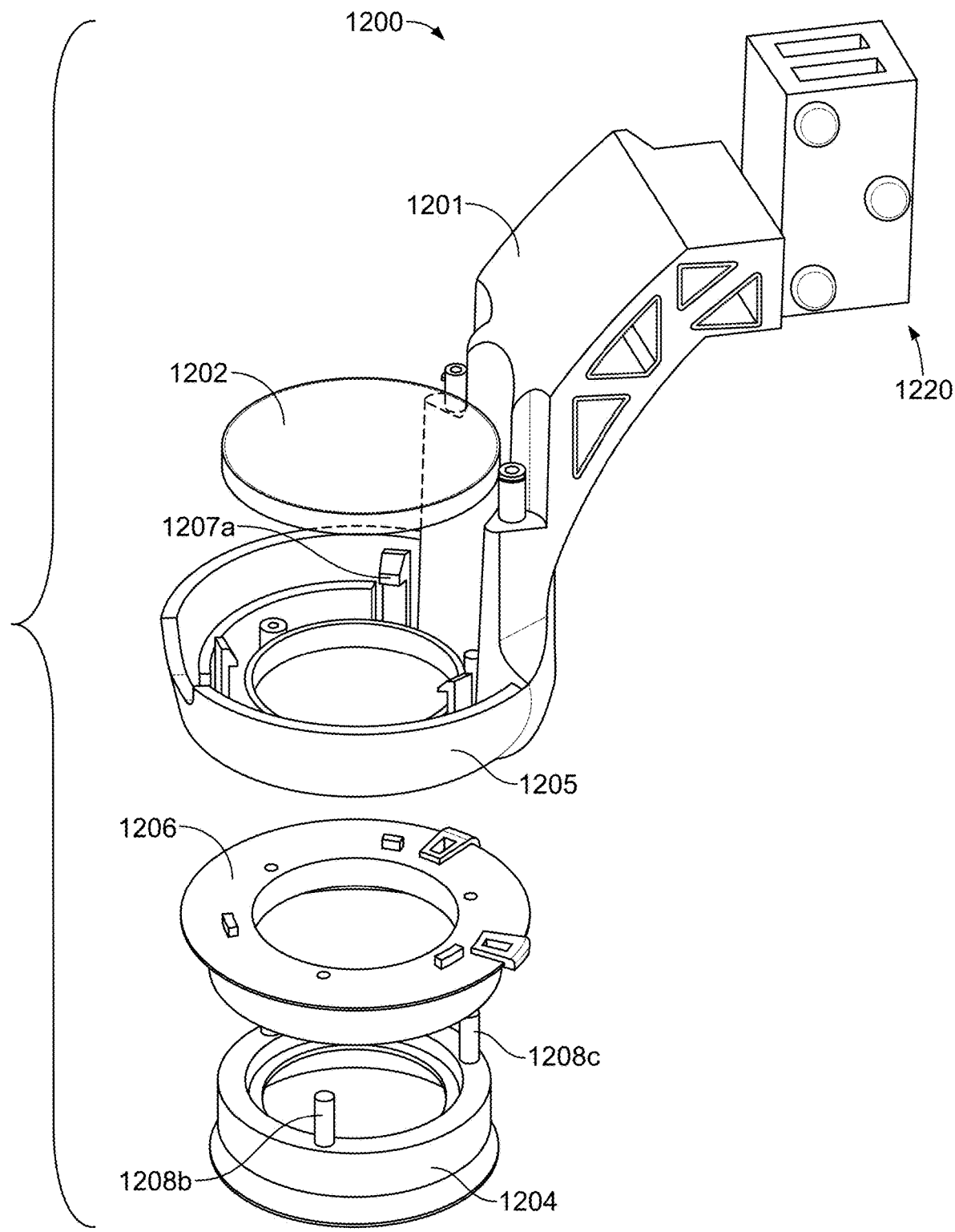
FIG. 12B is an expanded perspective view of the PID of FIG. 12A.
Figure 12C:
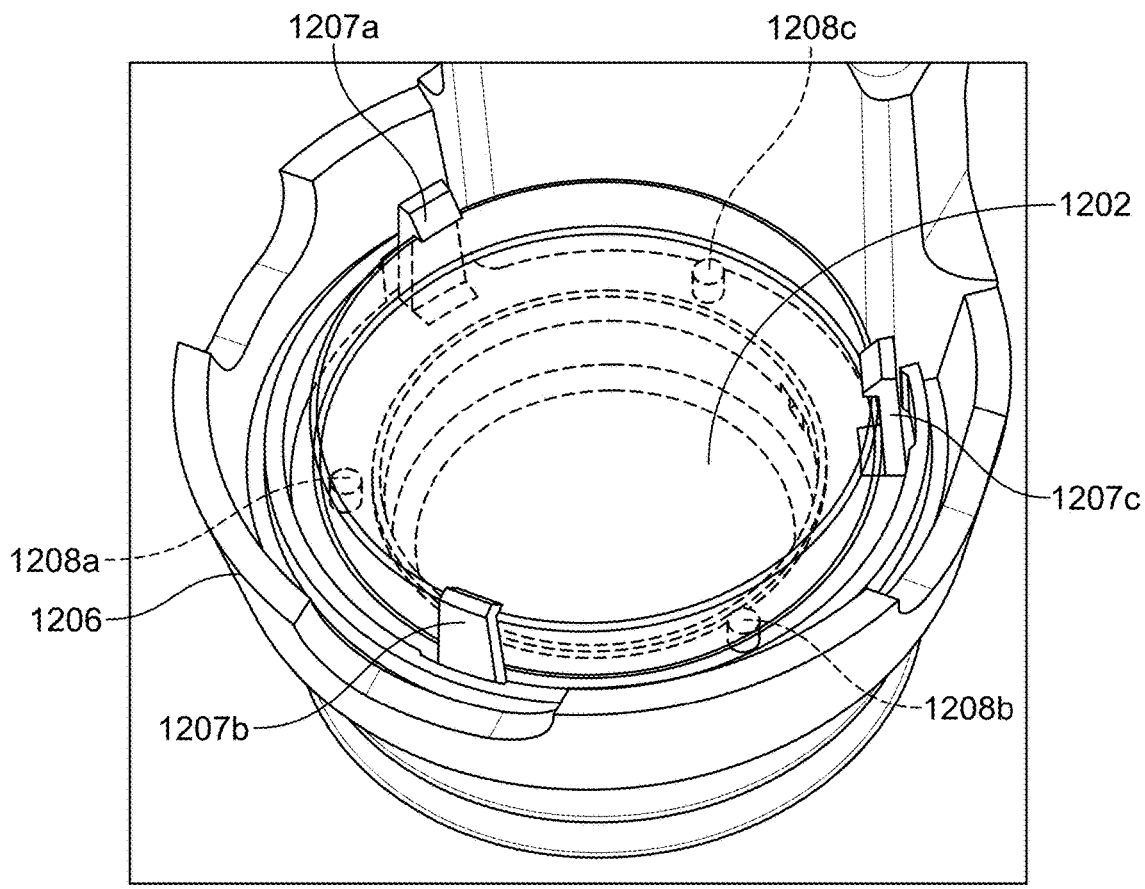
FIG. 12 C is a top perspective view of the PID of FIG. 12A.
FIG. 12D is a cross sectional view of the PID of FIG. 12A.
FIG. 12E is a perspective view of the PID of FIG. 12A.
FIG. 12F is a cross sectional view of the PID of FIG. 12A.
FIG. 12G is a perspective view of the manner of attaching the PID of FIG. 12A to an embodiment of a laser-ultrasound system in accordance with the present inventions.
FIG. 12H is a perspective view of the attached PID of FIG. 12A to an embodiment of a laser-ultrasound system in accordance with the present inventions.
FIG. 12I is a perspective view of an embodiment of the locking mechanism for attaching a PID to an embodiment of a laser-ultrasound system in accordance with the present inventions.
FIG. 12J is a perspective view of the locking mechanism of FIG. 12I, viewed from a different side.
Figure 12D:
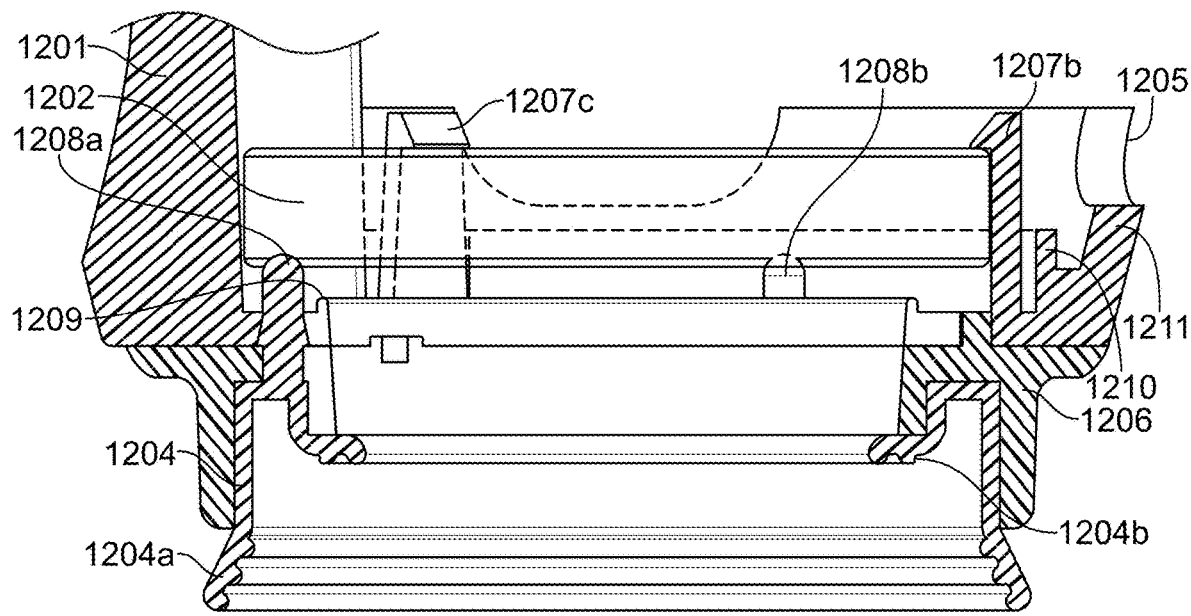
Figure 12E:
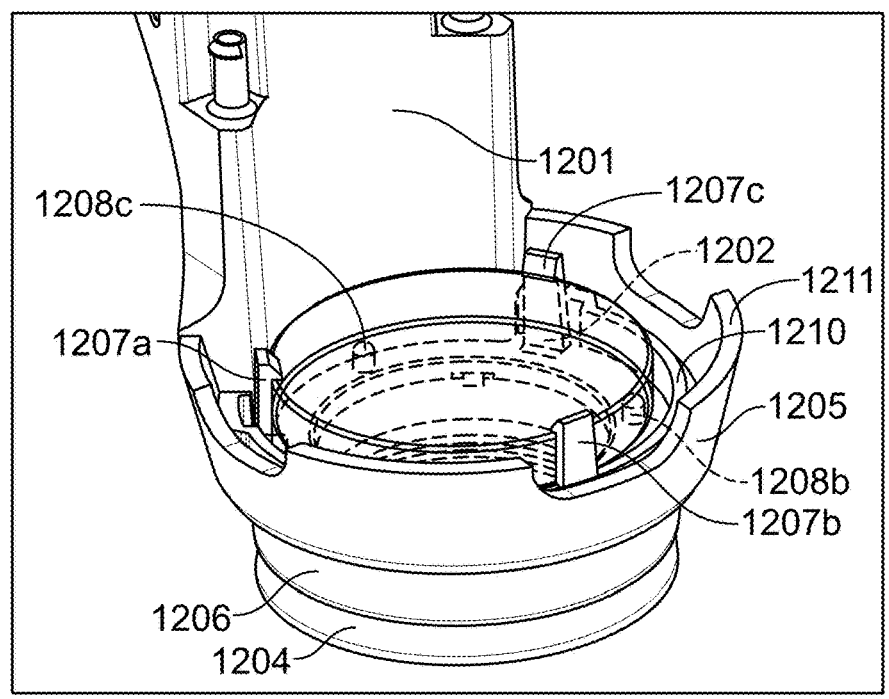
Figure 12F:
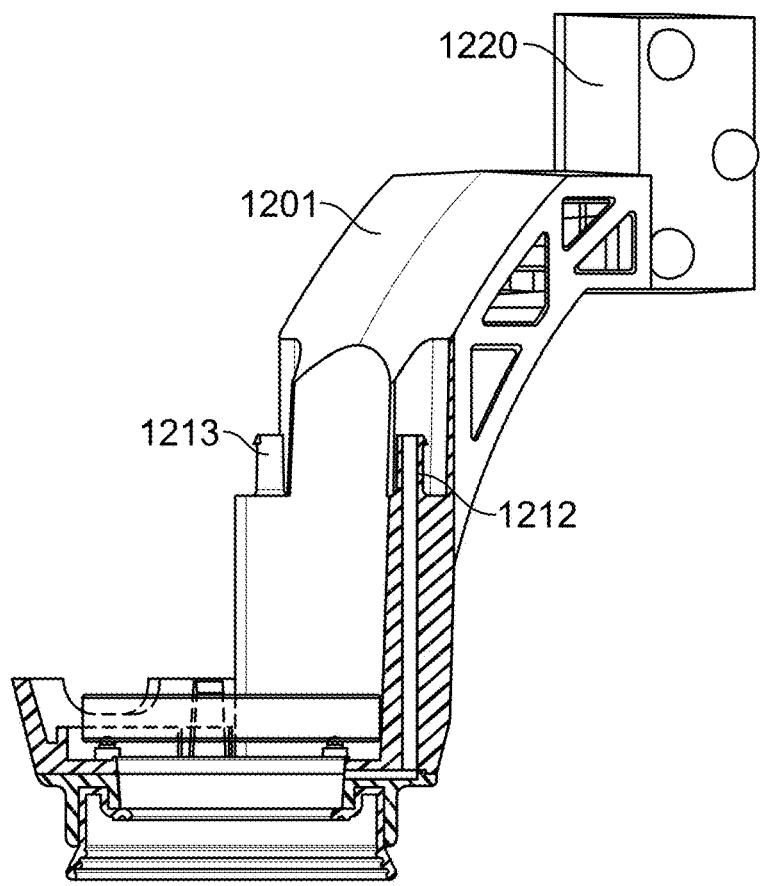
Figure 12G:
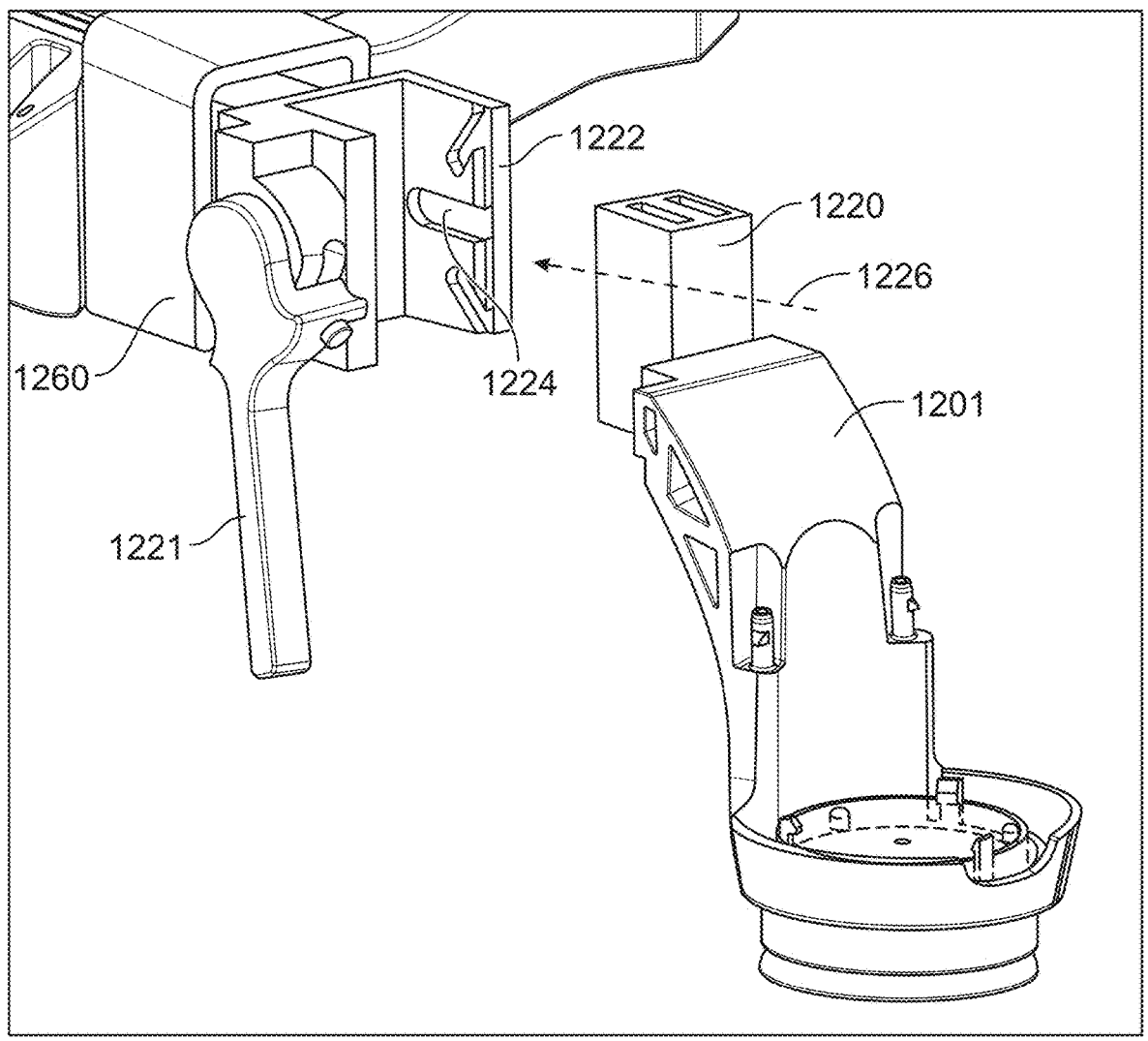
Figure 12H:
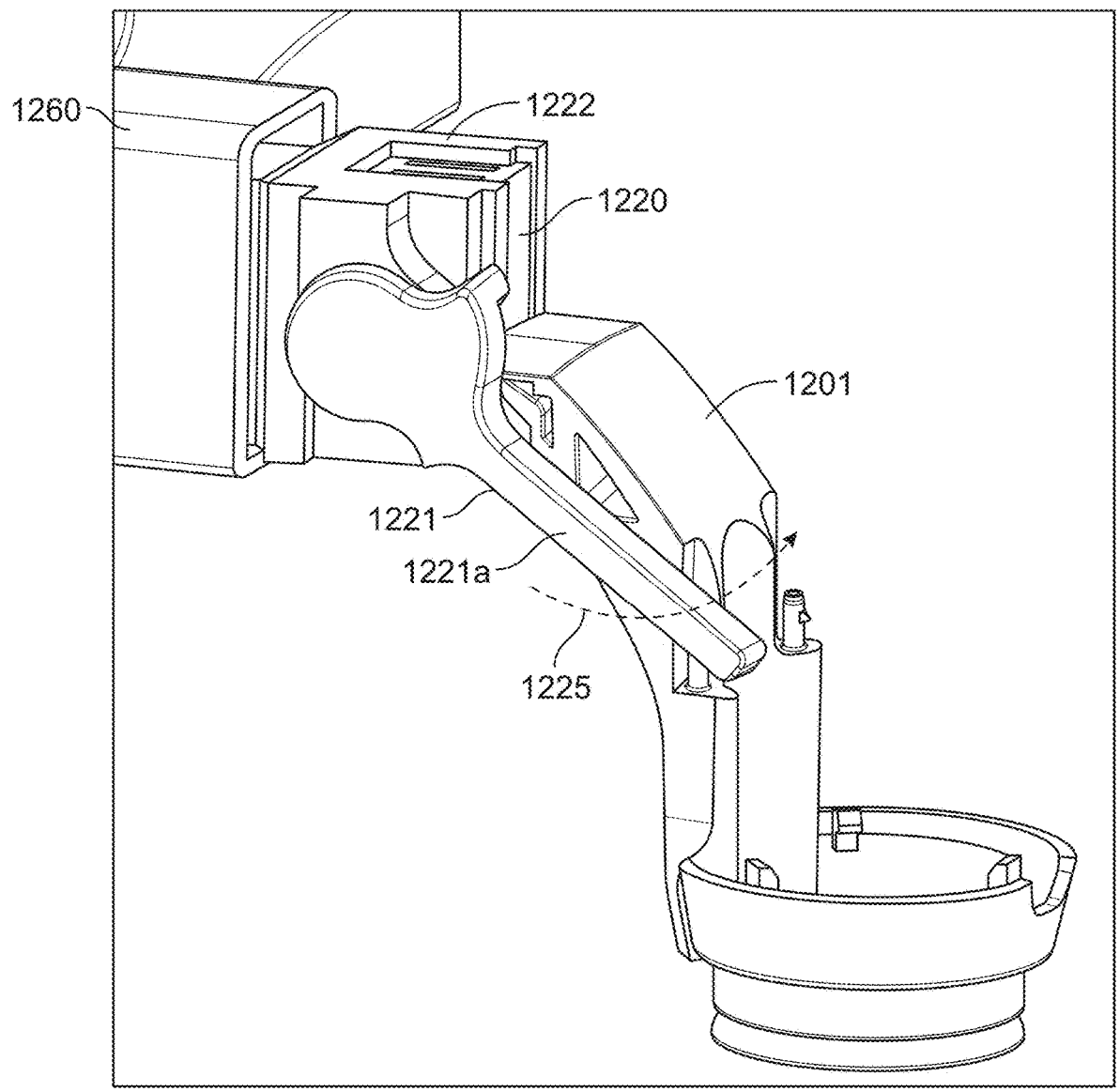
Figure 12J:
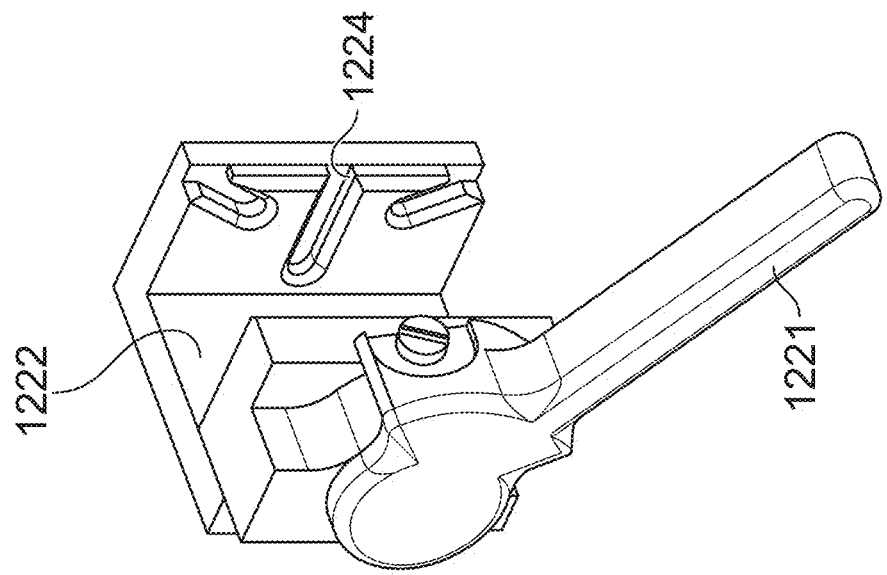
Figure 12I:
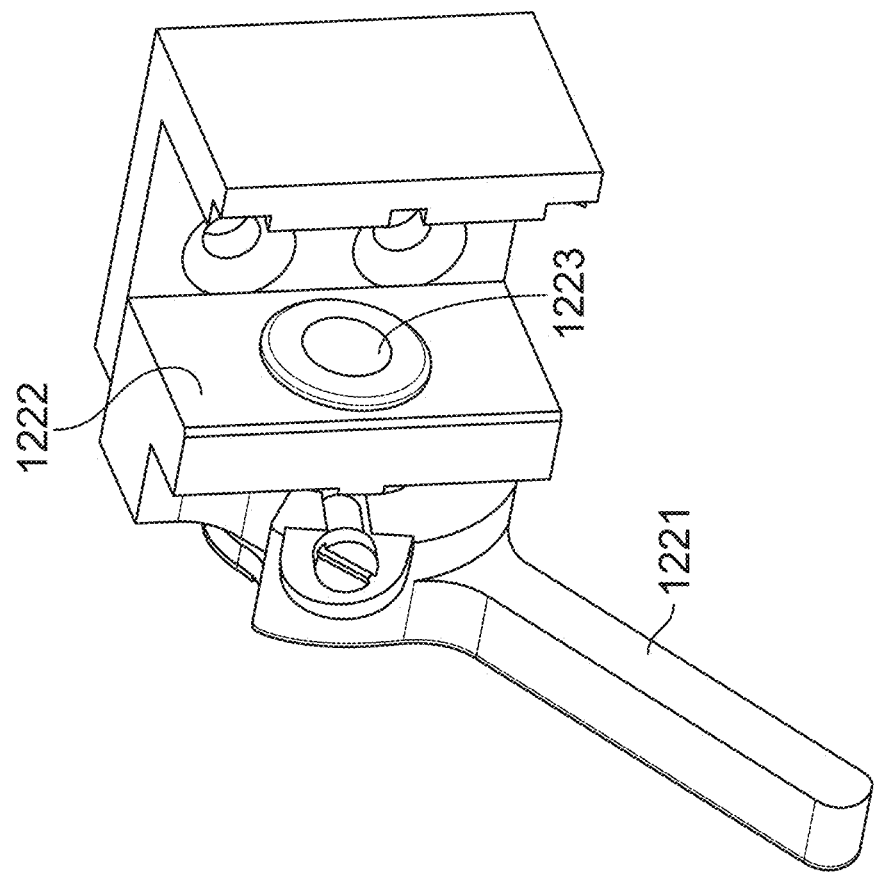

Turning to FIGS. 10A and 10B there are shown different angle views of prospective views of a proximal laser assembly having a docking system. In FIG. 10B the cover of the head is removed showing the Scheimpflug cameras, e.g., 1001*a*. The proximal laser assembly 1000, is attached to the proximal end of arm 1040, which is a light pipe that houses the therapeutic laser beam path, and laser beam during operation. The assembly 1000 has an automated docking system 1010, which has a drive assembly 1011 that is connected to a docking ring 1020 that docks to and forms a part of the PID. The docking system 1010 is preferably controlled by the control system, and can be operated, in whole or in part, by the surgeon using a joy stick. The control system also controls the operation of the docking system, and can have load sensors, speed control, and other safety and control systems.

Example 28

Embodiments of the therapeutic laser beams for use in the present systems and therapies have high quality beam properties. The laser beams can have an $M^2$ factor of from 1 to about 2.5, less than 2, less than 1.5 and less then 1.2.

Example 29

In embodiments of the present system the transition for femto to phaco, which includes the undocking of the laser, moving the laser arm out of the way, and having the phaco tool ready for insertion (and in embodiments also the insertion of the phaco tool into the eye), can take less than 5 mins (minutes), less than 4 mins, 3 mins and less, 2 mins and less, from about 3-5 mins, from about 3-4 mins, from about 2-4 mins, and longer and shorter times.

Example 30

In an embodiment the bed arrangement degrees of freedom, for a femto-phaco system having a 32×22 inch foot print allows the device to be position anywhere around the patient, who is 6' 3" and shorter. This system provides a truly ambidextrous system. This ambidextrous system provides for full clocking of the laser around each eye, and temporal and superior approaches by the surgeon.

Example 31

The laser system related components of the various embodiments, such as the embodiments of the Examples, are used in a stand alone laser system, that does not have a phaco system integrated with it.

Example 32

In an embodiment of these devices the floor area footprint, i.e., the device envelope formed by the outer housing, is 5 sq ft (22 in×33 in=726 sq in/144=5 sq ft). The height of this device is from 57 in to 65 in. The laser arm and its optics head primarily move horizontally. The arm does not rotate about a pivot point. In storage the arm fits entirely within the device envelope (i.e., 22 in×33 in). The laser arm and its optics head travel a maximum of 33" in "X" for initial setting of the nominal position. Once in the nominal position, the motion platform can move +/−2" in X, +/−2" in Y and +5/−3" in Z, for fine adjustment with respect to the patient. (As used in this example, X is the device long axis, Y is the device transverse axis, and Z is the device vertical axis.) Thus, in this embodiment the arm moves in X- and Y such that in storage the entirely of the arm and its optics head fits within the device footprint. The housing is not adjustable and thus its width and transverse dimensions do not change.

Example 33

Figure 14:
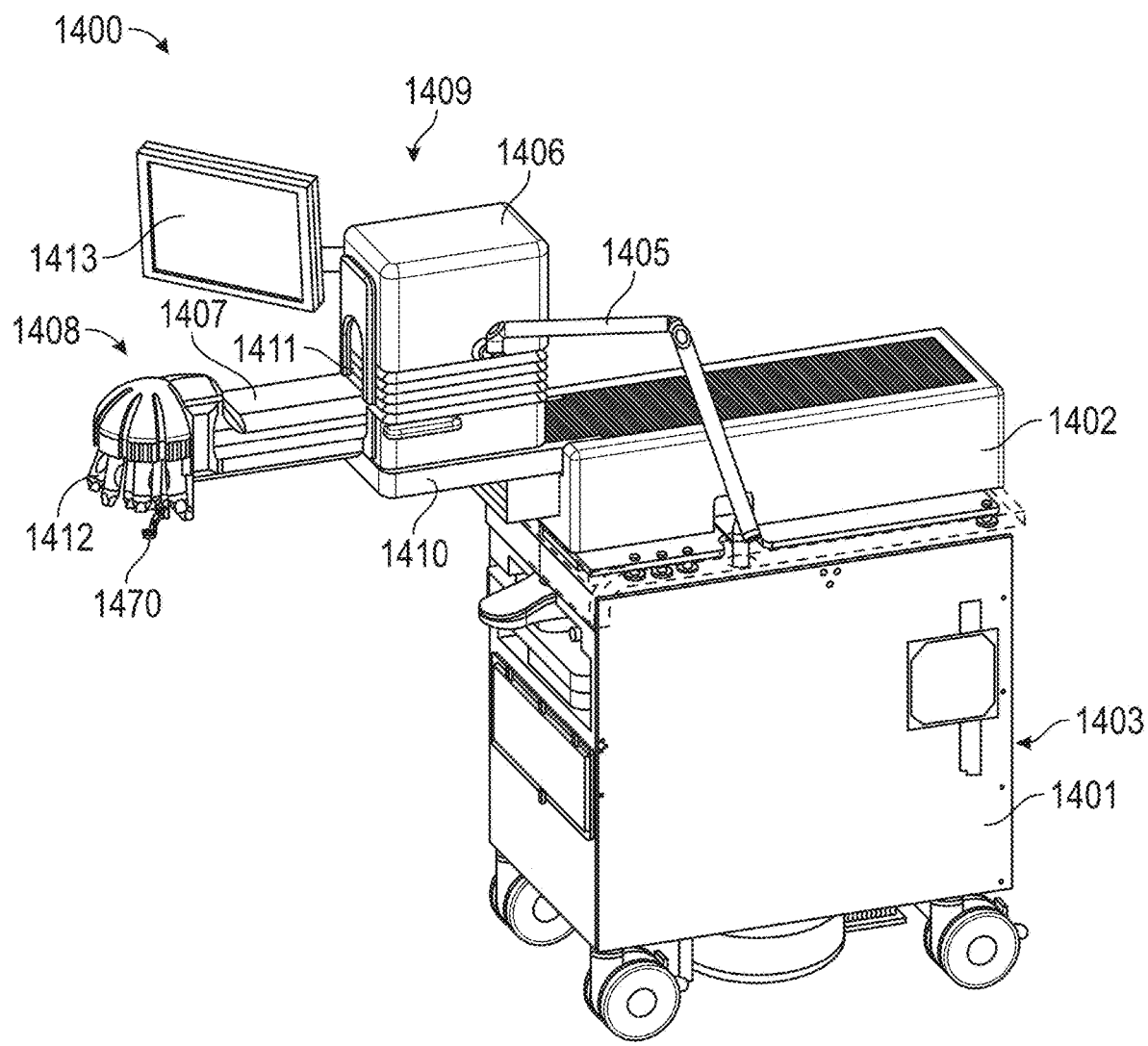
FIG. 14 is a perspective view of an embodiment of a femto-phaco system in accordance with the present inventions.

Turning to FIG. 14 there is shown a perspective view of an embodiment of a femto-phaco system 1400. FIGS. 15, 15A, 15B, 16A, 16B, 16C, 17A, 17B, 17C, show various components and configurations of the system of FIG. 14. Like numbers in these figures references to like components.

Femto-Phaco laser system 1400 has a housing 1401 that forms a base 1403 for the system 1400. Above the base 1403 and attached to the housing 1401 is the movement mechanism housing 1402. Housing 1402 contains the mechanisms for horizontal movement (i.e., extension and retraction) of the extendable assembly 1409. A transitional sliding stage 1410 is extended and retracted by horizontal movement mechanism 1420. The transitional sliding stage 1410 supports the optical assembly and scanner housing 1406. This housing 1406 also contains the vertical movement mechanism 1425 and vertical movement transitional sliding stage 1411.

The extendable assembly 1409 includes the housing 1406, the arm 1407, which contains the various optical paths for the system as well as control cables, and the laser beam delivery head 1408. The laser beam delivery head 1408 includes the shape and position determining device 1412 and the PID 1470.

The system 1400 is shown with one monitor 1413, in FIG. 17. The system can have one or two additional monitors (shown in FIGS. 16A to 16C). The system can have an integrated microscope (not shown in these figures).

Figure 15:
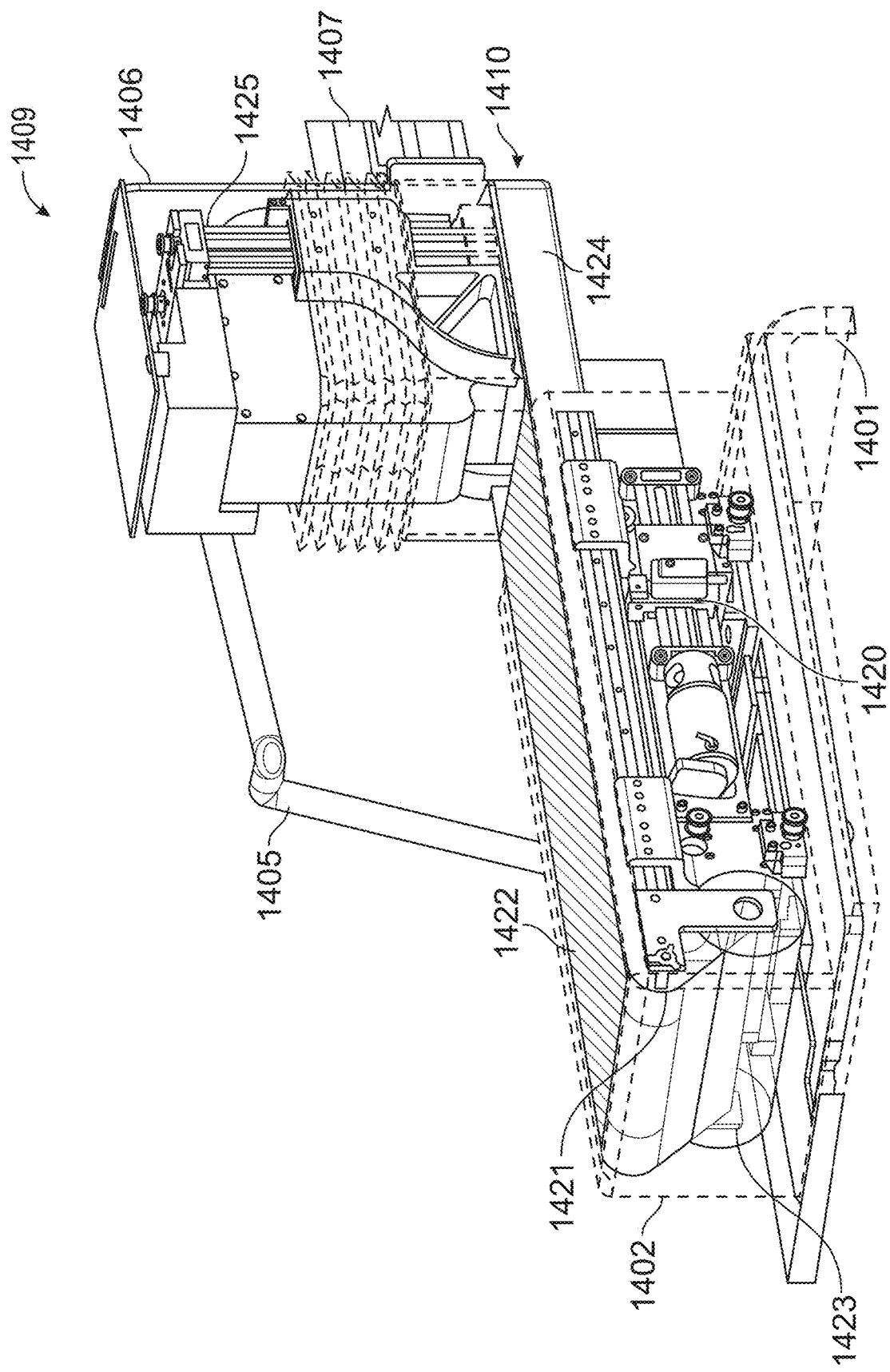
FIG. 15 is a transparent perspective view of a portion of the femto-phaco system of FIG. 14.

In FIG. 15, there is shown the extendable assembly 1409, which is attached to transitional sliding stage 1410. Stage 1410 has an extendable/retractable base 1424 and a flexible extendable/retractable cover 1422. Stage 1410 provides for horizontal movement of assembly 1409. Stage 1410 is positioned within housing 1402 and forms, in part, the top surface of that housing. The housing 1402 is attached to housing 1401.

Figure 15A:
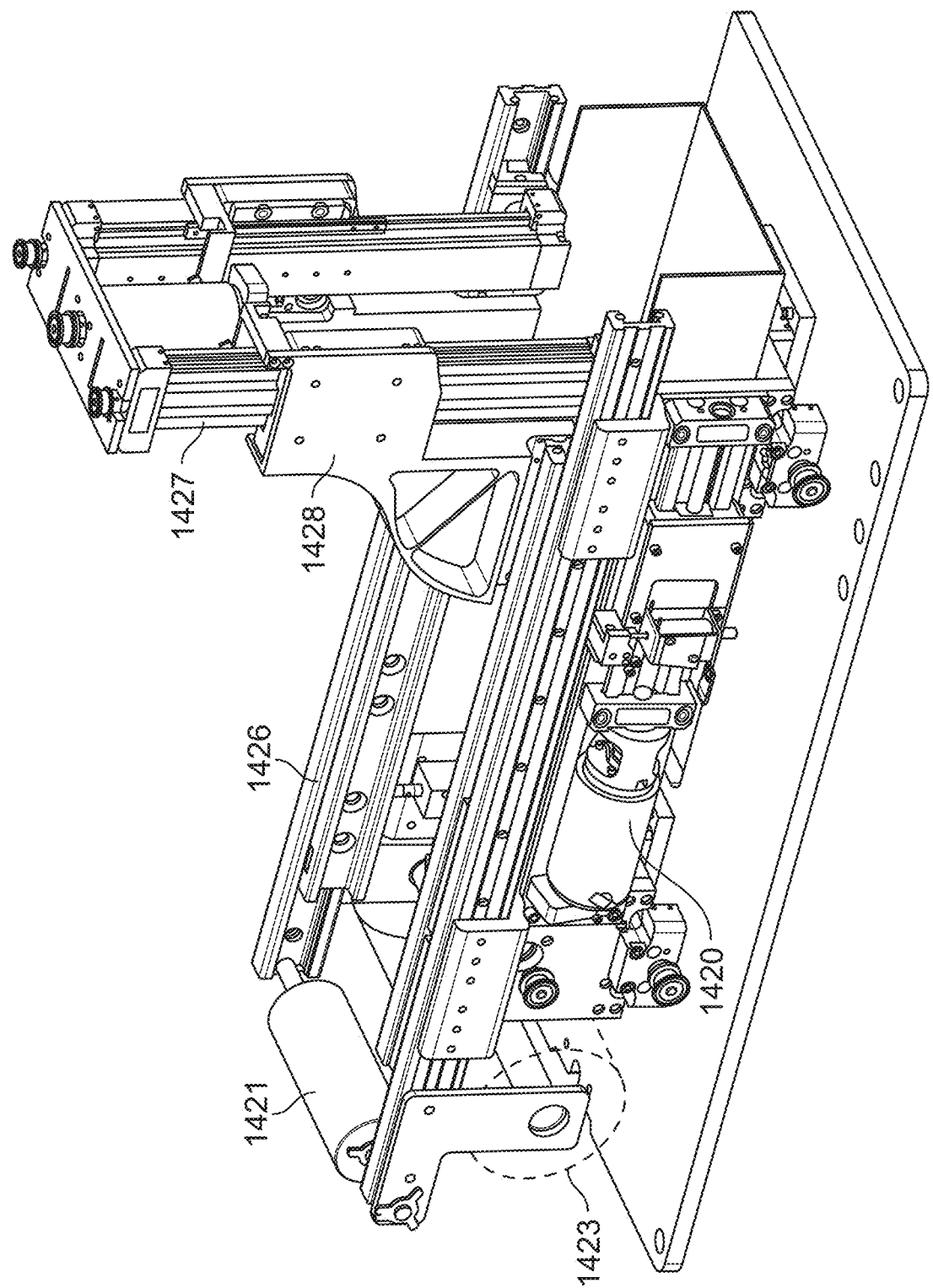
FIG. 15A is a perspective view of the horizontal and vertical movement mechanisms of the femto-phaco system of FIG. 14.

Turning to FIG. 15A, as well as FIG. 15, the horizontal movement mechanism 1420 is contained within housing 1402. The mechanism 1420 may be attached directly to housing 1402, to housing 1401 and combinations and variations of these. Housing 1402 also contains a reel 1423, which holds (i.e., winds and unwinds) the flexible cover 1422. The housing 1402 also contains a roller 1421 over which flexible cover 1422 moves.

Figure 15B:
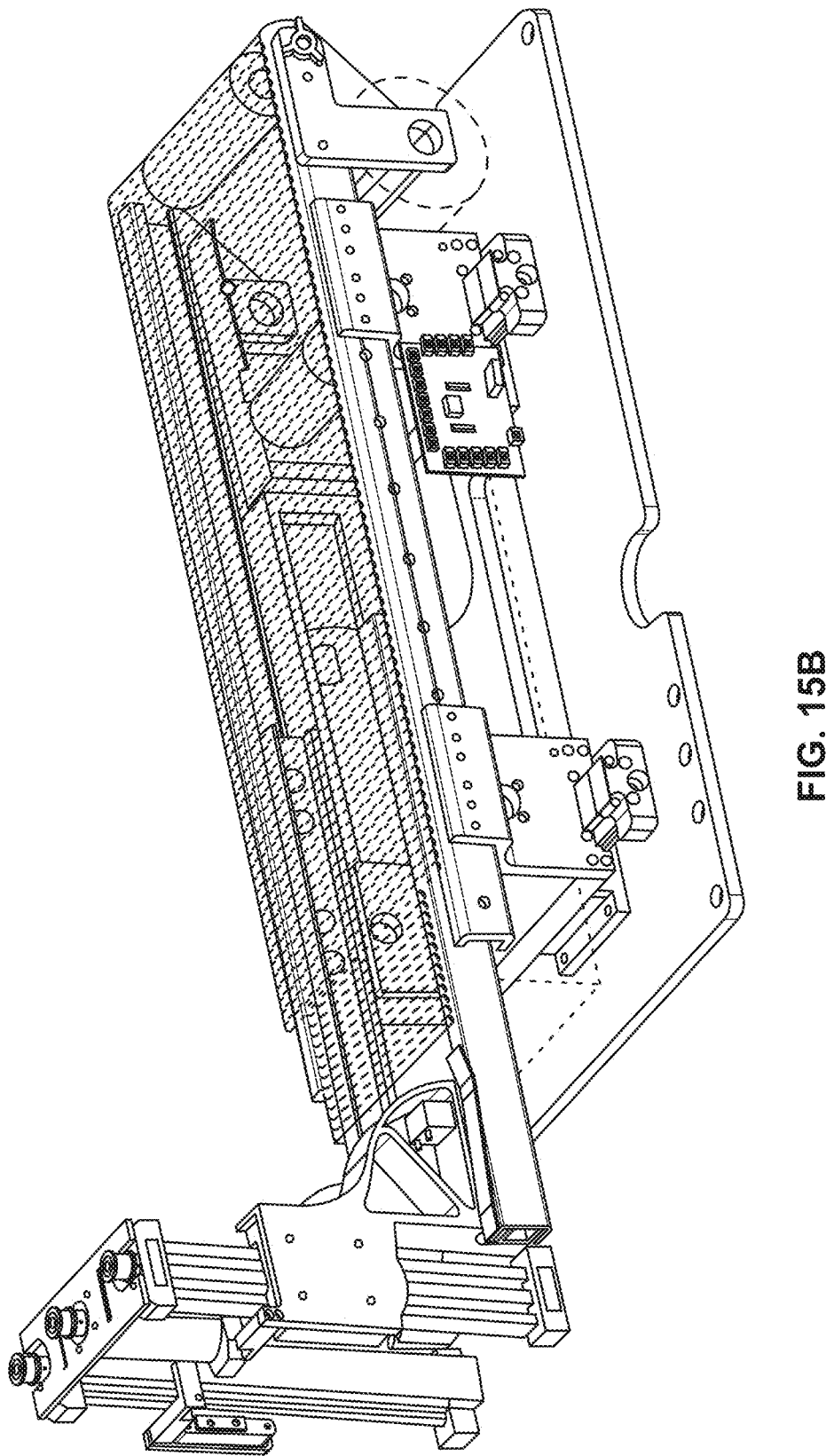
FIG. 15B is a perspective view of the mechanisms of FIG. 15A in an extended position in accordance with the present inventions.

FIG. 15A shows the horizontal movement mechanism 1420 with cover 1402 removed. The mechanism 1420 has a motor, drive mechanisms, sensors and controls. The mechanism 1420 has a horizontal slide mechanism 1426, which is a pair of sliding rails one inside the other. A support 1428 connects the inner rails with the vertical slide mechanism 1427, which slide mechanism forms a part of the vertical movement mechanism 1425 (see FIG. 15). FIG. 15B shows the rail assemblies of FIG. 15A in the first extended position, which is a position for conducting laser operations.

Figure 16A:
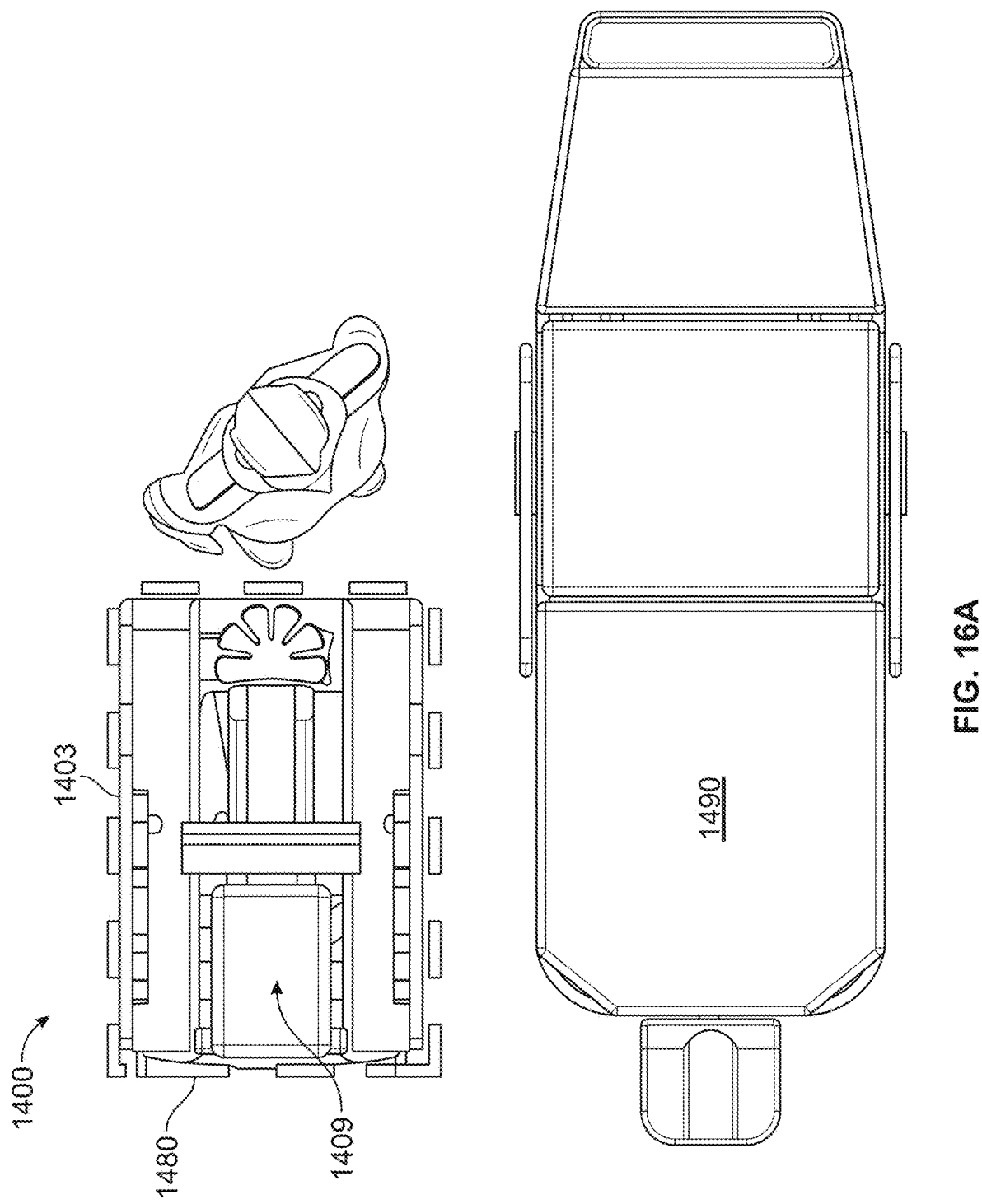
FIG. 16A is a plan view of the system of FIG. 14 in an operating room and in the fully retracted position in accordance with the present inventions.

FIG. 16A is a plan view of the system 1400 of FIG. 14, with 3 monitors. The System 1400 is located in an operating or patient treatment room, The system 1400 is in the fully retracted, e.g., parked, position. In the parked position the extendable assembly 1409 does not extend out from the base 1403. Thus, in this position the extendable assembly 1409 does not extend beyond (i.e., it is entirely within) the system's foot print or envelope, dashed line 1480. The system 1400 is shown in relation to a patient bed 1490 and a person.

Figure 16B:
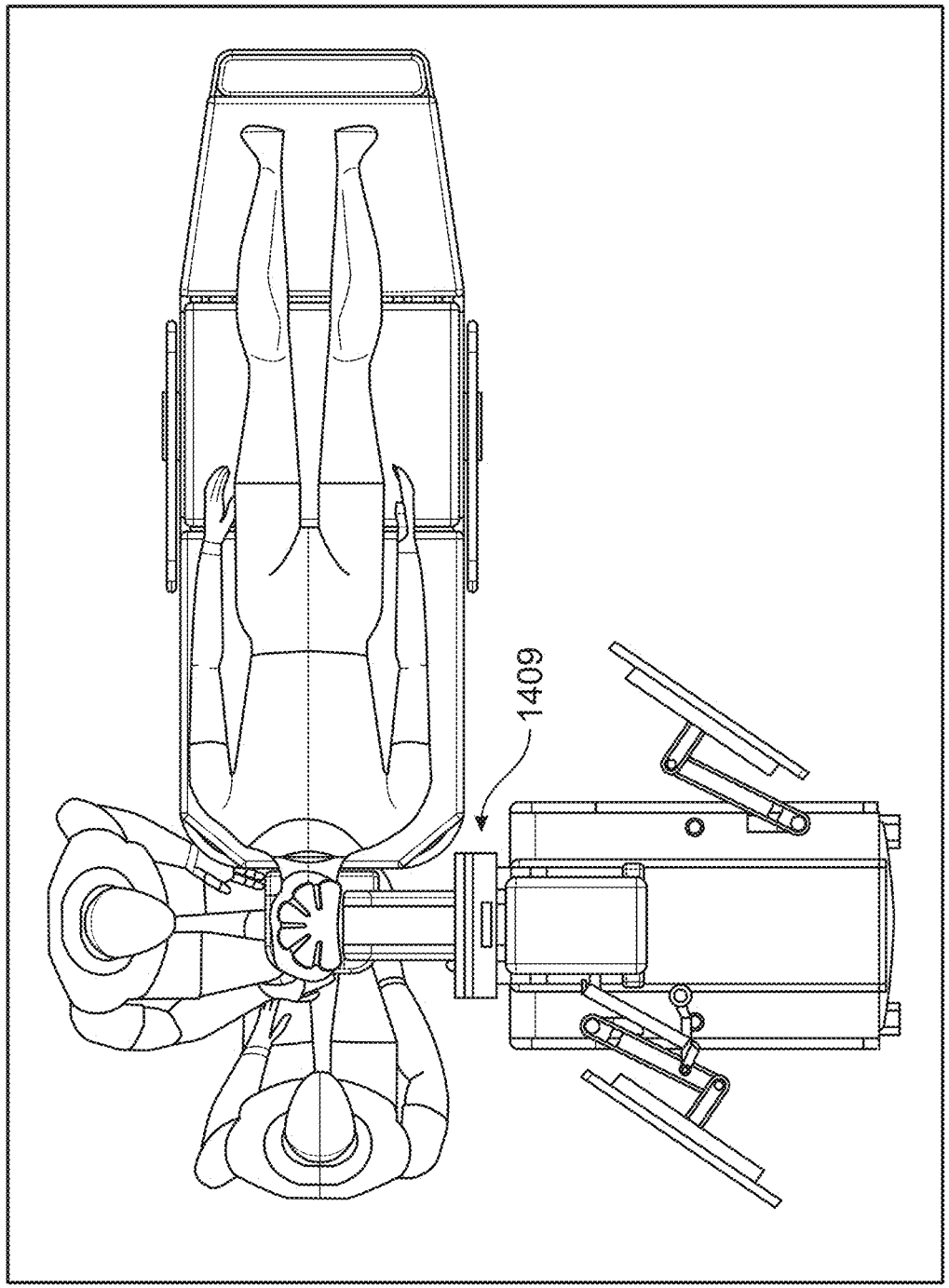
FIG. 16B is a plan view of the system of FIG. 14 in an operating room and in a partially extended laser operational configuration (first position) in accordance with the present inventions.

FIG. 16B shows the system in an extended position (the first position or first extended position) for performing a therapeutic laser operation. Although shown the system at a 90 degree angle of orientation to the patient, in is understood that this system can be positioned at any angle with respect to the patient. For instance, this system can be positioned at any of the angles of Examples 23 and 24. The extendable assembly 1409 is extend horizontally beyond the housing of the system to position the laser head over the patient.

FIG. 16C shows the system in the fully extended position for preforming a therapeutic laser operation. The system is shown at a 135 degree angle of orientation to the patient. The fully extended position maintains the house of the system far enough away from the patient to provide appropriate, comfortable and ergonomic access by the practitioner to the patient. The extendable assembly 1409 is extend horizontally beyond the housing of the system to position the laser head over the patient. Comparing FIG. 16C with FIG. 16B it is shown that the assembly 1409, in the fully extended position of FIG. 16C is longer, i.e., the laser head is further away from the base, than in the first extended position of FIG. 16B.

Figure 17C:
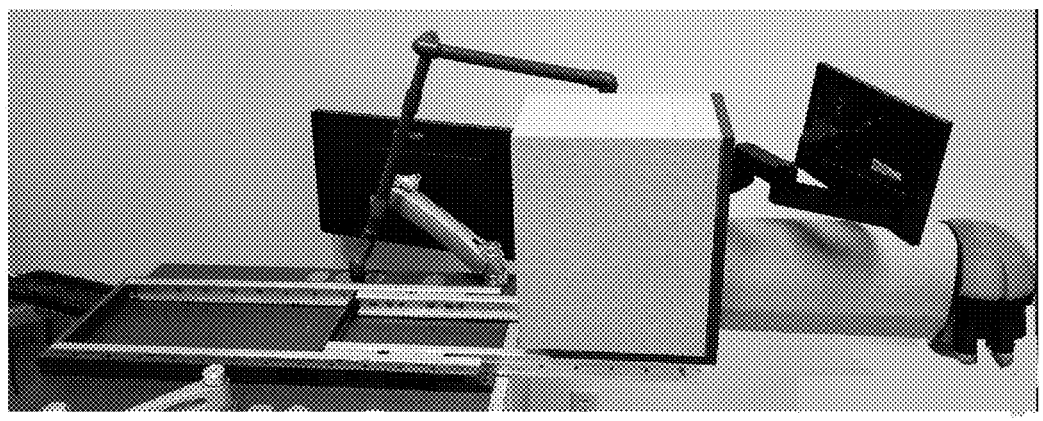
FIGS. 17A-17C are a sequence of photographs showing specific positions for the extendable assemble of the system of FIG. 14 as it is extended and retracted.
Figure 14A:
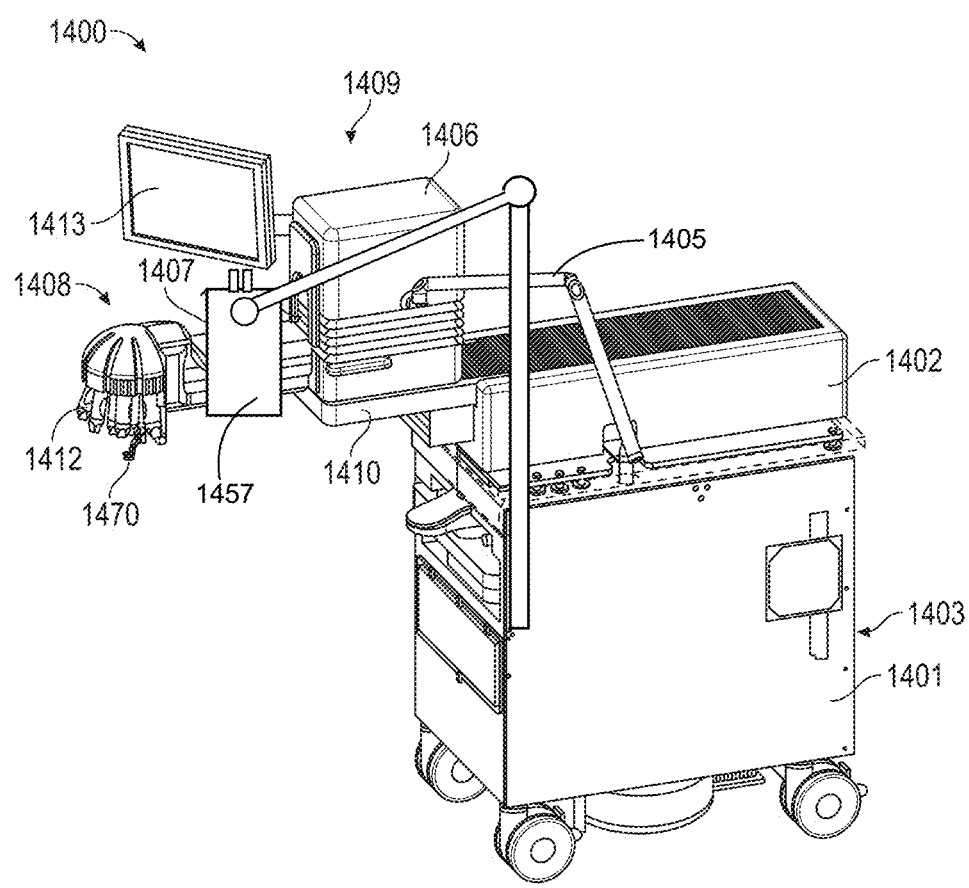
FIG. 14A is a perspective view of an embodiment of a femto-phaco system having a surgical microscope in accordance with the present inventions.
Figure 17A:
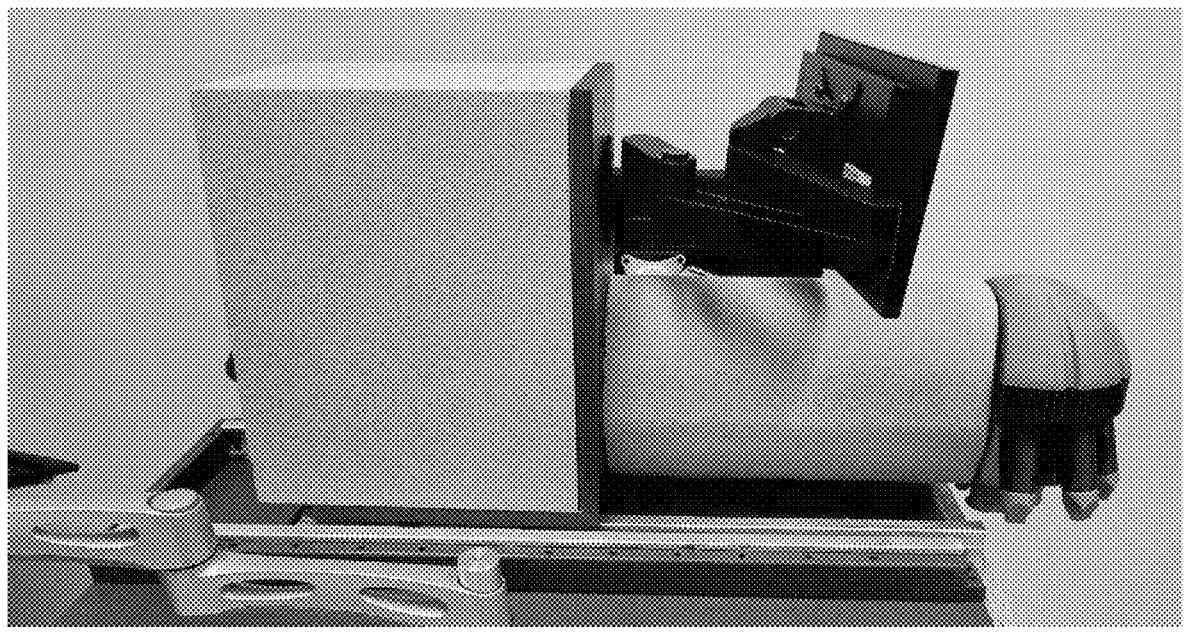
Figure 17B:
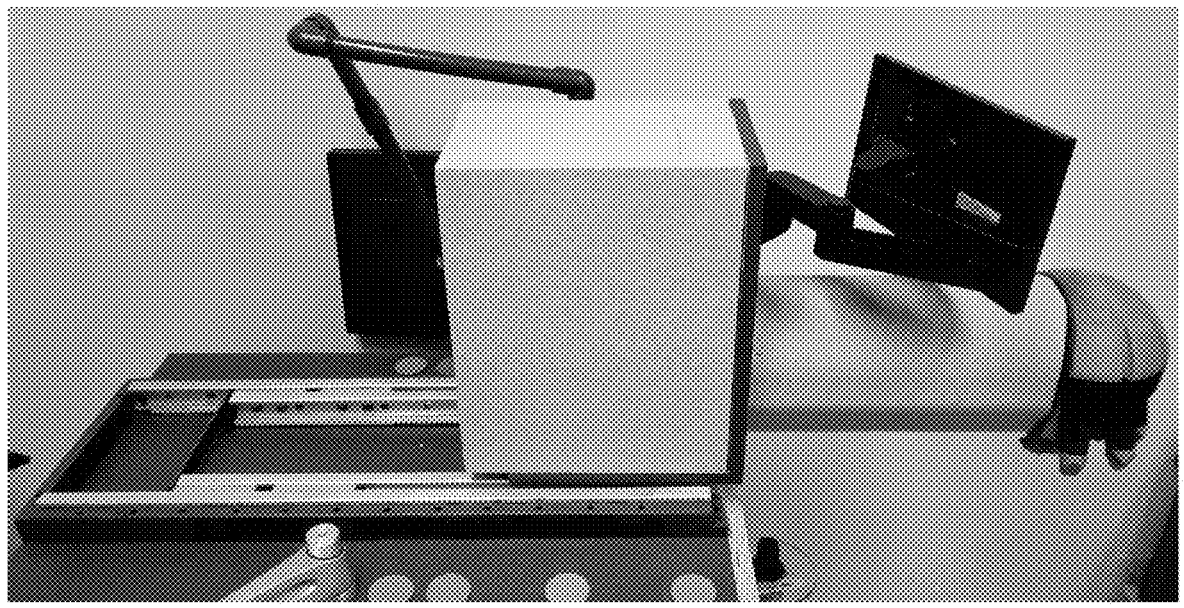

FIGS. 17A-17C are a sequence of photographs showing specific positions for the extendable assemble of the system of FIG. 14 as it is extended and retracted. FIG. 17A shows the neutral extended position for testing and calibration of the laser systems. FIG. 17B shows the first operational extended position for therapeutic laser operations. FIG. 17C shows the second operational extended position (fully extended) for therapeutic laser operations.

Thus, the system can have four predetermined positions. The parked position, where the laser head and the extendable assembly are within the device's footprint. The neutral position where only the laser head extend horizontally beyond the device's footprint. The first extended position where laser therapeutic activities can be performed on patients. The second or fully extended position where laser therapeutic activities can be performed on patients. The four predetermined positions can be controlled by stops, mechanical based, control software based and combinations and variations of these. The system may also be configured to have any number of other lengths of extensions from the neutral to the fully extended, either predetermined, or solely operator determined, and combinations and variations of these.

The housings contain power components, control components, operating components, analytic prediction and diagnostic devices, position deterring and location equipment, laser beam generation components, and ultrasound generation components. In a preferred embodiment the ultrasound generation components are components of a phacoemulsification system and the laser beam generation components provide a laser beam having a pulse length of about 2 ps, and shorter.

These components can be distributed, in whole and in part, between the two housings 1401, 1402, for among other reasons: to optimize space, to avoid interference between components, to manage heat and vibration, and to provide for more efficient control and operation of the system 1400. The two housings 1401, 1402 can be standalone housings, on the same base or frame, they can have communication, control, power, optical and other connections between them, they can be a single same housing, they can be subdivided or partitioned into a third or fourth, etc., housings or sub-housings, and combinations and variations of these.

There connector 1505 is an optical conduit that connects housing 1401 with housing 1406. Housing 1406 contains the scanning devices and beam shaping optics for the therapeutic laser beam, which scanning devices, optics and both, can also be used for monitoring and diagnostic laser beams and optical paths. (Housing 1406 also contains the vertical movement mechanism.) It being understood that in embodiments these components of housing 1406 can be located in whole or in part in one of the other housings, and likewise, components from the other housings can be located in housing 1406. Housing 1406 can be subdivided or partitioned into one or more housings or sub-housings, and combinations and variations of these. In a presently preferred embodiment housing 1406 contains and isolates the scanners and beam shaping optics. The scanner and beam shaping optics, or other components that may be contained in housing 1406, are in control communication with the controllers and operating systems of the system 1400. The devices may be in direct control communication with each other, or they may be in indirect control communication with each other, such as for example, by being in control communication with a central, e.g., the system 1400 controller, the monitor 1413, which may also have control capability and combinations and variations of these. These devices may also be in both direct and indirect control communication with each other.

The optical conduit 1405 can be a light pipe (e.g., hollow tube or channel having an internally reflective surface so that the laser beam is transmitted through the free space within the hollow tube, the free space within the hollow tube can have a partial vacuum, have air at ambient, contain an inert gas, and combinations and variations of these), an articulated light pipe, a telescoping light pipe, a flexible light pipe, an optical fiber, one or more optical fibers, a hollow conduit, a beam guide and combinations and variations of these and other laser beam conveyance structures.

The housing 1406 is attached to arm 1407. The arm 1407, and the housing 1406 moves in the vertical direction by vertical movement mechanism 1425. The arm 1407 has an assembly or device 1412 for determining the shape and position of the eye and structures within the eye. The arm 1407 at its proximal end, i.e., the end furthest along the laser beam path, and thus furthest from the laser beam source, and below the device 1412, has a patient interface device (PID) 1470 The housing 1406 has monitor 1413. The monitor is movable on, for example, an articulated arm. The monitor can provide information, such as the procedure, conditions of the system, laser status, ultrasound status, cataract density, ultrasound setting, laser pattern setting, and can receive surgeon input and instructions. The monitor is in control communication with the system 1400 control system, the monitor may also contain part or all of the system 1400 control system. The monitor is in control communication with the laser control system and the ultrasound control system, either directly, through the system 1400 control system, through the monitor 1413, and combinations and variations of these. The monitor and its articulated arm may be located on other structures in the system 1400 or may be free standing. One, two and additional monitors may be used. The monitors may have 3D viewing or displaying capabilities.

The arm 1407 forms or contains a laser beam conveyance structure, such as a hollow tube that provides free space for the transmission of the laser beam. In embodiments the arm 1407 may contain a beam path in free space, or optical fibers for transmitting the laser beam to, for example a scanner, that is located at the proximal end of the tube instead of the distal end, i.e., the end near the housing 1406. The arm 1407 may also be, or contain, any of the laser beam conveyance structures of the types described for use as the optical conduit 1405. The tube may also contain optics. In the embodiment of FIG. 14, the arm 1407 contains a laser beam that is non-collimated, and thus the arm 1407 can be referred to as containing a laser beam and laser beam path that is non-collimated, in other words the arm 1407 contains, surrounds or houses "non-collimated space" along the laser beam path. The arm 1407 may house or surround collimated space, that is space where the laser beam on the laser beam path is collimated. It may house space that contains optics. It may house both collimated and non-collimated space. The arm 1407 in embodiments may pivot from a distal point, rotate, be telescoping, articulated and combinations and variations of these. The proximal end of the laser beam path in the arm 1407 contains mirrors or optics to direct the laser beam through the PID and to, and into, the patient's eye.

Example 33A

The femto-phaco system of Example 33 has a surgical microscope 1457. It being understood that the surgical microscope as depicted in this example, can be used with the other examples of systems, and other embodiments of systems in this specification.

Example 34

In embodiments the laser system has external, internal or both cooling.

Example 35

Turning to FIG. 12A to FIG. 12J there is shown a PID (patient interface device) attached to, and of use with, any of the present laser-ultrasound systems, and also for use with standalone laser systems. In FIGS. 12A to 12J like numbers correspond to like structures. The embodiment of the PID 1200 in this Example, and as shown in FIGS. 12A to 12J, has the following components:

1201 PID arm
1202 upper window
1204 eye piece;
1204a eye piece outer skirt
1204b eye piece inner skirt
1205 upper ring
1206 lower ring
1207a Snap
1207b Snap
1207c Snap
1208a bumper
1208b bumper
1208c bumper
1209 meniscus inverter
1210 reservoir ring
1211 upper ring side wall
1212 channel for saline fill
1213 vacuum port
1220 attachment block
1221 arm
1221a locked position of arm
1222 receiving clamp
1223 engagement ball
1224 slot (kinematic slot)
1225 arrow showing arm movement
1226 arrow showing block engagement movement
1250 eye
1260 laser-ultrasound device This patient interface device is attached to the eye as a single assembly. The entire device after being attached to the laser head is then position and engaged to the surface of the eye. The PID arm is attached to the laser system via a clamping mechanism.

During docking, the suction cup of the PID arm is gently positioned over the cornea surface such that the suction ring comes into contact with the surface of the eye, then the vacuum is activated to restrain relative motion of the eye thereby stabilizing its position with respect to the PID for accuracy laser treatment.

The 3 spherical features on PID arm to engage kinematic slot features on clamping mechanism. Spring force is applied on PID arm by the ball during engagement for location. Once the PID is in place, the lever activates a CAM mechanism to load a ball against the PID and lock the kinematic mount into place.

The suction cup interface or "eyecup interface" overlays the anterior surface of the eye and is attached to the eye. A glass window defines the first plane surface of the patient interface device. It's a positional reference to the first refractive surface used by the software algorithm to compute the precise location of the focal point of the light emanating from the illumination or laser beam.

The 3 snaps to hold the window. The 3 over mold bumpers push the window tight to the snap undercut. The fluid chamber of the PID arm is designed with a circular wall extended proximal to the windows. This allows the fluid meniscus to invert before making contact with the window during fluid chamber filling. Proper contact of the fluid with the window, that is, from the center of the window out to the peripheral, helps prevent bubbles to be trapped under the window, which could possibly cause disruption of the laser beam.

The fluid chamber of the PID arm is extended to a reservoir ring in which extra fluid from the chamber is discharged. This also acts as a barrier to prevent the saline solution (BSS) in the chamber from contacting the patient skin that could cause it to drain out by capillary action.

The PID arm has at its base a flexible attachment ring that is adapted to interface with anterior surface of a patient's eye. The attachment ring includes flexible annular outer and inner skirts made of silicon that engage the surface of the eye when the eyecup is affixed. The inner and outer skirts delineate an annular suction channel that serves for vacuum communication channel.

On the other aspects of the design, the PID arm has on its side a vacuum port that is used to generate suction force in the annular suction channel and enables eyecup interface to be neatly attached to the patient's eye. A second port next to the first is connected to medical grade tubing to fill up the eyecup interface chamber with saline solution (BSS).

Example 35A

Figure 13:
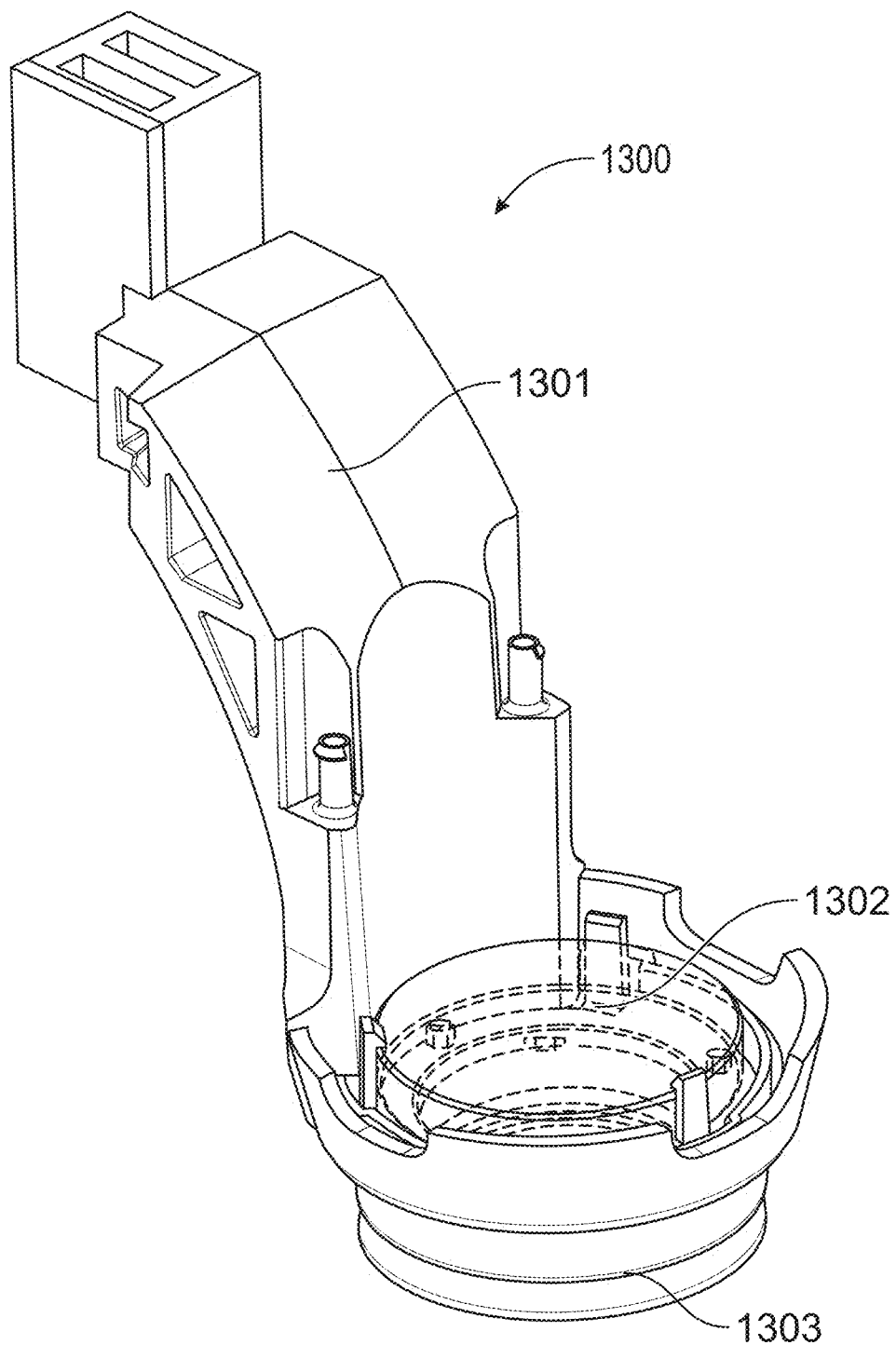
FIG. 13 is perspective view of an embodiment of a PID in accordance with the present inventions.

Turning to FIG. 13, there is shown a perspective view of a PID 1300. The PID 1300 has a PID arm 1301, an upper (distal) window 1302, which can be glass and preferably is highly transmissive to the therapeutic laser, and a lower (proximal) glass window 1303, which can be glass and preferably is highly transmissive to the therapeutic laser.

Example 36

Figure 18:
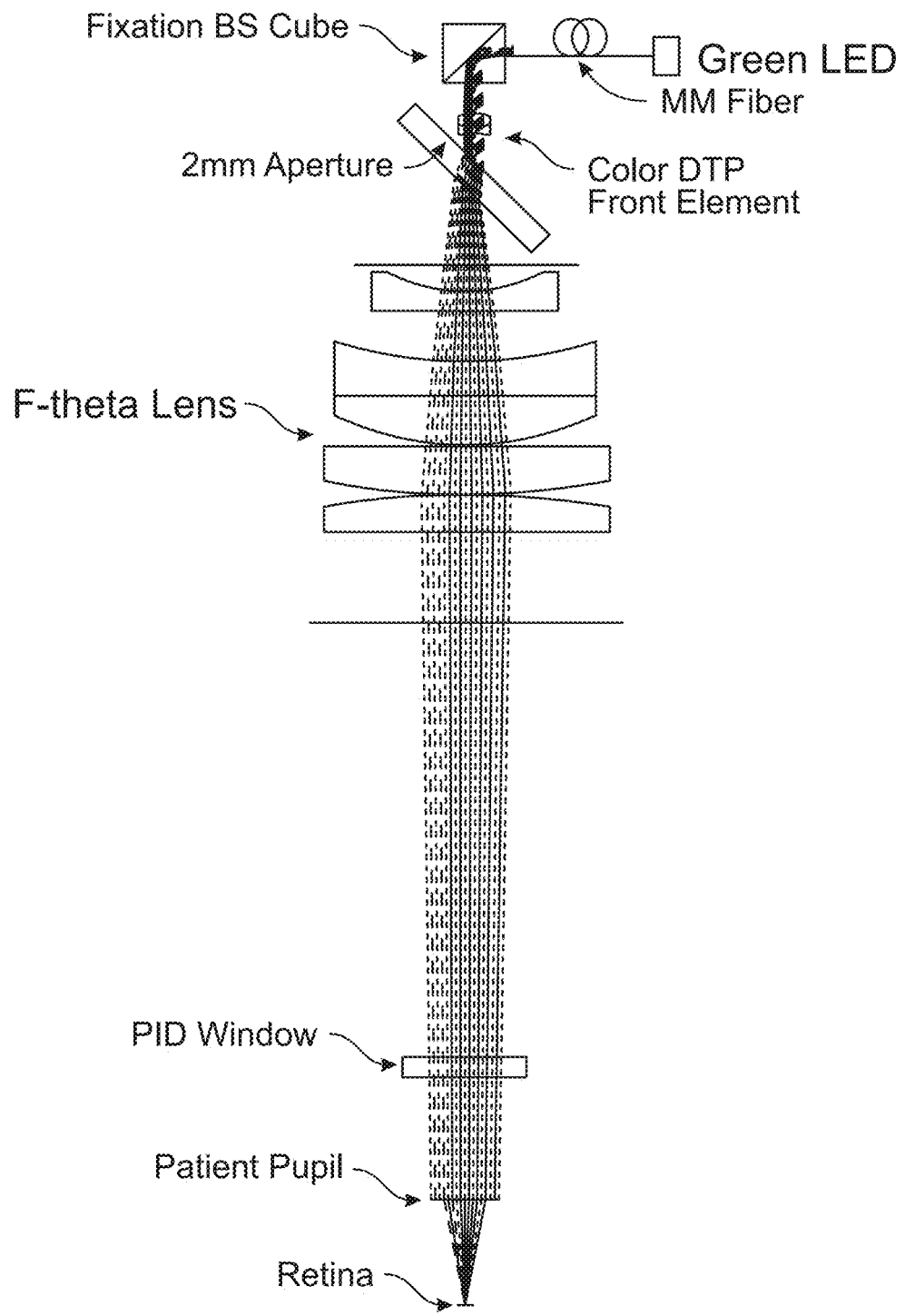
FIG. 18 is a schematic of an embodiment of a fixation optical path in accordance with the present inventions.
Figure 19:
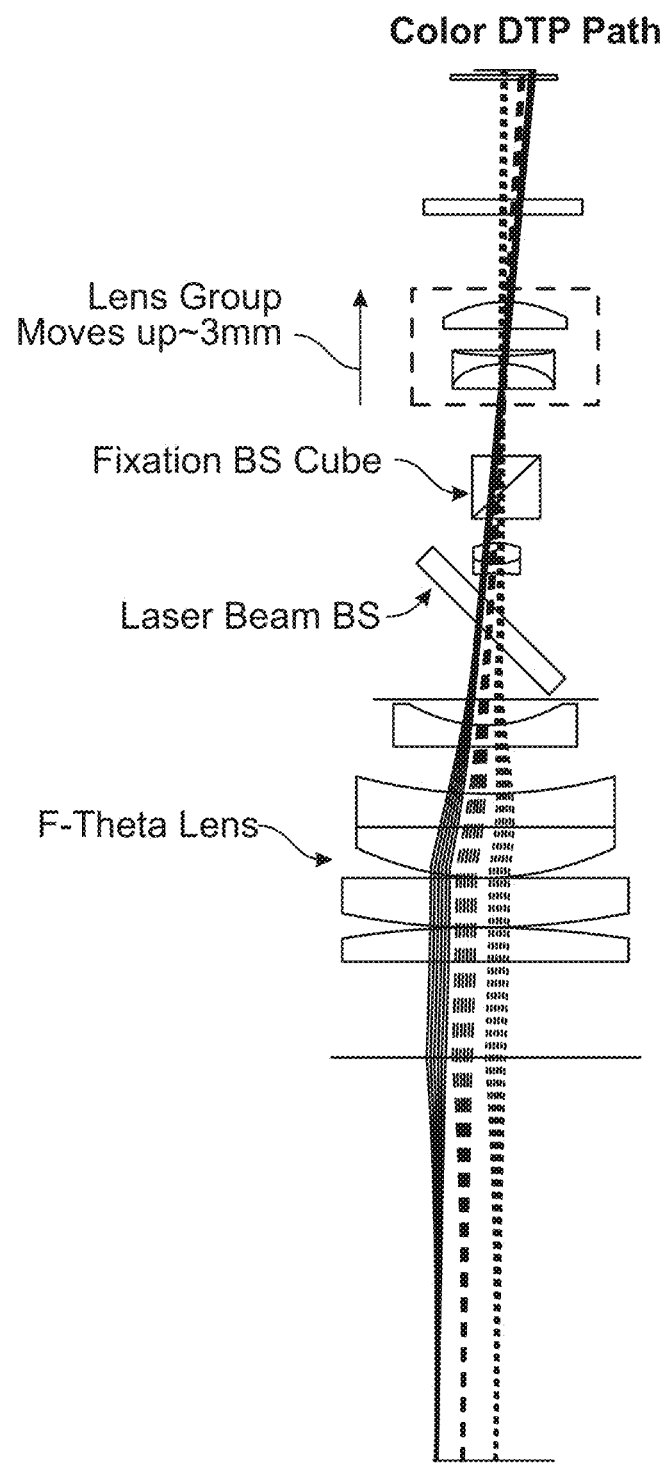
FIG. 19 is a schematic of an embodiment of a color down the pipe (DTP) optical path in accordance with the present inventions.

Turning to FIGS. 18 & 19 there are respectively shown for a fixation light optical assembly and path and a down the pipe (DTP), e.g., along a portion of the therapeutic laser beam delivery path to the eye, optical assembly and path for viewing the eye with a camera. In preferred embodiment the majority of the fixation light path and the DTP viewing paths are coincident.

Example 37

In an embodiment the laser-ultrasound system, e.g., femto-phaco system, has the laser configured for posterior capsulotomies, and laser operations on the posterior lens capsule. The system further has predetermined phaco parameters, that can be accessed and used, and are integrated with and optimized for the laser operations. The system can have a menu based control system through the use of a GUI having screens such as those shown in FIGS. 23A to 23D.

Example 38

The patient locator device system for the laser, laser-ultrasound, and femto-phaco systems can have self-contained markers that can be placed on the body, the head rest or both, and do not require line-of-sight for continuous tracking. Magnetic fields are generated by the markers and both position and orientation data are output, without the need for post analysis calculations. Accurate, high-quality data is delivered with an update rate of 50 Hz per marker. Adding markers (e.g., four per system). The system is further described in Table 2

TABLE 2

| | |
|---|---|
| Update Rate | 50 Hz/marker |
| Latency | Approximately 20 milliseconds |
| Static Accuracy | 1.0 degree and 0.3 inch (0.75 cm) using one marker and one receptor at 30 inches (76.2 cm). Accuracy is installation dependent, typical accuracy may normally result in 1 to 3 degrees and 1 to 3 inches (2.54 cm to 7.62 cm). |
| Operating Temperature | 10 C. to 40 C. at a relative humidity of 10% to 95%, noncondensing |
| Power Requirements | 100-240 VAC, 50-60 Hz, single phase, 4 W |
| Software Tools | GUI and SDK included USB drivers for Microsoft Windows ® included |
| Regulatory | FCC Part 15, class B CE: EN61326-1: 2013 EMC Requirements |
| Latency | Approximately 20 milliseconds |
| Static Accuracy | 1.0 degree and 0.3 inch (0.75 cm) using one marker and one receptor at 30 inches (76.2 cm). Accuracy is installation dependent, typical accuracy may normally result in 1 to 3 degrees and 1 to 3 inches (2.54 cm to 7.62 cm). |
| Operating Temperature | 10 C. to 40 C. at a relative humidity of |
| OPERATING TEMPERATURE | 10% to 95%, noncondensing |

Example 39

The laser, laser-ultrasound, and femto-phaco systems can have a surgical microscope integrated with the system. The microscope can be attached to the housing of the system, and preferably is integrated into the system. In this manner the microscope is in information, data and control communication with the systems control systems (e.g., femto-phaco control system). Thus, for example, the surgical microscope and system are configured for the microscope to accept commands, and views (digital overlays) from the therapeutic laser system, and in particular optics and data system, this communication takes place in the laser, e.g., femto mode, during the laser procedure, e.g., femto procedure, during the phaco mode, e.g., during the phaco procedure, during an idle, warmup or observation mode (phaco, laser or both active but no procedure being performed) and combinations of these.

In an embodiment the surgical microscope is replaced, or augmented, by a 3D vision system. The 3D viewing system can be any system that displays to the surgeon, or other practitioner, or observer, a three dimensional image of a structure of the eye, including for example the cornea, the lens, the PID interface and contact with the eye, the IOL, and combinations and variations of these and other structures and devices. The 3D viewing system can be for example, a wearable 3D attachable aid (such as the BEYEONICS Surgical device), a 3D monitor, a monitor and glasses-based system, a heads up display system and combinations and variations of these. The 3D viewing system can record the procedure in 3D and can provide remote 3D images of the procedure, real time, to a remote, e.g., different location, from where the laser system is located.

Example 40

The laser, laser-ultrasound, e.g., femto-phaco systems can have a "smart" foot switch associated with the system. The foot switch is integrated with the system control system. The foot switch can turn on and off the laser and the phaco, based upon the mode of the system. The foot switch can be integrated with the menu system, GUI and voice commands, in a manner that allows the foot switch to be used to select procedures, e.g., menu driven items on the GUI, susch as the memu items shown on FIGS. 23A to 23D. The foot switch can also be integrated with a speaking and listening control and menu selection system, such as "ALEXA", or other type of voice command system.

The footswitch can be wired, i.e., have a control cable connecting the footswitch to the laser-phaco system. Preferably the footswitch is wireless and is in control communication with the control systems for the laser, the phaco, the integrated unit, one or more of these, and all of these.

Figure 22:
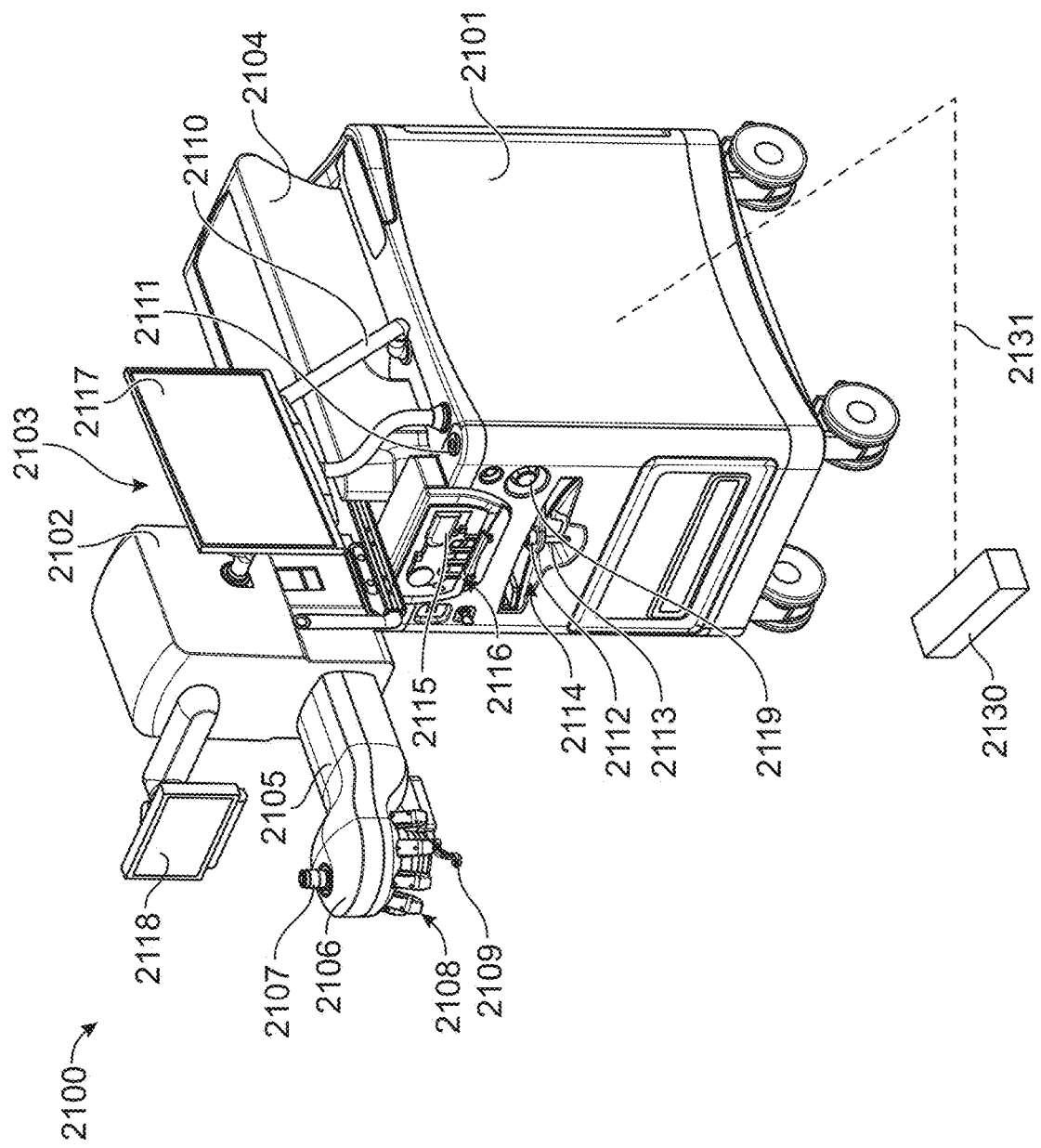
FIG. 22 is a perspective view of an embodiment of a femto-phaco system with a wireless footswitch in accordance with the present inventions in an extended position.
Figure 22A:
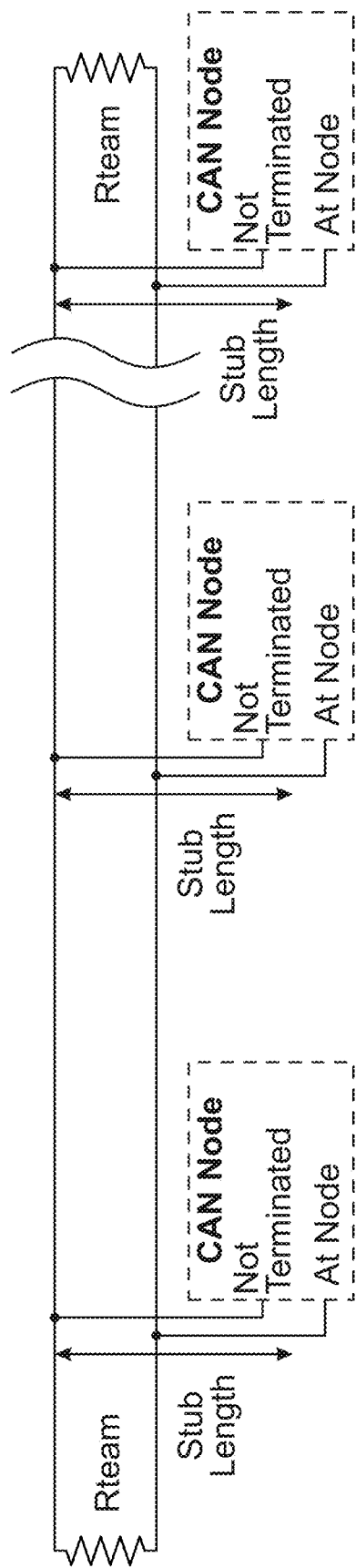
FIG. 22A is a schematic of a control bus for a femto-phaco system of FIG. 22 in accordance with the present inventions.
Figure 23A:
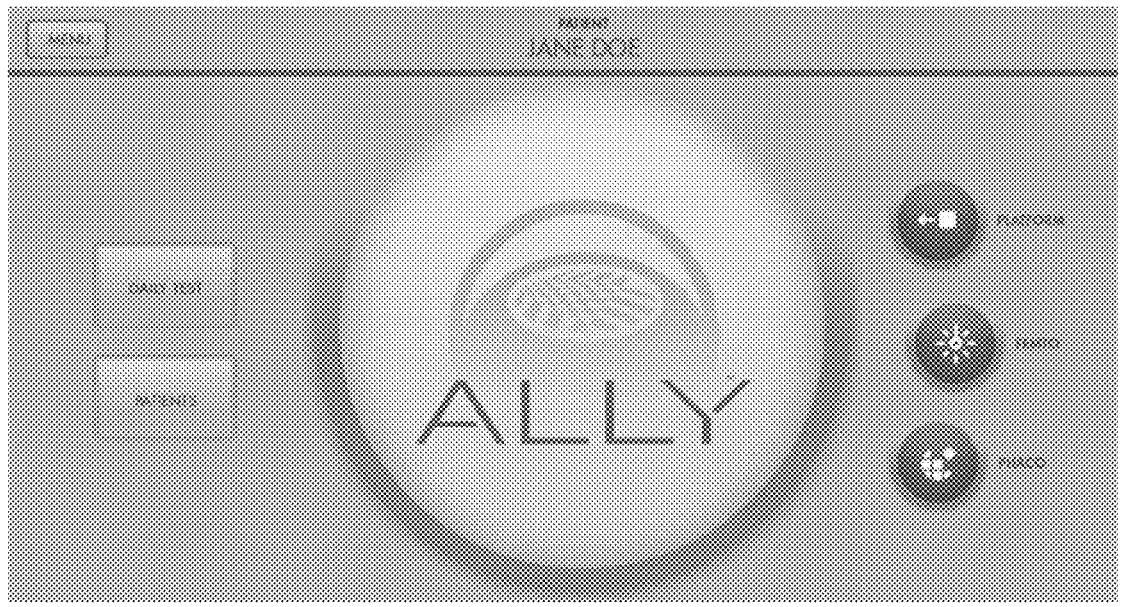
FIGS. 23A-23D are images of an embodiment of GUI screen displays, information and menus in accordance with the present inventions.
Figure 23B:
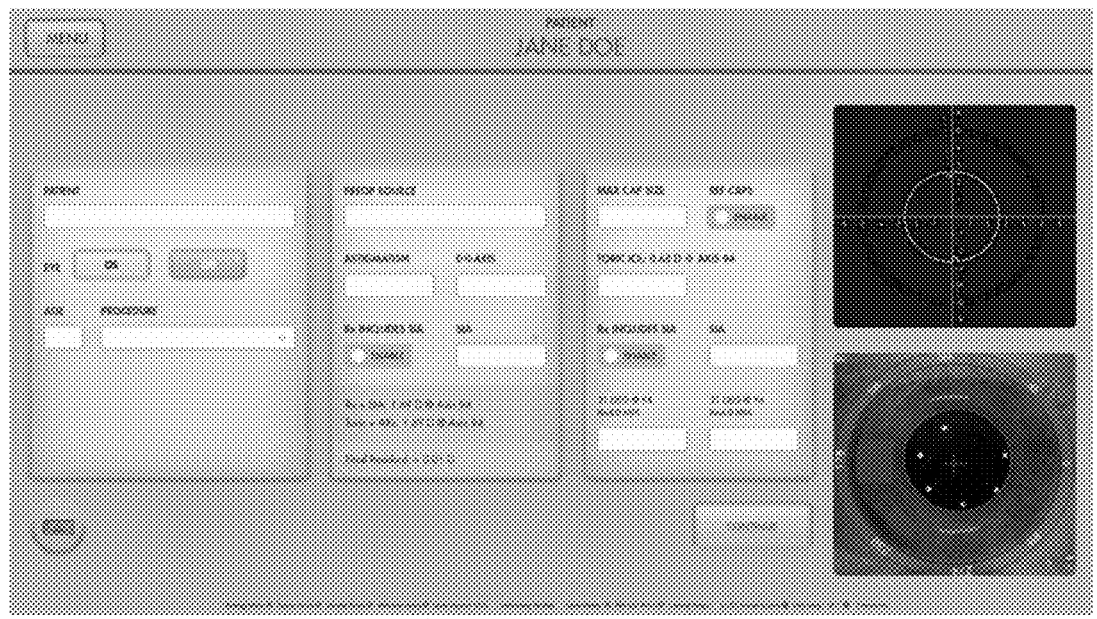
Figure 23C:
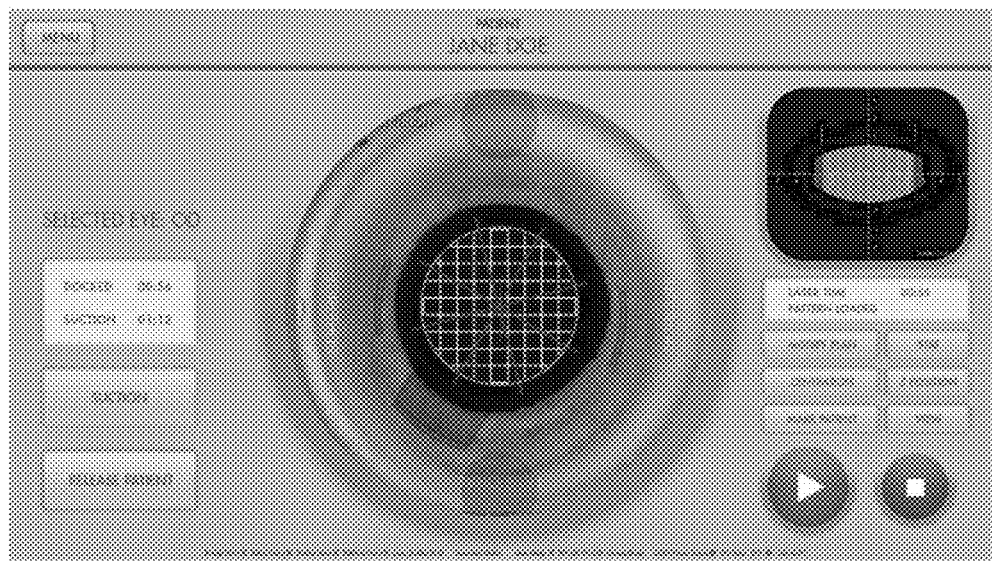
Figure 23D:
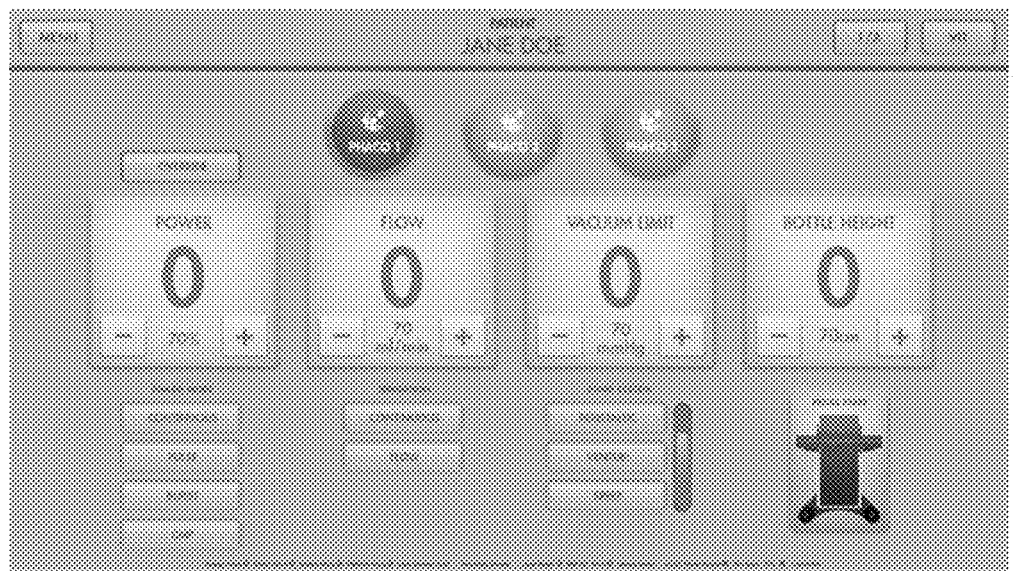

A communication bus can be used for the foot switch, as well as other devices and systems. As illustrated in FIG. 22A, The bus is terminated at each end, then multiple devices can be off it without the need for a supervising computer. In this manner, all the devices can talk to each other (e.g., be in control communication, information communication and both). In a preferred embodiment both the Phaco and Femto computers are on the bus with the footswitch. The footswitch can broadcast message packets that can be processed by both computers, e.g., controllers, for the laser system and the phaco system. The main Femto computer can use some of the footswitch controls to fire the laser or perform mode change operations. Other footswitch controls can simultaneously be used by the Phaco computer to perform other operations like control Phaco energy, irrigation or aspiration vacuum.

In an embodiment the bus is a broad cast type bus such as CanBus.

In embodiments TCP/IP can be used. However, commercially available foot switches are typically not TCP/IP based. Bluetooth or hardwired footswitch may also be used, but are less preferred.

Example 41

Figure 20:
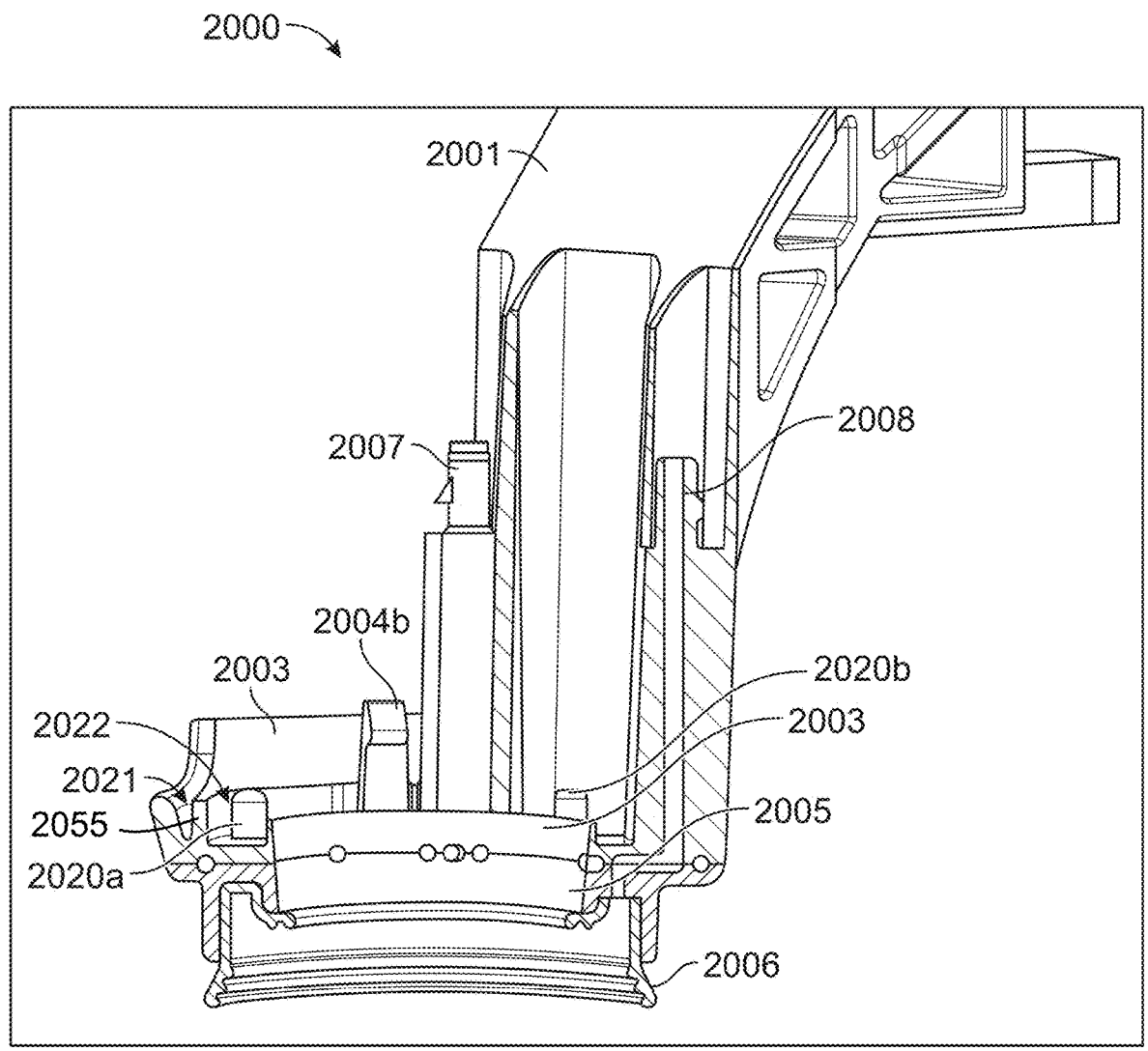
FIG. 20 is a cross sectional perspective view of an embodiment of a PID in accordance with the present inventions.
Figure 20A:
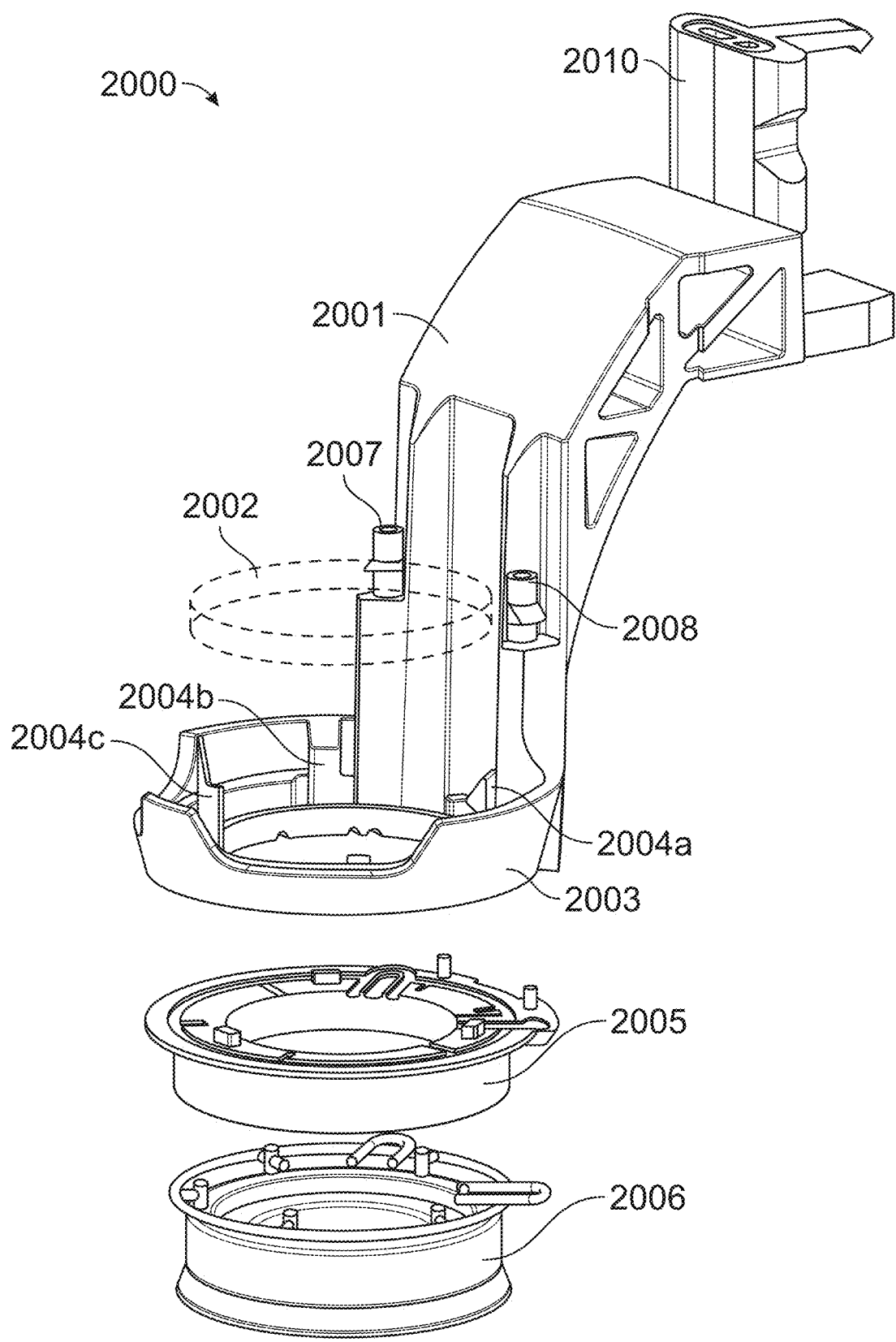
FIG. 20A is a perspective expanded view of the PID of FIG. 20.
Figure 20B:
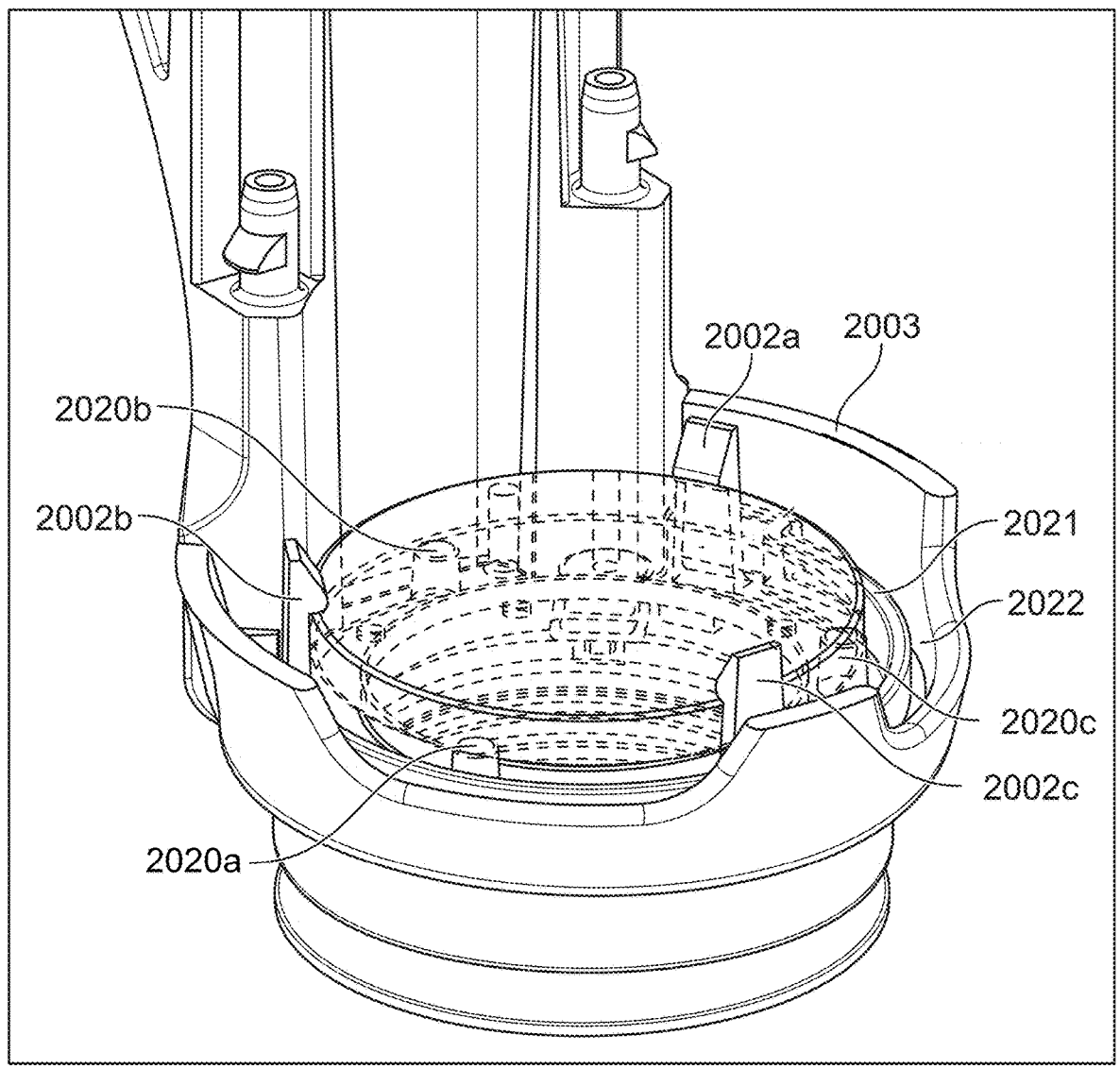

Turning to FIGS. 20, 20A, 20B there is shown an embodiment of a PID 2000. The PID has four components greatly reducing the cost and complexity of assembly and making cleaning easier, compared to more complex PIDs. The PID can be single use or reusable. The PID 2000 has an integral, e.g., unitary arm 2001 that has an engagement means, e.g., clip 2010, for attaching to the system (e.g., laser, laser-ultrasound, femto-phaco, etc.). The PID 2000 further has two ports 2007, 2008 that can be used for fluid transport and vacuum. Preferably 2008 is used for vacuum and 2007 is used for delivery of BSS. The PID 2000 has a window 2002 that is positioned in retaining ring 2003, and held in place by clips 2004a, 2004b, 20004c. A unitary annular vacuum ring 2005 engages the proximal end of retaining ring 2003. Annular vacuum ring 2005 is in fluid communication with ports 2007 and 2008. Annular vacuum ring 2005 is preferably a unitary piece. Annular vacuum ring 2005 is engaged and holds flexible eye engagement ring 2006, which is in fluid communication with one or both ports 2007, 2008.

The PID 200 has a window support and fluid management system, that has pins 2020a, 2020b, 2020c (which preferably are integral, i.e., unitary, parts of ring 2003). The pins support the window 2002 on the proximal (under) side of the window, while the clips 2002a, 2002b, 2002c engage the sides and distal (top) of the window 2002. The pins keep the window above the two fluid channels, an outer fluid channel 2021, and an inner channel 2022. The channels are separated by an annular wall, e.g, ring or ridge 2055. In an embodiment, the high outer channel 2021 (and thus the height of the ring 2055) is slightly lower, than the pin, for example about 1 mm, about 0.7 mm, about 0.5 mm lower than the top of the pins. The inner and outer channels serve as a fluid reservoir system keeping the fluid in contact with the bottom side of the window, while allowing bubbles to escape and excess fluid to overflow into the outer fluid channel 2021.

Example 42

Turning to FIGS. 21, 21A, 21B, 21C, 21D, 21E, there is shown a various view and components of embodiment of a femto-phaco laser system 2100. Like numbers refer to like structures. The system 2100 has a laser subsystem and a phacoemulsification subsystem that are contained within a common housing. The laser subsystem includes a therapeutic laser beam source, and in embodiments a slow pulse duration and long pulse duration therapeutic laser beam source. The laser subsystem includes a laser that defines a therapeutic laser beam path that the therapeutic laser beam travels along and optical components that are positioned or located along the laser beam path. These components would include z-direction focusing optics, and an x-y scanner.

The femto-phaco system 2100 has a first housing 2101 and an optical assembly and scanner housing 2102, that is movably, mechanically and optically associated with the first housing 2101. The housing 2101 is part of an extendable/retractable assembly 2103 that provides horizontal movement. The assembly 2103 also includes base 2105, which is mechanically associated with housing 2101, and is not movable with respect to housing 2101.

The optical assembly and scanner housing 2102 has an arm 2105 that houses portions of the laser beam path and the optical paths, and thus provides for transmission of the laser beam and optical images.

Mechanically and optically associate with the arm 2105 is a laser delivery and imaging head 2016. Vertical movement of the head 2106 is controlled by joy stick 2107 (and may also be done alone or in combination with the control system, and also through the GUI). The vertical movement can be accomplished by any of the various devices disclosed in this specification.

The head 2016 has a position and determining device 2108 and a patient interface device 2109.

A laser beam movable connector device, e.g., articulated hollow pipe 2110, transmits the laser beam for the laser in housing 2101 to the optics and beam handling devices in housing 2102.

The system has an opening 2114 for holding and storing a phaco tray assembly 2112. The phaco tray assembly has a frame 2122 that holds a support tray 2121 and an engagement pin 2113.

The system 2100 has two openings 2111 (left side) and 2120 (right side) for receiving and holding pin 2113 and thus the phaco tray assembly 2122. In this manner the system 2100 is non-handed, such that it can be configured for use in identical manners on both the right and left sides, and the tray and tray assembly is non-handed, as it can be used on both the left and right sides of the system.

The system 2100 has a phaco cassette 2115 and ports 2116 for connecting phaco related components (e.g., air, VIT, DIA, control cables, etc.).

The system 2100 has two monitors 2117, 2118 that are preferably graphic user interfaces (GUI) that display information and menus and take input, e.g., instructions from the operator of the system. The GUIs can display control and information menus such as those shown in FIGS. 23A to 23D.

The system 2100 has an emergency stop 2119.

In the embodiment of this example the position and determining device 2108 has 5 Scheimpflug camera assemblies, e.g., 2123, 2124, 2125, 2126. The head 2106 has a laser delivery opening 2128. The laser beam path and the image path go through this opening. The opening can have a clear window, transmissive to the laser beam and images, it can also have a cap, iris or other closure device that closes the window when the laser is not being used, e.g., when the device is in a retracted position, or when the phaco system is being operated.

Figure 21:
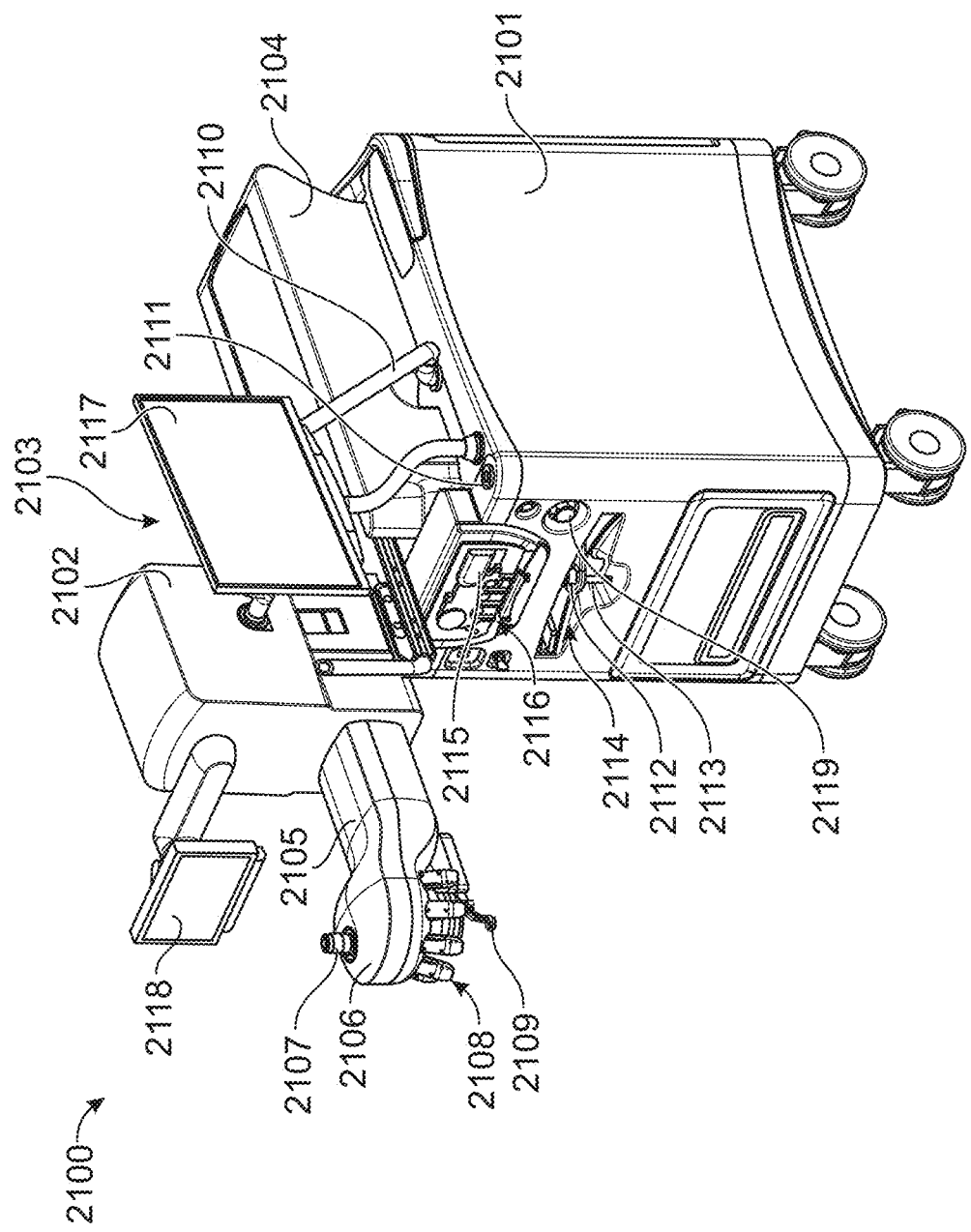
FIG. 21 is a perspective view of an embodiment of a femto-phaco system in the extended position accordance with the present inventions.
Figure 21A:
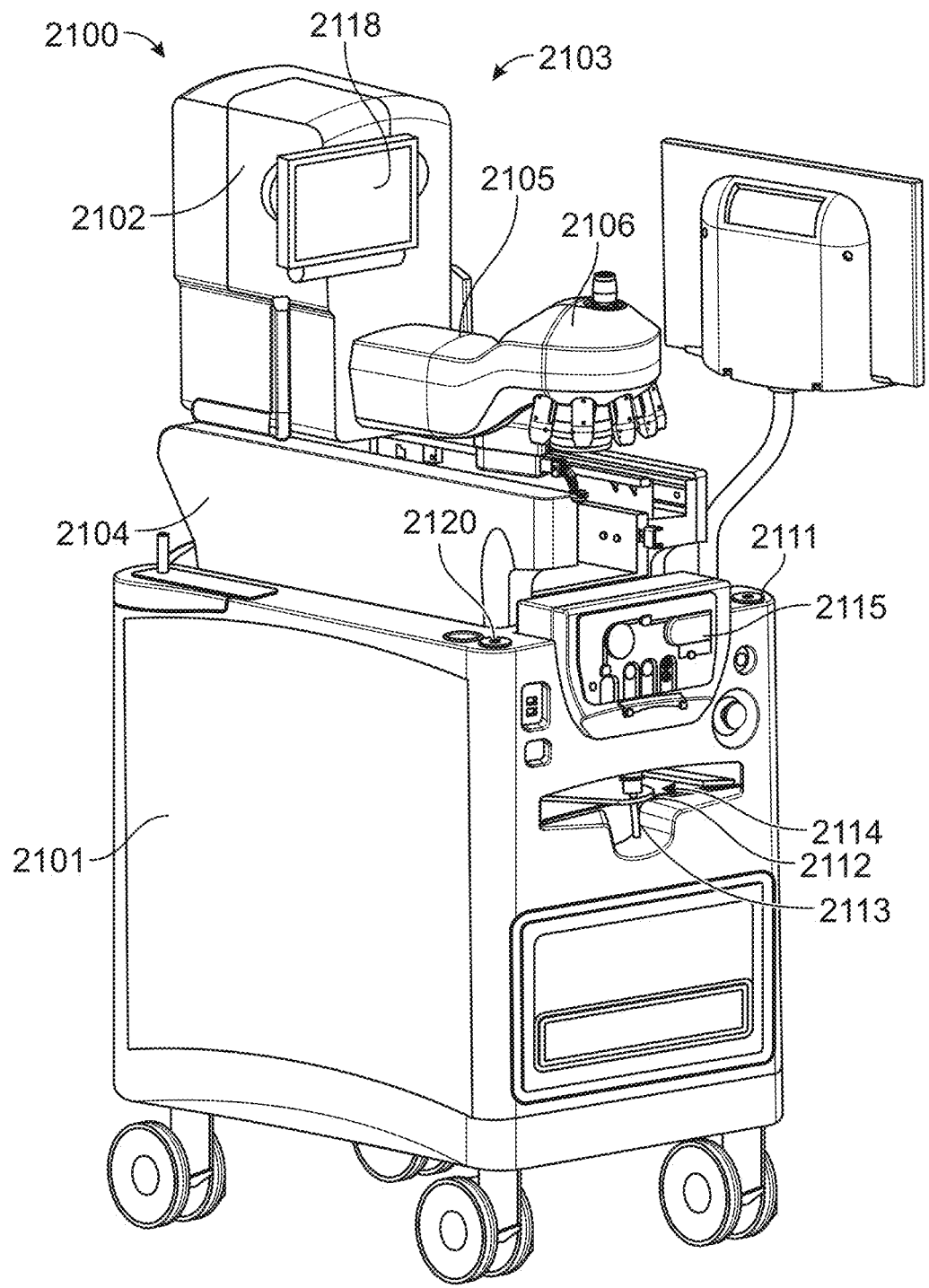
FIG. 21A is a perspective view of the system of FIG. 21, showing the system in the retracted position and from the other side.
Figure 21B:
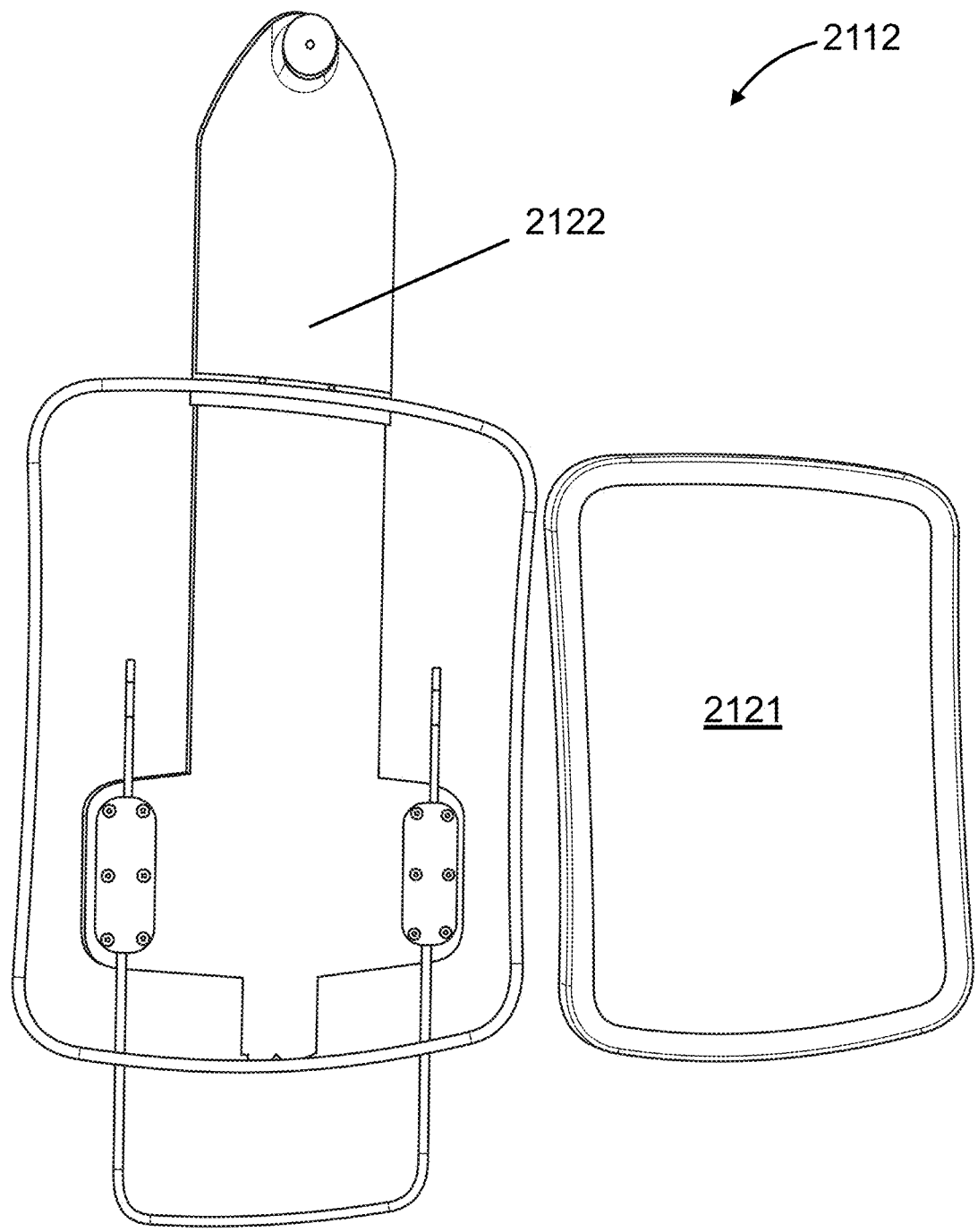
FIG. 21B is a plan view of the tray assembly of the system of FIG. 21.
Figure 21C:
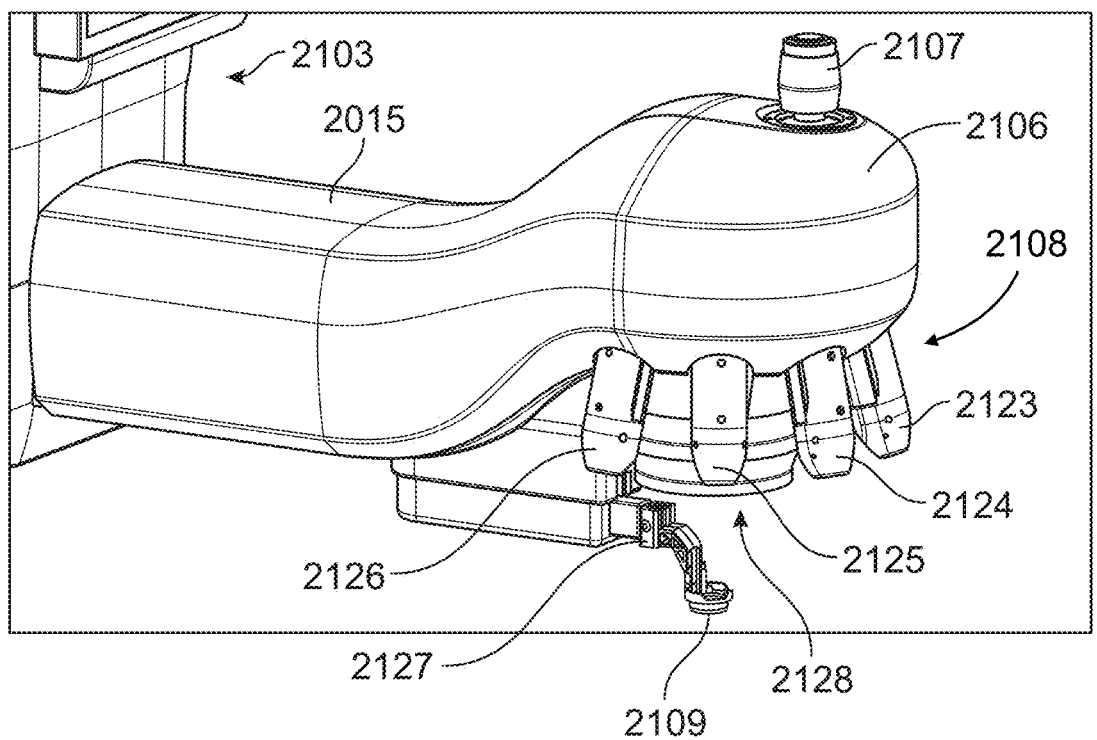
FIG. 21C is a perspective view a portion of the system of FIG. 21.
Figure 21D:
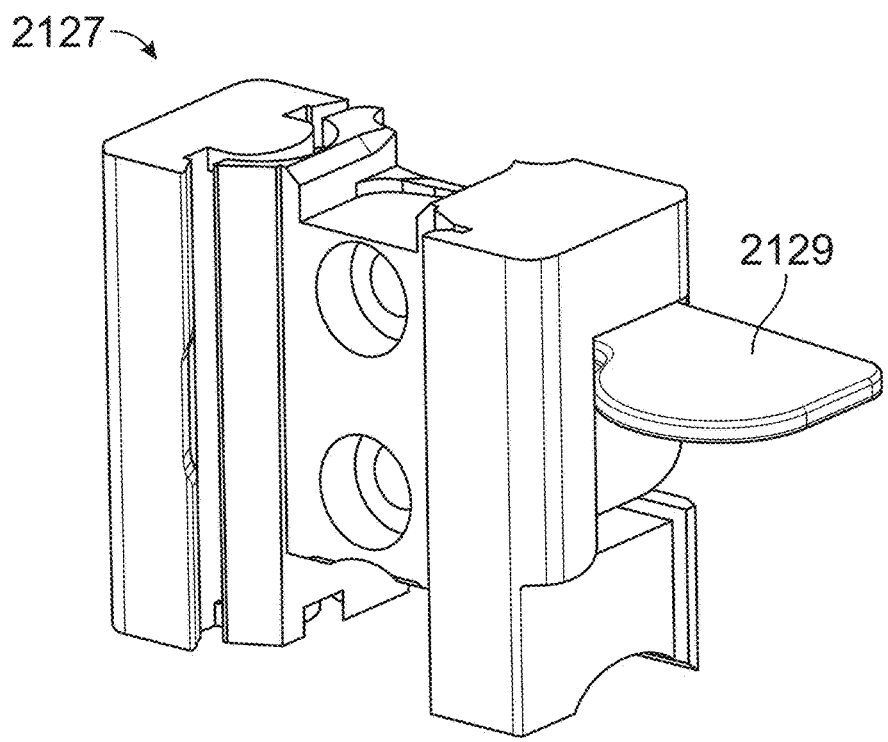
FIG. 21D is a perspective view of the locking engagement device of the system of FIG. 21 in the open position.
Figure 21E:
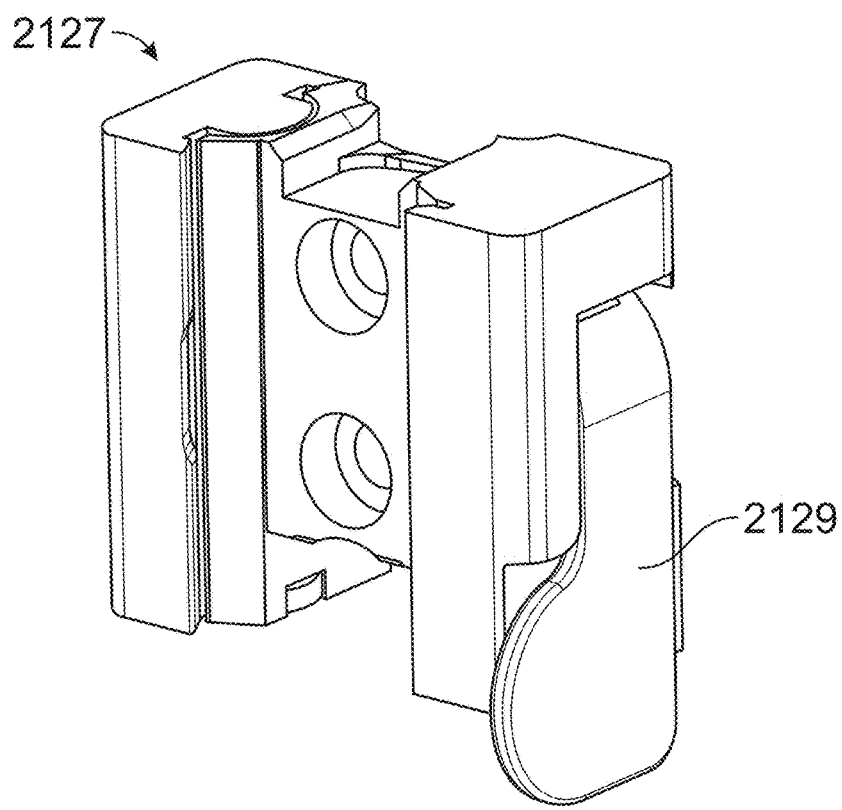
FIG. 21E is a perspective view of the locking engagement device of the system of FIG. 21 in the closed position.

The PID 2109, for example, can be the PID of Example 41. The PID 2109 is attached to the laser head 2106, and thus the laser system 2100, through PID locking and engagement device 2127. The device 2127 has a locking lever tab 2129 that is moveable between a locked position (as shown in FIG. 21E) and an unlocked position (as shown in FIG. 21D).

The arm 2105 that houses the therapeutic laser beam path, as well as other optical paths. In embodiments the arm 2105 also houses or carries control and power cables for the imaging and position apparatus and the docking assembly (not shown in this figure).

The system 2100 has a common power supply for the laser subsystem, and the phaco subsystem. The common power supply provides all power for the entire system, eliminating the need for secondary power supplies, or sources of power. This permits the system to plugged into a single power supply in the operating room.

The system 2100 has a common control system, that includes emergency stop button or switch 2119. The common control system has a controller operating control software or operating instructions. In a preferred embodiment the common control system is in control communication with one or more of and preferably all of: a control system and controller in the laser subsystem; a control system and controller in the phaco subsystem; in control communication with the operator interface; in control communication with the emergency stop 2119; and in communication with a network that is for example a patient medical record system, an accounting system, and combinations and variations of these configurations.

In an embodiment the docking system (preferably with the joystick), and imaging and position determining apparatus are controlled by the laser subsystem control system. In embodiments they may in whole or in part be controlled directly by the common control system. In an embodiment the laser control system and the phaco control system are partially, and can be fully integrated into a single common control system. Thus, in an embodiment only one control system, or a single control system is present in the femto-phaco system. In an embodiment to this Example the system uses the bus communication system of Example 40, which is also depicted in FIG. 22A.

Example 43

Turning to FIG. 22A there is shown the system 2100 of Example 42, to which a foot switch 2130 has been added. The foot switch is in control communication with on the system computers, e.g., controllers, and devices of the system by wireless communication line 2131.

The embodiment of this example uses the bus communication system of Example 40, which is also depicted in FIG. 22A.

Example 44

In an embodiment an integrated laser-ultrasound system, has a first housing, a second housing, a GUI and a means for optically connecting the first housing and the second housing. The second housing is moveably associated with the first housing. The laser-ultrasound system has an assembly having a therapeutic laser for providing a therapeutic laser beam along a laser beam delivery path. The laser has a therapeutic laser control system. The laser-ultrasound system also has a phacoemulsification system for providing therapeutic ultrasonic energy, and this system has a phacoemulsification system control system. At least a portion of the therapeutic laser and the phacoemulsification system, and preferably all of these two systems are located within the first housing;

This integrated laser-ultrasound system, has an integration control system in control communication with at least one of, and preferably all of the therapeutic laser control system, the phacoemulsification system and the GUI.

This integrated laser-ultrasound system, also has a safety interlock, whereby the laser system is prevented from firing the therapeutic laser when the phacoemulsification system is in operation. The safety interlock is in control communication with one or more of the integration control system and the laser control system. The safety interlock can also be in control communication with the phacoemulsification control system.

This integrated laser-ultrasound system, also has a beam shaping and directing assembly comprising a z-focus, a scanner and a lens. This beam shaping and directing assembly is contained in the second housing. Preferably the entirety of this assembly is contained within the second housing.

The means for optically connecting the first housing and the second housing is in optical communication with the therapeutic laser and the beam shaping and directing assembly. This means for optically connecting can be an articulated hollow light pipe, a fiber, or any of the other means for transmitting laser energy disclosed in this specification.

This integrated laser-ultrasound system, also has an arm attached to the second housing and in optical communication with the beam shaping and directing assembly. The arm having a distal end and a proximal end, wherein the distal end is adjacent the second housing, and preferably mechanically attached, and in embodiments integral with the second housing. The system has a laser delivery head that is adjacent and preferably attached to the proximal end of the arm. The laser delivery head has an optical element that is on the laser beam delivery path. This optical element, can be for example a mirror, that receives and directs the laser beam along the laser beam delivery path through an opening in the laser delivery head. Thus, for example this optical element can turn the beam 90 degrees from horizontal to vertical. This optical element may also include lenses that receive, shape and transmit the laser beam. These lenses may be before or after the mirror on the optical path.

As preferably configured the arm contains, e.g., houses, a portion of the laser beam delivery path, in particular that portion from the beam shaping and directing assembly to the laser head. In this manner the arm places the laser delivery head in optical communication with the beam shaping and directing assembly.

Preferably this system has a means for determining the shape and position of a structure of the eye, which can be a Scheimpflug assembly, an OCT assembly or both. This means is preferably located in, on, or forms a part of the laser delivery head. The means for determining the shape and position is in control communication with one or more of the integration control system, the therapeutic laser control system, the phacoemulsification control system and all of these. Preferably the means is at least in communication with the integration control system, the laser control system or both.

This system is also configured to be placed around the patient at multiple clocking angles or positions. preferably this system is configured to be located at an angle with respect to a patient position, wherein the angle is defined by a longitude axis of the arm and a patient axis; wherein the angle comprises the angles of about 45°, about 90°, about 135°, and about 180°.

In an embodiment of this system it has one or more of the following features: it configured to provide two therapeutic laser beams having different pulse durations; it has an iris registration system; the therapeutic laser is a femtosecond laser, a picosecond laser or both.

Example 44A

The system of Example 44 has a foot switch in control communication with one or more of the integration control system, the therapeutic laser control system, and the phacoemulsification control system. These systems may also be configured to provide two therapeutic laser beams having different pulse durations.

Example 44B

The systems of Examples 44, and Example 44A, can also have the integration control system, the therapeutic laser control system or both having a plurality of predetermined laser delivery patterns. These predetermined laser delivery patterns can be contained within the control system(s) or can be located in a memory device associated with and accessible by the control system(s). Further this system's integration control system, the phacoemulsification control system or both have, a plurality of predetermined phacoemulsification procedures. These predetermined phacoemulsification procedures would include for example the parameters (e.g. power) and types of procedures (e.g., chop) that are sef forth in the Ultrasound/Phacoemulsification—Generally section of this specification.

This system is further configured to determine information about a cataract in a lens of an eye. The shape and position determining device on the laser head can provide data, e.g., optical images, to form a basis for the determination of the determined information. A separate imaging system may also be used to provide this data. One or more of the control systems then makes the determination based upon the data. This determined information, for example, and preferably is the grade of the cataract. For example, this can be one of three, or one of four grades.

The system is configured to recommend a laser-phaco combined therapy. This recommendation is based in whole or in part upon the determined information about the cataract.

The laser-phaco combined therapy, preferably a two-component therapy. Thus, having a laser component, that is at least one of the plurality of predetermined laser delivery patterns; and, a phaco component having at least one of the plurality of predetermined phacoemulsification producers.

Example 45

A method of using an integrated laser-phaco system to provide a laser-phaco combination therapy for a cataractous eye. The integrated laser-phaco system has a GUI; a therapeutic laser for providing a therapeutic laser beam along a laser beam delivery path, having a therapeutic laser control system; a phacoemulsification system for providing therapeutic ultrasonic energy, having a phacoemulsification system control system; an integration control system in control communication with the therapeutic laser control system, the phacoemulsification system and the GUI.

Thus, the system can be used to determine, and determines information about the cataract in a cataractous lens. Preferably, this determined information is a grade of the cataract.

Thus, the system can be used to determine, and determines, a laser-phaco combination therapy. This laser-phaco combination therapy preferably is a two-component therapy. Thus, having a laser component, that is at least one of the plurality of predetermined laser delivery patterns; and, a phaco component having at least one of the plurality of predetermined phacoemulsification producers.

The system can be used to recommend, and recommends, the laser-phaco combined therapy that was determined based upon the determined information for the cataract. Preferably the system displays on the GUI the recommended laser-phaco combined therapy; and preferably on the GUI as menu items relating to the recommended laser-phaco combination therapy.

The system can then be instructed, preferably though the GUI menus, but also by voice or a foot switch, to: the recommended combined therapy; only one of the two components of the combined therapy; re-determine one or both of the two components of the combined therapy; and combinations and variations of these. The system preforms these instructions.

The system can then be instructed to perform, and preforms the determined and recommended laser-phaco combination therapy to the lens of the eye of the patient. Because this is a two or more component therapy, one or more instructions to perform steps of that therapy are contemplated and may be required.

Example 46

Generally, in performing procedures using embodiments of the present laser-ultrasound, e.g., laser-phaco, femto-phaco, integrated systems, the laser procedure is performed first, the system is reconfigured, and then the ultrasound procedure, phacoemulsification is performed second. Thus, and generally, after the patient has been prepared, the laser procedures are performed first. These laser procedures could include a capsulotomy, lens fragmentation, and corneal incisions and procedures, as well as other laser procedures discussed in this specification and known to those of skill in the art. The integrated system is then quickly reconfigured, by moving the arm and laser head away from the patient. Thus, transitioning the system from the laser configuration to the ultrasound, e.g., phacoemulsification, configuration, and then performing the ultrasound procedure, e.g., the phacoemulsification. In this manner the phacoemulsification is being performed on an eye and on lens material that has been first cut or fragmented by the laser from the same system, i.e., the integrated system. Once the phacoemulsification procedure is completed, the patient is removed, and the integrated system is quickly reconfigured back to the laser configuration. The system can be quickly and repeatedly transitioned, i.e., reconfigured, between the laser and phaco configurations.

It being understood, that although not presently preferred, the system has the capability to perform laser procedures on the same patient, same or different eye, after the ultrasound procedure, e.g., phacoemulsification, has been performed.

In addition to the foregoing Examples and in furtherance of those Examples, there is also provided a laser system, having: a therapeutic laser system, having a housing; a patient position determining system; having a first component and a second component; the first component mechanically associated with the therapeutic laser system; the second component not mechanically associated with the therapeutic laser system, whereby the second component is free standing from the therapeutic laser system and thereby free moving with respect to the therapeutic laser system; and, wherein the first component, the second component or both are configured to determine a relative position of the second component with respect to the first component.

Moreover, there is provided a laser-ultrasound system, having: a therapeutic laser system; a phacoemulsification system for providing therapeutic ultrasonic energy; and, a safety interlock, whereby the laser system is prevented from firing the laser when the phacoemulsification system is in operation.

Still further, there is provided a laser-ultrasound system, having: a therapeutic laser system; a phacoemulsification system for providing therapeutic ultrasonic energy; and, a microscope integrated into the system.

Furthermore, there is provided a laser-ultrasound system, having: a therapeutic laser system; a phacoemulsification system for providing therapeutic ultrasonic energy; and, a Scheimpflug camera means for determining a shape, a position and both of a structure of an eye.

Moreover, there is provided these laser systems, laser-ultrasound systems, laser-phaco systems, femto-phaco systems, methods and devices, having one or more of the following features: wherein laser system has an integrated ultrasound system; wherein an ultrasound system is contained within the therapeutic laser housing; wherein the ultrasound system is a phacoemulsification system; having a laser safety interlock, whereby the laser cannot be fired when the ultrasound system is in use; wherein the therapeutic laser system is a femtosecond laser system; wherein the ultrasound system is a phacoemulsification system; wherein the patient position determining system has a device selected from the group consisting of an NC electromagnetic tracking system, an electromagnetic tracking system, gyroscope, accelerometer, and magnetometer; wherein the patient position determining system has a device selected from the group consisting of a compass, a laser position deterring device, a sonic position determining device, an RFID device; wherein the therapeutic laser system has an arm extending from the housing; wherein the therapeutic laser system has an arm extending from the housing and having a laser delivery head at a proximal end of the arm; wherein the determined relative position is in 2-dimensional space; wherein the determined relative position is in 3-dimensional space; wherein the patient determining system has an accuracy of at least 95%; wherein the patient determining system has an accuracy of at least 98%; wherein the patient determining system has an accuracy of at least 99%; wherein the system is configured to determine an angle of the arm to a longitudinal patient axis, and to adjust, based at least in part on the angle, a therapeutic laser beam pattern; wherein the angle is determined to within ±5 degrees of accuracy; wherein the angle is determined to within ±3 degrees of accuracy; wherein the angle is determined to within ±2 degrees of accuracy; wherein the second component of the patient position determining system is contained in a patient head rest; wherein the therapeutic laser system has a charging station for the second component of the patient position determining system; wherein the system has a PID; wherein the PID has a meniscus inverter; wherein the PID comprise an arm and wherein the arm defines a vacuum channel and a saline channel; wherein the system has optics defining four pupils, and wherein a laser beam path extends through the two of the pupils; and, wherein at the pupils are conjugate telocentric pupils.

Yet further there is provided a laser-ultrasound system, having: an assembly, the assembly having: a therapeutic laser for providing a therapeutic laser beam along a laser beam path; a phacoemulsification system for providing therapeutic ultrasonic energy; an arm attached to the assembly; the arm having a distal end and a proximal end, wherein the distal end is attached to the assembly; wherein the proximal end has a laser delivery head; the arm contains a portion of the laser beam delivery path; wherein the assembly is located at an angle with respect to a patient position, wherein the angle is defined by a longitude axis of the arm and a patient axis; and, wherein the angle is from 30 degrees to 320 degrees.

Further yet, there is provided these laser systems, laser-ultrasound systems, laser-phaco systems, femto-phaco systems, methods and devices, having one or more of the following features: wherein the angle is selected from the group of angles consisting of 45°, 90°, 135°, 180°, 225°, 270°, and 315°; wherein the arm is configured for arcuate movement about a pivot point on the assembly; wherein the arm is configured for horizontal movement, whereby the arm is extendable from and retractable to the assembly; wherein the arm, the laser head, or both are configured for vertical movement; wherein the laser beam in the laser beam path with the arm is non-collimated; wherein the laser beam in the laser beam path with the arm is within an optical fiber; having optics defining four pupils, and wherein the laser beam path extends through the four pupils; wherein at the pupils are conjugate telocentric pupils; having a means for determining a patient position with respect to the assembly; wherein the means for determining a patient position has a first component and a second component; wherein the first component is mechanically associated with the laser-ultrasound system; wherein the second component is not attached to the therapeutic laser system, whereby the second component is free standing from the therapeutic laser system and thereby free moving with respect to the therapeutic laser system; and, wherein the first component, the second component or both are configured to determine a relative position of the second component with respect to the first component; wherein the therapeutic laser-ultrasound system has a charging station for the second component of the patient position determining system; wherein laser system and the phacoemulsification system are integrated; wherein the laser system and the phacoemulsification system are contained within a housing; wherein the assembly is contained within a housing; having a laser safety interlock, whereby the laser cannot be fired when the phacoemulsification system is in use; and, wherein the therapeutic laser is a femtosecond laser.

Still further there is provided a laser-ultrasound system, having: a therapeutic laser for providing a therapeutic laser beam along a laser beam path; a phacoemulsification system for providing therapeutic ultrasonic energy; and optics defining four pupils, and wherein the laser beam path extends through at least two pupils.

Furthermore, there is provided these laser systems, laser-ultrasound systems, laser-phaco systems, femto-phaco systems, methods and devices, having one or more of the following features: wherein at the pupils are conjugate telocentric pupils; wherein the therapeutic laser and the phacoemulsification system are integrated; wherein the therapeutic laser and the phacoemulsification system are contained within a housing; having a laser safety interlock, whereby the laser cannot be fired when the ultrasound system is in use; and, wherein the therapeutic laser system is a femtosecond laser system.

Moreover, there is provided a laser-ultrasound system, having: a means for providing a first and a second therapeutic laser beam; the system having optics defining a laser beam path; the first and the second laser beam path traveling along the laser beam path; wherein the first therapeutic laser beam has a pulse width of about 1,000 fs to about 2000 fs; the system having a laser beam delivery pattern for performing a lens cut with the first therapeutic laser beam; wherein the second therapeutic laser beam has a pulse width of about 100 fs to about 500 fs; the system having a laser beam delivery pattern for performing a corneal cut with the second therapeutic laser beam; a phacoemulsification system for providing therapeutic ultrasonic energy.

Still further there is provided these laser systems, laser-ultrasound systems, laser-phaco systems, femto-phaco systems, methods and devices, having one or more of the following features: wherein the wavelength of the first laser beam is 1030 nm; wherein the wavelength of the second laser beam is 1030 nm; wherein the wavelength of the first laser beam is 1030 nm and the wherein the wavelength of the second laser beam is 1030 nm; wherein the repetition rate is 320 kHz or less.

Still further there is provided these laser systems, laser-ultrasound systems, laser-phaco systems, femto-phaco systems, methods and devices, having one or more of the following features: having a Scheimpflug camera means; wherein the Scheimpflug camera means has n cameras, wherein at least n−1 cameras have an obstructed view of an eye of a patient in any patient angle from 30 degrees to 320 degrees; wherein n is 5; wherein n is 6; and, wherein the cameras have a separation of at least 40 degrees;

Yet additionally, there is provided a laser-ultrasound system, having: a first configuration for providing a therapeutic laser beam to a patient; a second configuration for providing preforming a phacoemulsification procedure on a patient; and, wherein the transition from the first to the second configuration takes less than 5 minutes.

Still further there is provided these laser systems, laser-ultrasound systems, laser-phaco systems, femto-phaco systems, methods and devices, having one or more of the following features: wherein the transition from laser to phaco is less than 3 minutes; wherein the transition from laser to phaco is less than 2 minutes; wherein the transition from laser to phaco is less than 1 minute; wherein the transition from laser to phaco is less than 45 seconds; wherein the transition from laser to phaco is about 30 seconds; wherein the transition from laser to phaco is from about 1 minute to 30 seconds.

Still further there is provided these laser systems, laser-ultrasound systems, laser-phaco systems, femto-phaco systems, methods and devices, having one or more of the following features: wherein the transition from femto laser to phaco is less than 3 minutes; wherein the transition from femto laser to phaco is less than 2 minutes; wherein the transition from femto laser to phaco is less than 1 minute; wherein the transition from femto laser to phaco is less than 45 seconds; wherein the transition from femto laser to phaco is about 30 seconds; wherein the transition from femto laser to phaco is from about 1 minute to 30 seconds.

Still further there is provided a laser-ultrasound system, having: an assembly defining a foot print and a volume; the assembly having: a therapeutic laser system; and, a phacoemulsification system for providing therapeutic ultrasonic energy; and, wherein the foot print is less than 1,500 sq inches.

Still further there is provided these laser systems, laser-ultrasound systems, laser-phaco systems, femto-phaco systems, methods and devices, having one or more of the following features: wherein the foot print is about 33 inches by about 22 inches; wherein the foot print is about 35 inches or less, by about 35 inches or less; wherein the foot print is about 35 inches or less, by about 22 inches or less; wherein the foot print is from about 400 sq inches to about 800 sq inches; wherein the volume is less than about 40 $ft^3$; wherein the volume is less than about 35 $ft^3$; wherein the volume is less than about 30 $ft^3$; wherein the volume is less than about 25 $ft^3$; and, wherein the volume is less than about 20 $ft^3$.

Moreover, there is provided a laser-ultrasound system, having: a therapeutic laser system; the therapeutic laser system having: an arm having a proximal end; a laser head attached to the proximal end of the arm; and electronics for operating the therapeutic laser system; a phacoemulsification system for providing therapeutic ultrasonic energy having electronics for operating the phacoemulsification system; and, the laser head electrically isolated from the electronics for the phacoemulsification system and the electronics for the therapeutic laser system.

Yet further there is provided a laser system, having: a therapeutic laser beam for providing a therapeutic laser beam; and, an optics assembly for defining a laser beam path; wherein the laser beam path is longer than 300 mm; whereby a laser beam pattern is transmitted along the laser beam path without expansion of the laser beam pattern.

Additionally, there is provided a laser system, having: a therapeutic laser beam for providing a therapeutic laser beam; and, an optics assembly for defining a laser beam path; wherein the laser beam path is longer than 300 mm; whereby a laser beam pattern is transmitted along the laser beam path without any wavefront error.

In addition, there is provided a laser system, having: a therapeutic laser beam for providing a therapeutic laser beam; and, an optics assembly for defining a laser beam path; wherein the laser beam path is longer than 300 mm; whereby a laser beam pattern is transmitted along the laser beam path free from aberrations.

Still further, there is provided these laser systems, laser-ultrasound systems, laser-phaco systems, femto-phaco systems, methods and devices, having one or more of the following features: wherein the laser is a femtosecond laser, and further having an integral phacoemulsification system.

Moreover, there is provided these laser systems, laser-ultrasound systems, laser-phaco systems, femto-phaco systems, methods and devices, having one or more of the following features: having an iris registration device.

Moreover, there is provided these laser systems, laser-ultrasound systems, laser-phaco systems, femto-phaco systems, methods and devices, having one or more of the following features: wherein data and information between the ultrasound system and the laser system are exchanged; wherein the information has a grade of a cataract; wherein the information from the laser system is used to provide a recommended ultrasound energy.

Moreover, there is provided these laser systems, laser-ultrasound systems, laser-phaco systems, femto-phaco systems, methods and devices, having one or more of the following features: wherein data and information between the ultrasound system and the laser system are exchanged; and wherein the information has a grade of a cataract.

Moreover, there is provided these laser systems, laser-ultrasound systems, laser-phaco systems, femto-phaco systems, methods and devices, having one or more of the following features: having an OCT imaging means.

Additionally, there is provided these laser systems, laser-ultrasound systems, laser-phaco systems, femto-phaco systems, methods and devices, having one or more of the following features: wherein the system has a footprint size; and the footprint size is selected from the group of sizes consisting of less than 35× less than 35 inches, less than 35×25 inches, about 35×25 inches, about 33×22 inches, and about 400 sq inches to about 800 sq inches.

Yet further, there is provided these laser systems, laser-ultrasound systems, laser-phaco systems, femto-phaco systems, methods and devices, having one or more of the following features: having a cap on the laser head positioned in the laser beam path, whereby the optical components are protected when the laser is not in an operable configuration.

There is further provided the method of performing a laser operation and a phacoemulsification operation with any of these laser systems, laser-ultrasound systems, laser-phaco systems, femto-phaco systems.

Yet further, there is provided these laser systems, laser-ultrasound systems, laser-phaco systems, femto-phaco systems, methods and devices, having one or more of the following features: wherein a surgical microscope is attached the system housing and in data communication, control communication and both with the control system; wherein the surgical microscope is integral with the system housing; wherein the surgical microscope can accept commands, views (e.g., digital overlays) from the therapeutic laser system in either the laser, e.g., femto or ultrasound, e.g., phaco mode and procedure.

Moreover, there is provided these laser systems, laser-ultrasound systems, laser-phaco systems, femto-phaco systems, methods and devices, having one or more of the following features: wherein a three dimensional (3-D) viewing system is attached the system housing and in data communication, control communication and both with the control system; wherein the 3-D viewing system is integral with the system housing; wherein the 3-D system can accept commands, views (e.g., digital overlays) from the therapeutic laser system in either the laser, e.g., femto or ultrasound, e.g., phaco mode and procedure.

Headings and Embodiments

It should be understood that the use of headings in this specification is for the purpose of clarity, reference, and is not limiting in any way. Thus, the processes compositions, and disclosures described under a heading should be read in context with the entirely of this specification, including the various examples. The use of headings in this specification should not limit the scope of protection afforded the present inventions.

It is noted that there is no requirement to provide or address the theory underlying the novel and groundbreaking processes, laser operations, and laser patterns, enhanced and improved vision, or other beneficial features and properties that are the subject of, or associated with, embodiments of the present inventions. Nevertheless, various theories are provided in this specification to further advance the art in this area. The theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the function-features of embodiments of the methods, laser patterns, laser operations, functions of the eye, devices and system of the present inventions; and such later developed theories shall not limit the scope of protection afforded the present inventions.

The various embodiments of devices, systems, laser shot patterns, activities, and operations set forth in this specification may be used with, in or by, various measuring, diagnostic, surgical and therapeutic laser systems, in addition to those embodiments of the Figures and disclosed in this specification. The various embodiments of devices, systems, laser shot patterns, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations provided in the various embodiments of this specification may be used with each other. For example, the components of an embodiment having A, A' and B and the components of an embodiment having A", C and D can be used with each other in various combination, e.g., A, C, D, and A. A" C and D, etc., in accordance with the teaching of this specification. Thus, the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:

1. A patient interface device (PID) for ophthalmic procedures, the device comprising:
a rigid arm, having a top and a bottom end;
the bottom end comprising an annular ring structure;
the annular ring structure having a top side, a bottom side and an opening configured for the transmission of a therapeutic laser beam;
a first and a second port; wherein the ports are in fluid communication with at least one of the opening, the top side, and the bottom side, wherein the first port defines a first channel and the second port defines a second channel;
the top side of the annular ring structure comprising:
a plurality of pins extending upward from a surface of the top side and defining a pin height;
a plurality of clips extending upwardly above the surface of the top side and having clip engagement surfaces, thereby defining a clip engagement surface height;
wherein the clip engagement surface height is greater than the pin height;
an annular wall extending upwardly from the surface of the top side and defining a wall height; and
wherein the annular wall defines in part a first annular channel and a second annular channel.

2. The PID of claim 1, comprising a window, wherein the window defines a window height; and wherein the window is held between the clip engagement surfaces and the pins; and, wherein the window is positioned over the opening.

3. The PID of claim 1, comprising an annular vacuum ring structure attached to the bottom side of the annular ring structure; and, wherein the annular vacuum ring is in fluid communication with at least one of the ports; the annular vacuum ring structure having a bottom side.

4. The PID of claim 2, comprising an annular vacuum ring structure attached to the bottom side of the annular ring structure; and, wherein the annular vacuum ring structure is in fluid communication with at least one of the ports; the annular vacuum ring structure having a bottom side.

5. The PID of claim 3, comprising a flexible eye engagement ring, having an inner annual skirt and outer annual skirt, and thereby defining a flexible annular vacuum channel configured for engagement with an eye; the flexible eye engagement ring attached to the bottom side of the annular vacuum ring structure and in fluid communication with at least one of the ports.

6. The PID of claim 4, comprising a flexible eye engagement ring, having an inner annual skirt and outer annual skirt, and thereby defining a flexible annular vacuum channel configured for engagement with an eye; the flexible eye engagement ring attached to the bottom side of the annular vacuum ring structure and in fluid communication with at least one of the ports.

7. The PID of claim 1, 2, 3, 4, 5 or 6, wherein the pin height is the same as or lower than the wall height.

8. The PID of claim 1, 2, 3, 4, 5 or 6, wherein the pin height is lower than the wall height.

9. The PID of claim 1, 2, 3, 4, 5 or 6, wherein the pin height is about 1 mm lower than the wall height.

10. The PID of claim 1, 2, 3, 4, 5 or 6, wherein the rigid arm is a unitary structure.

11. The PID of claim 3, 4, 5 or 6, wherein the annular vacuum ring structure is a unitary structure.

12. The PID of claim 1, 2, 3, 4, 5 or 6, wherein the annular ring structure is a unitary structure.

13. The PID of claim 5 or 6, wherein the flexible eye engagement ring is a unitary structure.

14. An integrated laser-ultrasound system comprising the PID of claim 1, wherein the top end of the arm is attached to the system.

15. An integrated laser-ultrasound system comprising the PID of claim 1, wherein the top end of the arm is attached to a laser head of the system.

16. The system of claim 14 or 15, wherein the system is non-handed.

17. The system of claim 14 or 15, wherein the system comprises a phaco tray, a phaco cassette and is non-handed.

18. A method of servicing, upgrading a software, operating, or preforming a surgery using, the system of claim 14 or 15.

19. The system of claim 14 or 15, comprising a wireless foot switch, configured to control the laser, a phacoemulsification system or both.

20. An integrated laser-ultrasound system comprising the PID of claim 1, 2, 3, 4, 5 or 6, wherein the laser system comprises a laser head defining a laser head opening, wherein a therapeutic laser beam path travels through the laser head opening, and associated with the laser head opening is a means for closing the laser head opening during operation of a phacoemulsification system, when the laser head is in a retracted position, or both.

21. A method of laser transmission, the method comprising transmitting a laser beam through the window of any one of the PID of claim 1, 2, 3, 4, 5 or 6.

* * * * *